United States Patent
Kazakov et al.

(10) Patent No.: US 8,962,253 B2
(45) Date of Patent: Feb. 24, 2015

(54) METHODS AND COMPOSITIONS FOR DETECTION OF SMALL RNAS

(75) Inventors: Sergei A. Kazakov, Los Gatos, CA (US); Pavan Kumar, Santa Cruz, CA (US); Brian H. Johnston, Scotts Valley, CA (US)

(73) Assignee: Somagenics Inc., Santa Cruz, CA (US)

( * ) Notice: Subject to any disclaimer, the term of this patent is extended or adjusted under 35 U.S.C. 154(b) by 388 days.

(21) Appl. No.: 13/264,122

(22) PCT Filed: Apr. 13, 2010

(86) PCT No.: PCT/US2010/030922
§ 371 (c)(1),
(2), (4) Date: Jan. 4, 2012

(87) PCT Pub. No.: WO2010/120803
PCT Pub. Date: Oct. 21, 2010

(65) Prior Publication Data
US 2012/0164651 A1   Jun. 28, 2012

Related U.S. Application Data

(60) Provisional application No. 61/168,887, filed on Apr. 13, 2009.

(51) Int. Cl.
*C12Q 1/68* (2006.01)
*C12P 19/34* (2006.01)

(52) U.S. Cl.
CPC .............. *C12Q 1/682* (2013.01); *C12Q 1/6844* (2013.01); *C12Q 1/6865* (2013.01)
USPC ........................................ 435/6.12; 435/91.2

(58) Field of Classification Search
None
See application file for complete search history.

(56) References Cited

U.S. PATENT DOCUMENTS

| | | | |
|---|---|---|---|
| 5,516,664 A | 5/1996 | Hyman | |
| 5,714,320 A | 2/1998 | Kool | |
| 5,854,033 A | 12/1998 | Lizardi | |
| 6,077,668 A | 6/2000 | Kool | |
| 2004/0171047 A1 | 9/2004 | Dahl et al. | |
| 2006/0003337 A1 | 1/2006 | Brandis et al. | |
| 2006/0078894 A1 | 4/2006 | Winkler et al. | |
| 2006/0166245 A1 | 7/2006 | Potter et al. | |
| 2006/0188893 A1 | 8/2006 | Kumar et al. | |
| 2007/0292878 A1 | 12/2007 | Raymond | |
| 2008/0241831 A1 | 10/2008 | Fan et al. | |

FOREIGN PATENT DOCUMENTS

| | | |
|---|---|---|
| EP | 1627925 A1 | 2/2006 |
| EP | 1978104 A1 | 10/2008 |
| EP | 2419537 B1 | 1/2014 |
| WO | 03/002761 | 1/2003 |
| WO | WO 2005/098029 A2 | 10/2005 |
| WO | WO 2006/102309 A2 | 9/2006 |
| WO | 2006/108422 | 10/2006 |

OTHER PUBLICATIONS

Nallur et al. Signal amplification by rolling circle amplification on DNA microarrays. Nucleic Acids Res. (2001) vol. 29, No. 23, e118, pp. 1-9.*

Thomas et al. Determination of the ex vivo rates of human immunodeficiency virus type 1 reverse transcription by using novel strand-specific amplification analysis. J. Virology (2007) vol. 81, No. 9, pp. 4798-4807.*

Wang et al. Oligoribonucleotide circularization by 'template-mediated' ligation with T4 RNA ligase: synthesis of circular hammerhead ribozymes. Nucleic Acids Res. (1998) vol. 26, No. 10, pp. 2502-2504.*

Basyuk et al., "Human let-7 stem-loop precursors harbor features of RNase III cleavage products" Nucleic Acids Research (2003) 31(22):6593-6597.

Cheng et al., "Highly Sensitive Determination of microRNA Using Target-Primed and Branched Rolling-Circle Amplification" Angew. Chem. Int. Ed. (2009) 48:3268-3272.

Demidov "Rolling-Circle amplification in DNA diagnostics: the power of simplicity" Expert Rev. Mol. Diagn. (2002) 2(6):89-95.

(Continued)

*Primary Examiner* — Kenneth R. Horlick
*Assistant Examiner* — David Thomas
(74) *Attorney, Agent, or Firm* — Wilson Sonsini Goodrich & Rosati

(57) ABSTRACT

Currently, the circularization of small RNAs is broadly regarded as an obstacle in ligation-related assays and explicitly avoided while short lengths of linear RNA targets is broadly recognized as a factor limiting use of conventional primers in PCR-related assays. In contrast, the disclosed invention capitalizes on circularization of small RNA targets or their conjugates with oligonucleotide adapters. The circular RNA templates provide amplification of the target sequences via synthesis of multimer nucleic acids that can be either labeled for direct detection or subjected to PCR amplification and detection. Structure of small circular RNAs and corresponding multimeric nucleic acids provide certain advantages over current methods including flexibility in design of conventional RT and PCR primers as well as use of 5'-overlapping dimer-primers for efficient and sequence-specific amplification of short target sequences. Our invention also reduces number of steps and reagents while increasing sensitivity and accuracy of detection of small RNAs with both 2'OH and 2'-OMe at their 3' ends. Our invention increase sensitivity and specificity of detection of microRNAs and other small RNAs with both 2'OH and 2'-OMe at their 3' ends while allowing us to distinguish these two forms from each other.

24 Claims, 67 Drawing Sheets

(56) References Cited

OTHER PUBLICATIONS

Frieden et al., "Tightening the Belt on Polymerases: Evaluating the Physical Constraint on Enzyme Substrate Size" Angew. Chem. Int. Ed. (1999) 38(24):3654-3657.
Jonstrup et al., "A microRNA detection system based on padlock probes and rolling circle amplification" RNA (2006) 12:1747-1752.
Kong et al., "PCR hot-start using duplex primers" Biotechnology Letters (2004) 26:277-280.
Lizardi et al., "Mutation detection and single-molecule counting using isothermal rolling-circle amplification" Nature Genetics (Jul. 1998) 19:225-232.
Navarro et al., "Reverse transcription polymerase chain reaction protocols for cloning small circular RNAs" Journal of Virological Methods (1998) 73:1-9.
Zhang et al., "Amplification of target-specific, ligation-dependent circular probe" Gene (1998) 211:277-285.
EP 10765038.4 Search Report dated Jul. 23, 2012.
EP 10765038.4 Office action dated Mar. 20, 2013.
PCT/US2010/030922 Search Report and Written Opinion dated Jan. 26, 2011.
Szymkowiak, et al. Rapid method for the characterization of 3' and 5' UTRs of influenza viruses. J Virol Methods. Jan. 2003;107(1):15-20.
Aravin, et al. Identification and characterization of small RNAs involved in RNA silencing. FEBS Lett. Oct. 31, 2005;579(26):5830-40. Epub Aug. 18, 2005 .
Chammongpol, et al. miRtect-IT: a novel method for small RNA detection. Biotechniques. Jan. 2008;44(1):129-31.
Chen, et al. Real-time quantification of microRNAs by stem-loop RT-PCR. Nucleic Acids Res. Nov. 27, 2005;33(20):e179.
Harcourt, et al. Amplified microRNA detection by templated chemistry. Nucleic Acids Res. May 2012;40(9):e65. doi: 10.1093/nar/gkr1313. Epub Jan. 25, 2012.

Jiang, et al. Real-time expression profiling of microRNA precursors in human cancer cell lines. Nucleic Acids Res. Sep. 28, 2005;33(17):5394-403. Print 2005.
Jonstrup, et al. A microRNA detection system based on padlock probes and rolling circle amplification. RNA. Sep. 2006;12(9):1747-52. Epub Aug. 3, 2006.
Kumar, et al. miR-ID: a novel, circularization-based platform for detection of microRNAs. RNA. Feb. 2011;17(2):365-80. doi: 10.1261/rna.2490111. Epub Dec. 17, 2010.
Lu, et al. PCR-based expression analysis and identification of microRNAs. J RNAi Gene Silencing. Jul. 28, 2005;1(1):44-9.
Maroney, et al. A rapid, quantitative assay for direct detection of microRNAs and other small RNAs using splinted ligation. RNA. Jun. 2007;13(6):930-6. Epub Apr. 24, 2007.
Mattie, et al. Optimized high-throughput microRNA expression profiling provides novel biomarker assessment of clinical prostate and breast cancer biopsies. Mol Cancer. Jun. 19, 2006;5:24.
Overhoff, et al. Quantitative detection of siRNA and single-stranded oligonucleotides: relationship between uptake and biological activity of siRNA. Nucleic Acids Res. Dec. 2, 2004;32(21):e170.
Raymond, et al. Simple, quantitative primer-extension PCR assay for direct monitoring of microRNAs and short-interfering RNAs. RNA. Nov. 2005;11(11):1737-44.
Saba, et al. Target labelling for the detection and profiling of microRNAs expressed in CNS tissue using microarrays. BMC Biotechnol. Dec. 12, 2006;6:47.
Sharbati-Tehrani, et al. miR-Q: a novel quantitative RT-PCR approach for the expression profiling of small RNA molecules such as miRNAs in a complex sample. BMC Mol Biol. Apr. 10, 2008;9:34. doi: 10.1186/1471-2199-9-34.
Sioud, et al. Profiling microRNA expression using sensitive cDNA probes and filter arrays. Biotechniques. Oct. 2004;37(4):574-6, 578-80.

* cited by examiner

FIGURE 1
A
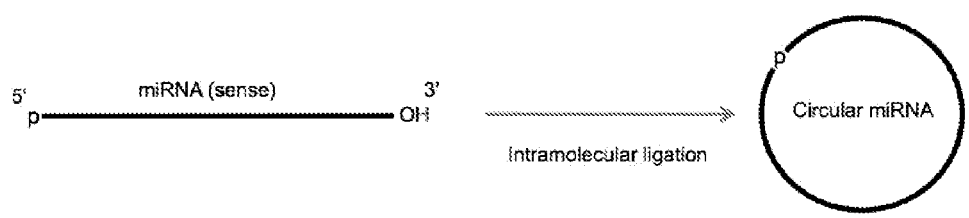
B
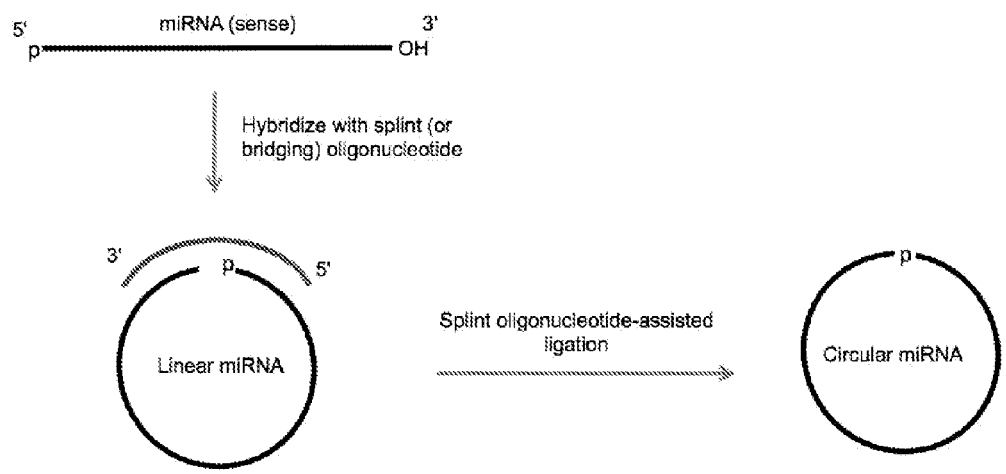

FIGURE 2
A
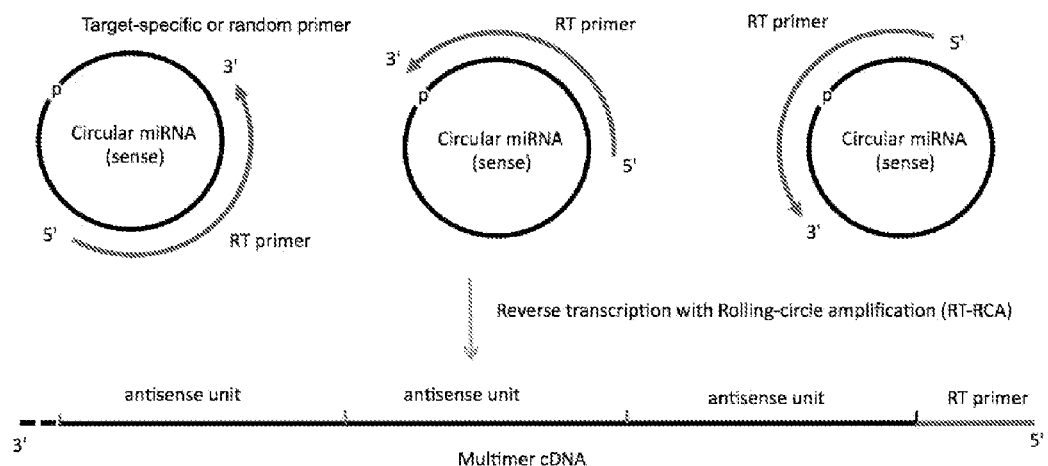
B
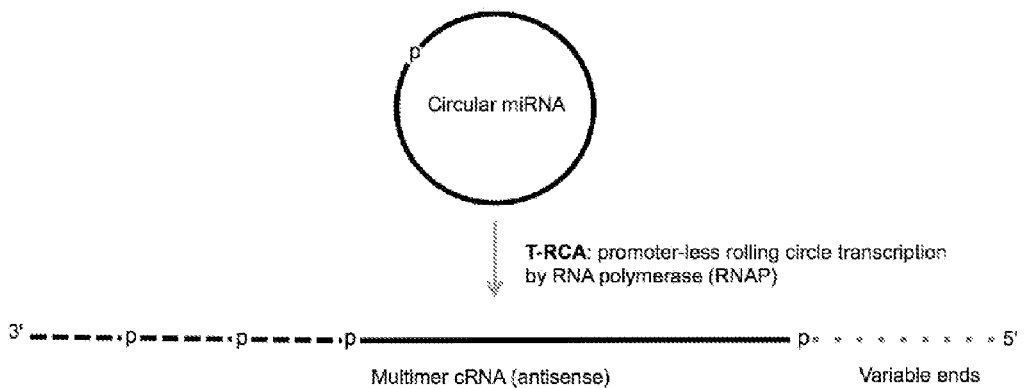

FIGURE 3A-B
A
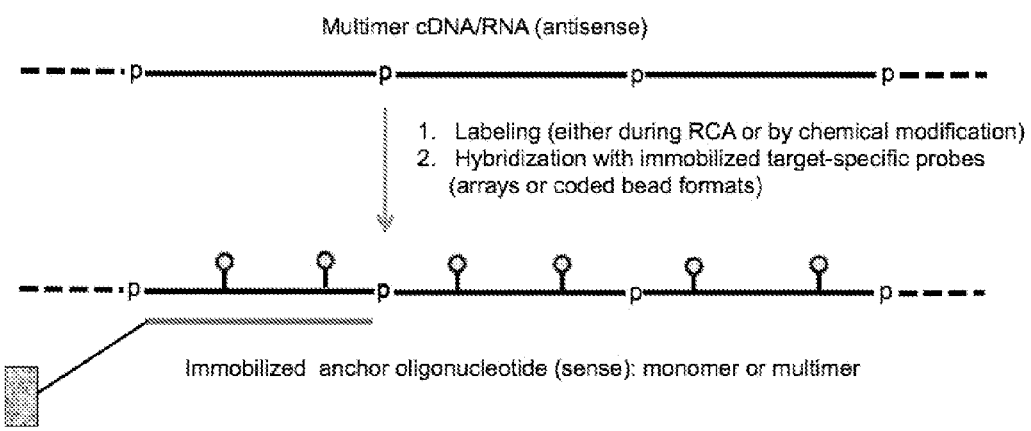
B
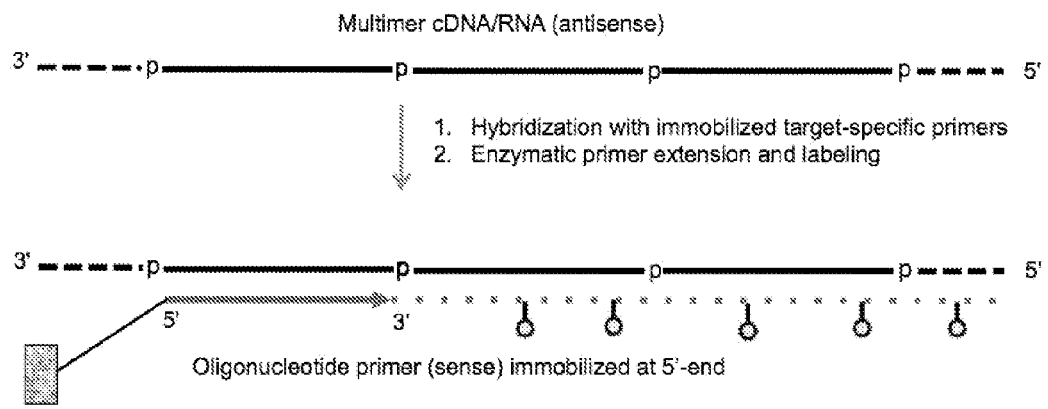

FIGURE 5
A
Monomer template encoding small RNA sequence is too short for normal PCR primers
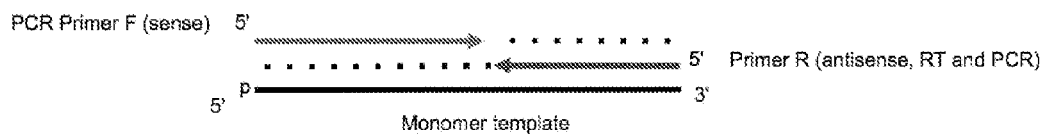
B
Multimer cDNA template encoding repeats of the same miRNA sequence allows longer primers that can overlap at their 5' ends
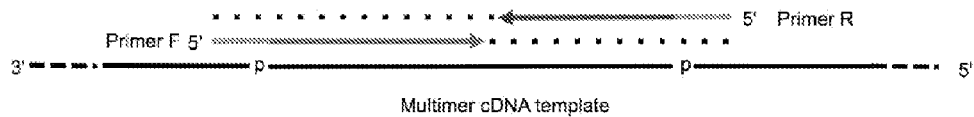
C
5'-overlapping versus 3'-overlapping PCR primers
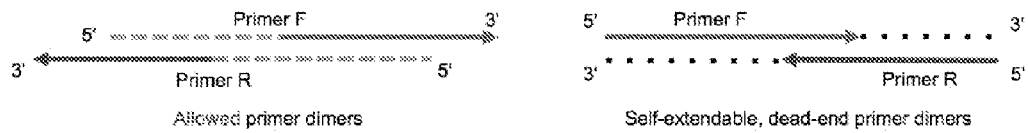

A

FIGURES 6C-D
C
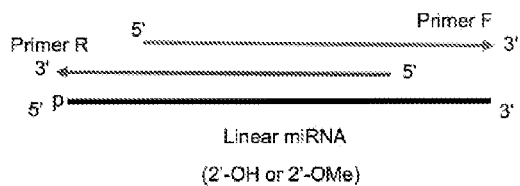
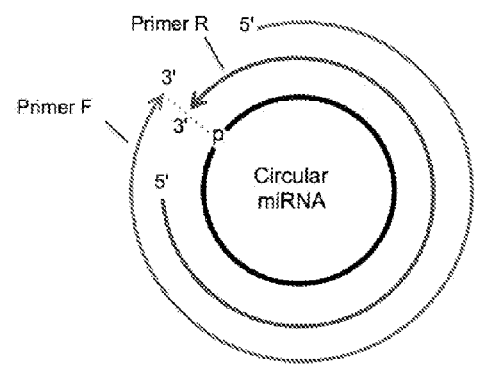
D
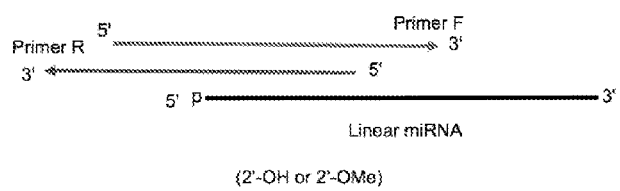
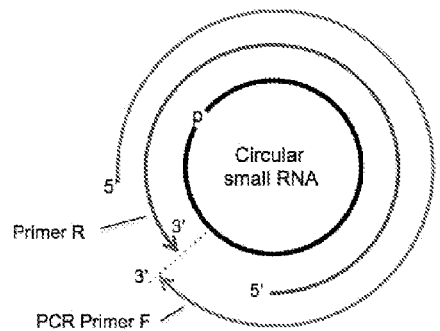

FIGURE 10
A
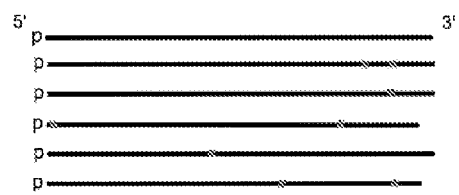
B
C
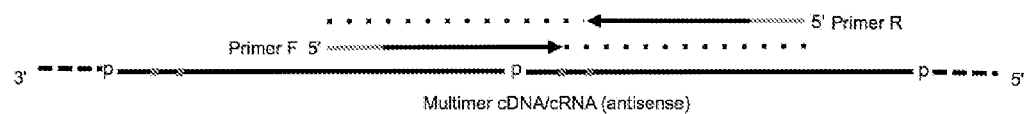
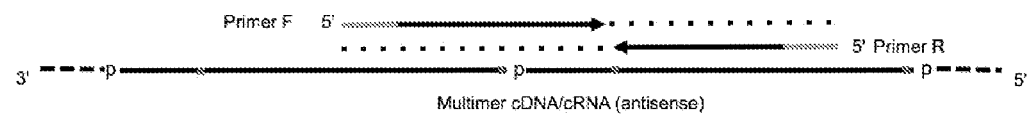

A

FIGURE 13A
A
Examples of quenched 5'-overlapping primer pairs (qOPP)
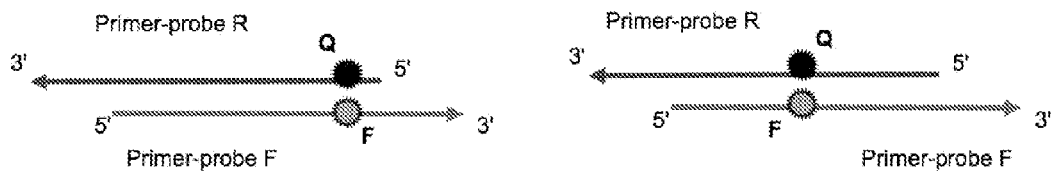
Examples of fluorescent products of qOPP extension in the presence of multimer cDNA target
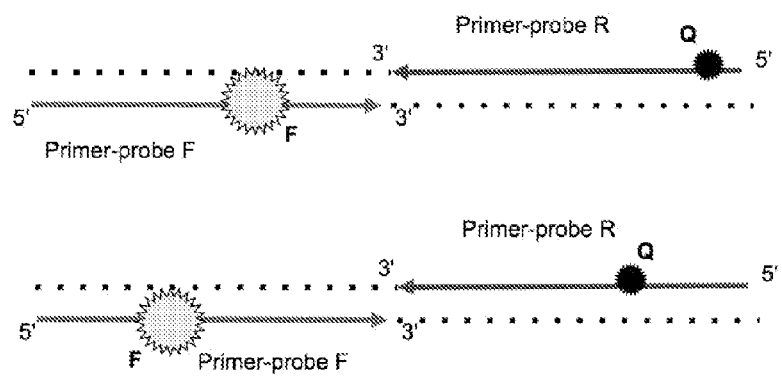

FIGURE 19
A
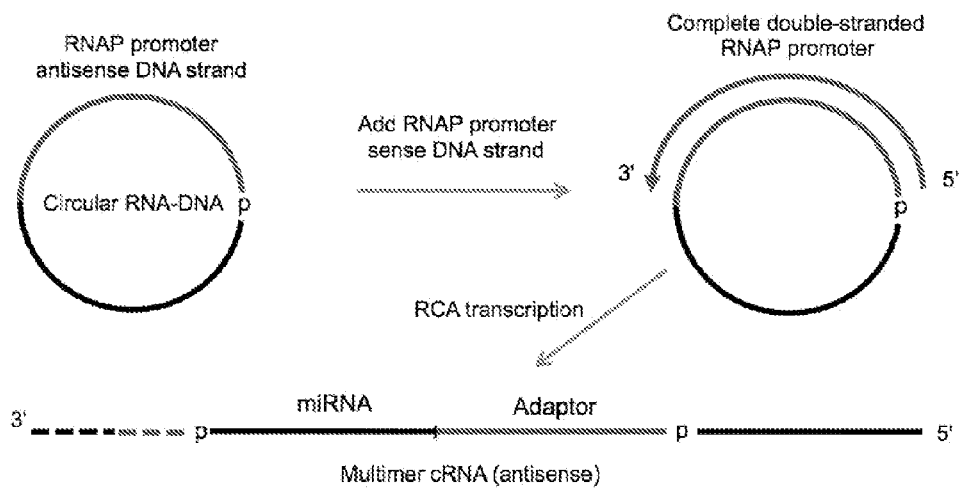
B
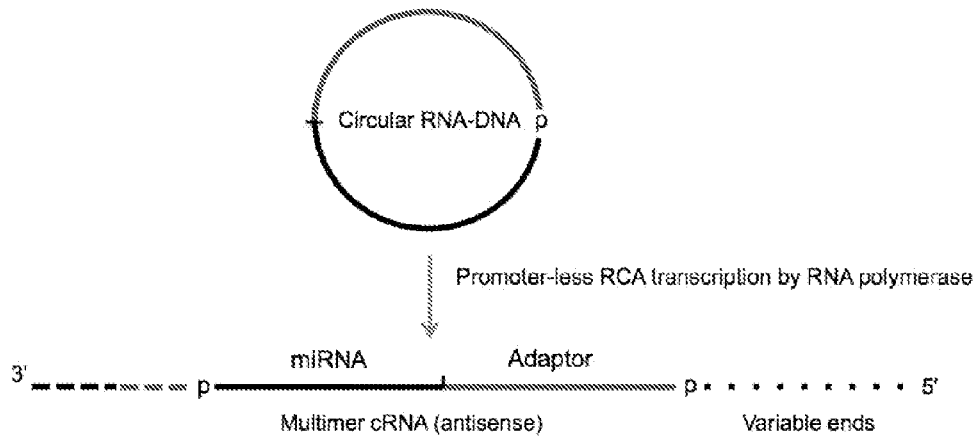

FIGURE 21
A
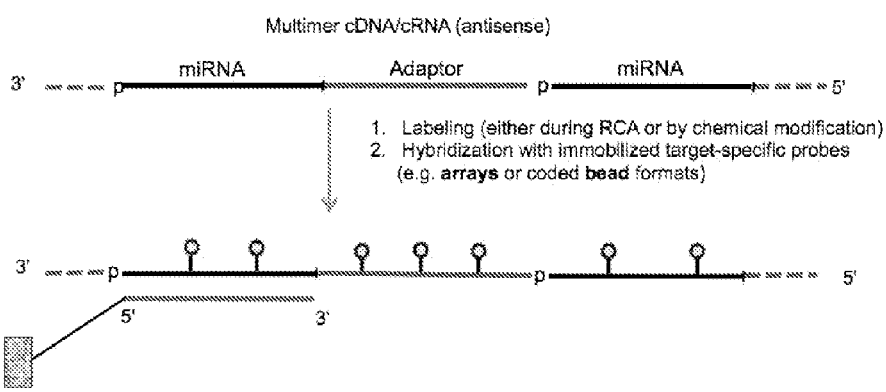
B
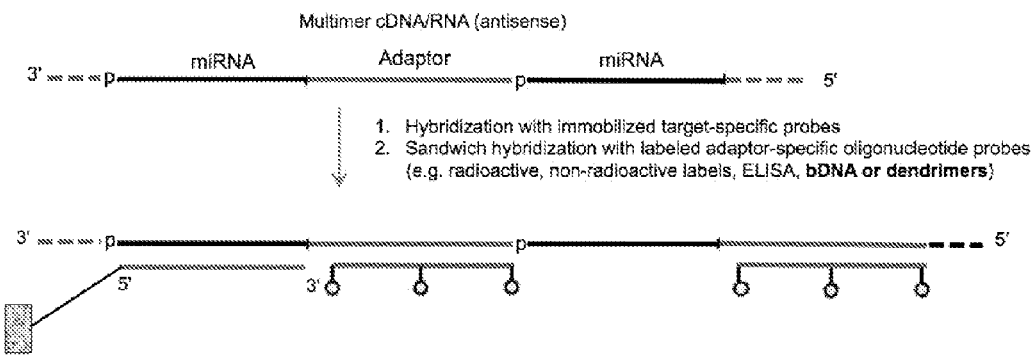

FIGURE 22
A
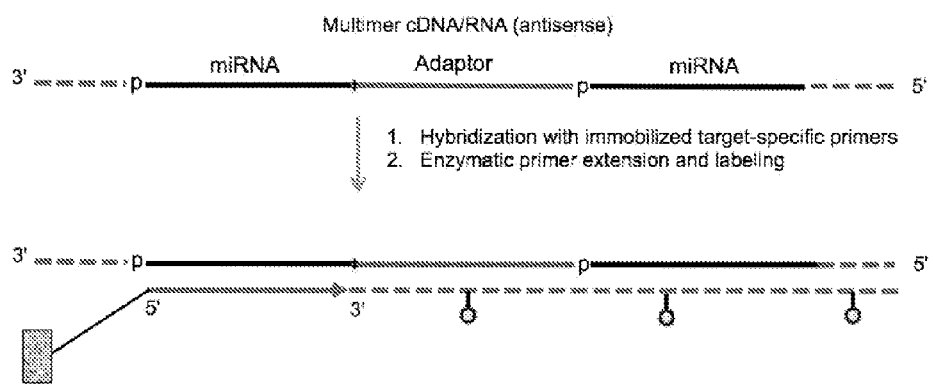
B
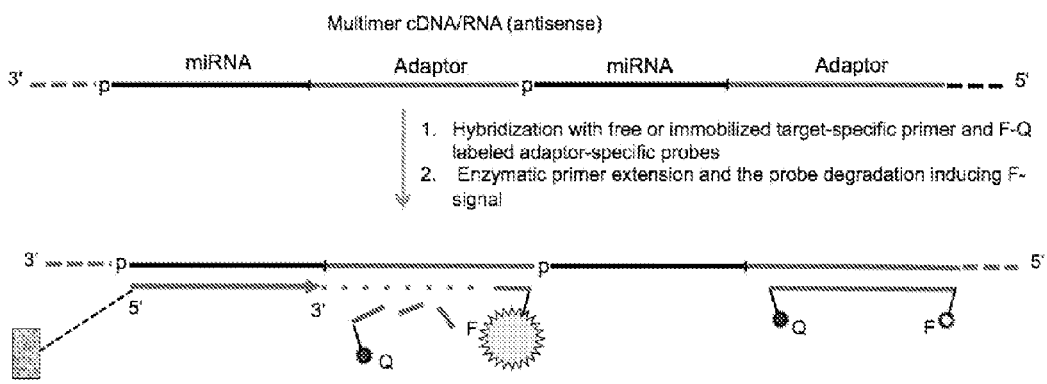

A

D miRNA-specific 5'-overlapping primers that are partially complementary/corresponding to both adaptor and target miRNA sequences (FOTA primers)

Multimeric PCR amplicons encoding selected miRNA sequences

A hsa-let-7b                    hsa-miR-127

FIGURE 28A-B
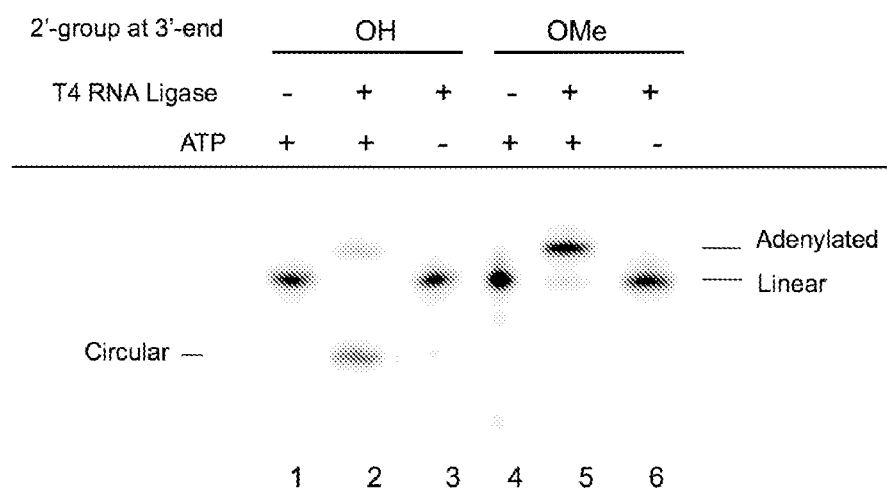
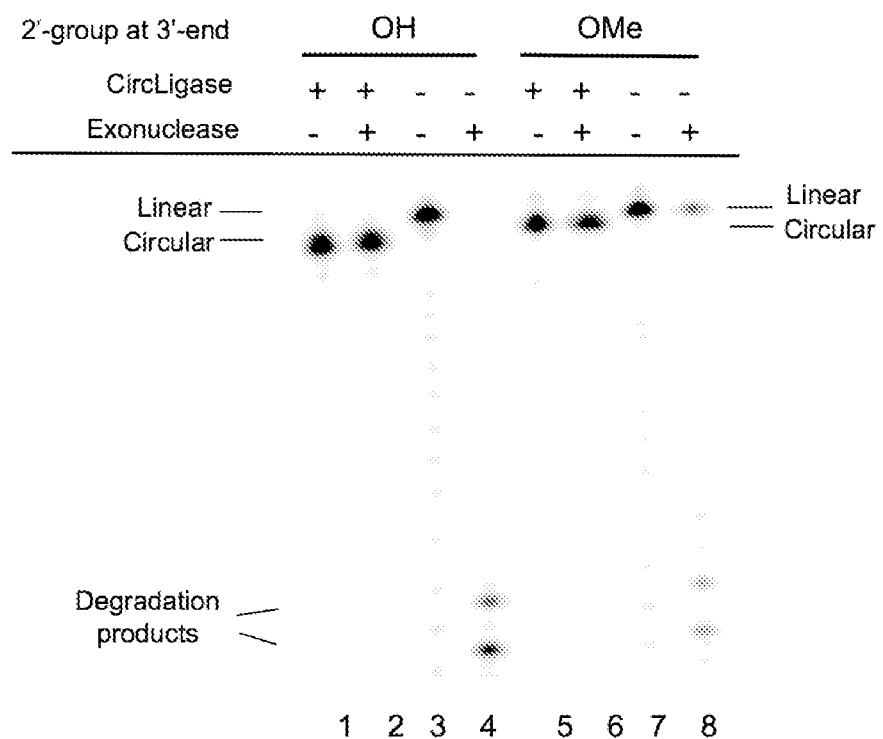

FIGURE 28C-D
C
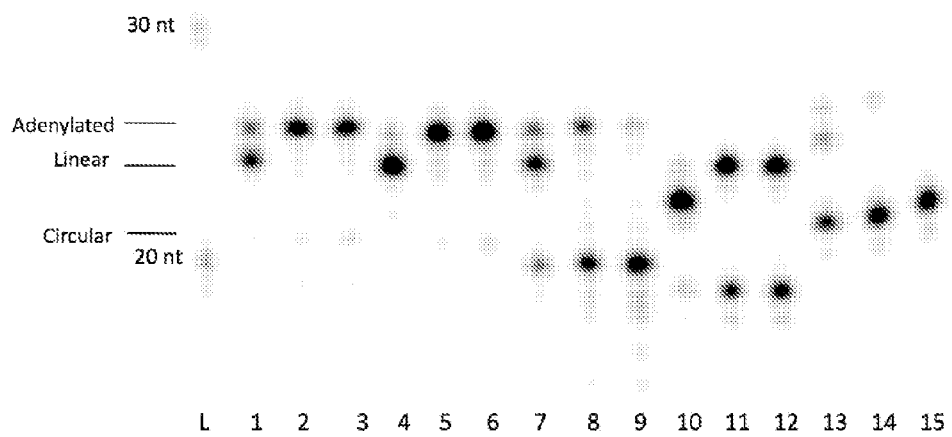
D
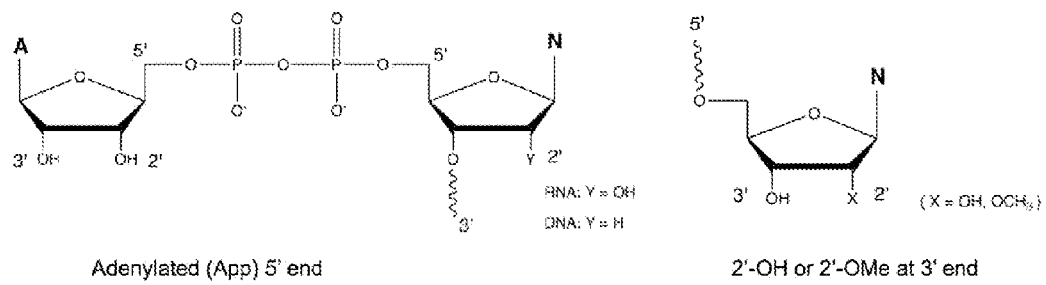
Adenylated (App) 5' end        2'-OH or 2'-OMe at 3' end

A

```
let        5'-3'
7a    UGAGGUAGUAGGUUGUAUAGUU
7b    UGAGGUAGUAGGUUGUGUGGUU
7c    UGAGGUAGUAGGUUGUAUGGUU
7d    AGAGGUAGUAGGUUGCAUAGU
7e    UGAGGUAGGAGGUUGUAUAGU
```

B

FIGURE 34
A
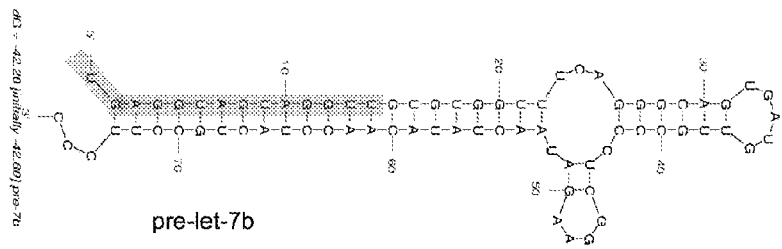
B
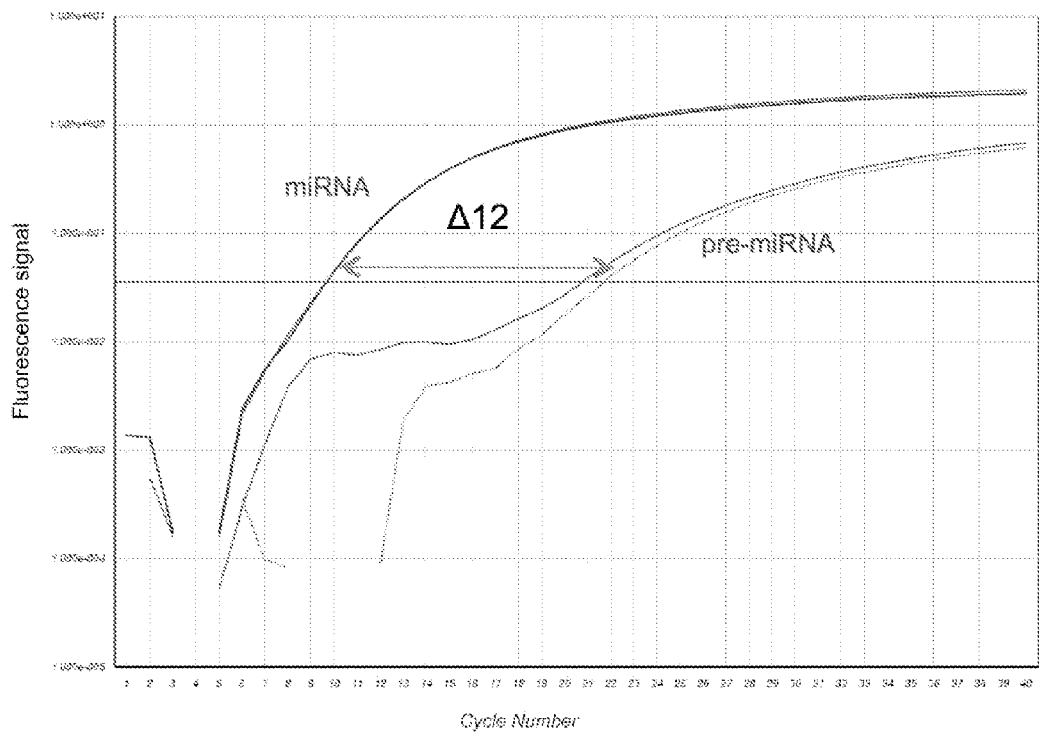

FIGURE 36A
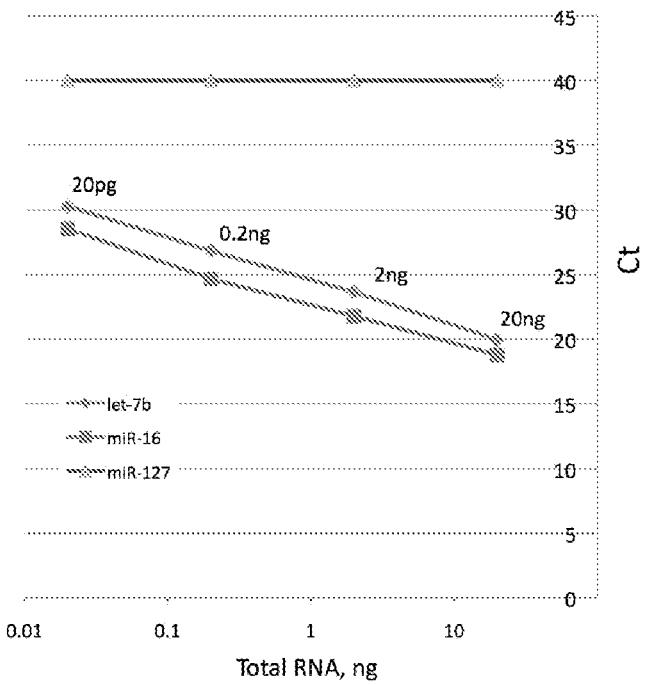
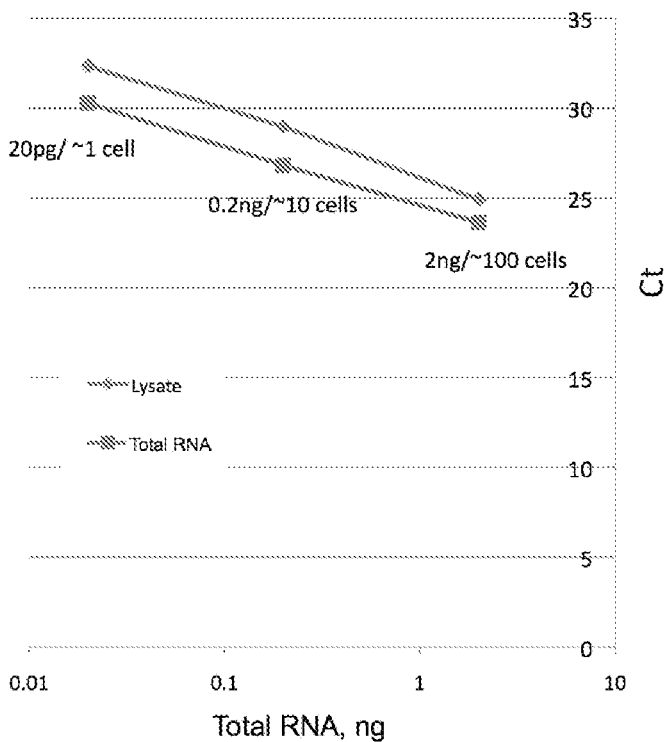

FIGURES 37

Expression profiles of selected miRNAs in total RNA extracted from various mouse tissues detected by miR-ID

| Tissue<br>miRNA | Brain | Heart | Liver | Lung | Thymus | Ovary | Embryo |
|---|---|---|---|---|---|---|---|
| let-7a | 1.4 | 3.54 | 1.00 | 3.96 | 0.65 | 0.86 | 1.42 |
| miR-16 | 1.7 | 6.88 | 1.00 | 6.54 | 4.28 | 0.97 | 1.29 |
| miR-20 | 0.28 | 2.72 | 1.00 | 6.06 | 11.42 | 2.77 | 9.67 |
| miR-21 | 0.11 | 0.87 | 1.00 | 1.28 | 0.25 | 0.40 | 0.20 |
| miR-22 | 0.84 | 5.44 | 1.00 | 1.87 | 0.1 | 0.42 | 0.24 |

FIGURE 39

Enzymatic conversion of small RNA termini into the form detectable by miR-ID

| Original, non-ligatable RNA ends | RNA modifying Enzyme (s) | Ligatable RNA ends |
|---|---|---|
| 5'-cap: 5'-m7Gppp/ 3'-OH | Tobacco Acid Pyrophosphatase (TAP) | 5'-p / 3'-OH |
| 5'-triphosphate: 5'-ppp / 3'-OH | RNA 5' Polyphosphatase | 5'-p / 3'-OH |
| 2',3'-cyclic phosphate: 5'-p / 2',3'>p | Polynucleotide Kinase (PNK) | 5'-p / 3'-OH |
| 2',3'-cyclic phosphate: 5'-OH / 2',3'>p | Polynucleotide Kinase (PNK) + ATP | 5'-p / 3'-OH |
| 2', 3'-phosphate: 5'-OH / 2'-p <br> 5'-OH / 3'-p | Polynucleotide Kinase (PNK) + ATP | 5'-p / 3'-OH |

A

SEQUENCE LISTING

```
<160> NUMBER OF SEQ ID NOS: 89

<210> SEQ ID NO 1
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 1
ucccugagac cucaagugug a                                                    21

<210> SEQ ID NO 2
<211> LENGTH: 22
<212> TYPE: RNA
<213> ORGANISM: Artificial Sequence
<220> FEATURE:
<223> OTHER INFORMATION: synthetic oligonucleotide

<400> SEQUENCE: 2
ugagguagua gguuguauag uu                                                   22

<210> SEQ ID NO 3
<211> LENGTH: 22
<212> TYPE: RNA
<213> ORGANISM: Artificial Sequence
<220> FEATURE:
<223> OTHER INFORMATION: synthetic oligonucleotide

<400> SEQUENCE: 3
ugagguagua gguugugugg uu                                                   22
```

```
<210> SEQ ID NO 4
<211> LENGTH: 22
<212> TYPE: RNA
<213> ORGANISM: Artificial Sequence
<220> FEATURE:
<223> OTHER INFORMATION: synthetic oligonucleotide

<400> SEQUENCE: 4
ugagguagua gguuguaugg uu                                              22

<210> SEQ ID NO 5
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 5
agagguagua gguugcauag u                                               21

<210> SEQ ID NO 6
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 6
ugagguagga gguuguauag u                                               21

<210> SEQ ID NO 7
<211> LENGTH: 22
<212> TYPE: RNA
<213> ORGANISM: Artificial Sequence
<220> FEATURE:
<223> OTHER INFORMATION: synthetic oligonucleotide

<400> SEQUENCE: 7
ugcgguagua guuguacag ua                                               22

<210> SEQ ID NO 8
<211> LENGTH: 22
<212> TYPE: RNA
<213> ORGANISM: Artificial Sequence
<220> FEATURE:
<223> OTHER INFORMATION: synthetic oligonucleotide

<400> SEQUENCE: 8
uagcagcacg uaaauauugg cg                                              22

<210> SEQ ID NO 9
<211> LENGTH: 23
<212> TYPE: RNA
<213> ORGANISM: Artificial Sequence
<220> FEATURE:
<223> OTHER INFORMATION: synthetic oligonucleotide

<400> SEQUENCE: 9
uaaagugcuu auagugcagg uag                                             23

<210> SEQ ID NO 10
<211> LENGTH: 22
<212> TYPE: RNA
<213> ORGANISM: Artificial Sequence
<220> FEATURE:
```

<223> OTHER INFORMATION: synthetic oligonucleotide

<400> SEQUENCE: 10
uagcuuauca gacugauguu ga                                              22

<210> SEQ ID NO 11
<211> LENGTH: 22
<212> TYPE: RNA
<213> ORGANISM: Artificial Sequence
<220> FEATURE:
<223> OTHER INFORMATION: synthetic oligonucleotide

<400> SEQUENCE: 11
aagcugccag uugaagaacu gu                                              22

<210> SEQ ID NO 12
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 12
aucacauugc cagggauuuc c                                               21

<210> SEQ ID NO 13
<211> LENGTH: 22
<212> TYPE: RNA
<213> ORGANISM: Artificial Sequence
<220> FEATURE:
<223> OTHER INFORMATION: synthetic oligonucleotide

<400> SEQUENCE: 13
ucggauccgu cugagcuugg cu                                              22

<210> SEQ ID NO 14
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 14
ugauugagcc gcgccaauau c                                               21

<210> SEQ ID NO 15
<211> LENGTH: 23
<212> TYPE: RNA
<213> ORGANISM: Artificial Sequence
<220> FEATURE:
<223> OTHER INFORMATION: synthetic oligonucleotide

<400> SEQUENCE: 15
agcuacauug ucugcugggu uuc                                             23

<210> SEQ ID NO 16
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 16
ugagguuuag gauucgugc                                                  19

-continued

<210> SEQ ID NO 17
<211> LENGTH: 37
<212> TYPE: RNA
<213> ORGANISM: Artificial Sequence
<220> FEATURE:
<223> OTHER INFORMATION: synthetic oligonucleotide

<400> SEQUENCE: 17
ugagguagua gguugugugg uuucagggca gugaugu                    37

<210> SEQ ID NO 18
<211> LENGTH: 38
<212> TYPE: RNA
<213> ORGANISM: Artificial Sequence
<220> FEATURE:
<223> OTHER INFORMATION: synthetic oligonucleotide

<400> SEQUENCE: 18
ugccccucgg aagauaacua uacaaccuac ugccuucc                   38

<210> SEQ ID NO 19
<211> LENGTH: 10
<212> TYPE: DNA
<213> ORGANISM: Artificial Sequence
<220> FEATURE:
<223> OTHER INFORMATION: synthetic oligonucleotide

<400> SEQUENCE: 19
gtctcaggga                                                  10

<210> SEQ ID NO 20
<211> LENGTH: 12
<212> TYPE: DNA
<213> ORGANISM: Artificial Sequence
<220> FEATURE:
<223> OTHER INFORMATION: synthetic oligonucleotide

<400> SEQUENCE: 20
tctcagggat ca                                               12

<210> SEQ ID NO 21
<211> LENGTH: 10
<212> TYPE: DNA
<213> ORGANISM: Artificial Sequence
<220> FEATURE:
<223> OTHER INFORMATION: synthetic oligonucleotide

<400> SEQUENCE: 21
ctactacctc                                                  10

<210> SEQ ID NO 22
<211> LENGTH: 10
<212> TYPE: DNA
<213> ORGANISM: Artificial Sequence
<220> FEATURE:
<223> OTHER INFORMATION: synthetic oligonucleotide

<400> SEQUENCE: 22
ctcaaaccac                                                  10

<210> SEQ ID NO 23
<211> LENGTH: 10
<212> TYPE: DNA
<213> ORGANISM: Artificial Sequence
<220> FEATURE:
<223> OTHER INFORMATION: synthetic oligonucleotide

```
<400> SEQUENCE: 23
cacaacctac                                                              10

<210> SEQ ID NO 24
<211> LENGTH: 12
<212> TYPE: DNA
<213> ORGANISM: Artificial Sequence
<220> FEATURE:
<223> OTHER INFORMATION: synthetic oligonucleotide

<400> SEQUENCE: 24
cacacaacct ac                                                           12

<210> SEQ ID NO 25
<211> LENGTH: 14
<212> TYPE: DNA
<213> ORGANISM: Artificial Sequence
<220> FEATURE:
<223> OTHER INFORMATION: synthetic oligonucleotide

<400> SEQUENCE: 25
accacacaac ctac                                                         14

<210> SEQ ID NO 26
<211> LENGTH: 10
<212> TYPE: DNA
<213> ORGANISM: Artificial Sequence
<220> FEATURE:
<223> OTHER INFORMATION: synthetic oligonucleotide

<400> SEQUENCE: 26
ctcctacctc                                                              10

<210> SEQ ID NO 27
<211> LENGTH: 10
<212> TYPE: DNA
<213> ORGANISM: Artificial Sequence
<220> FEATURE:
<223> OTHER INFORMATION: synthetic oligonucleotide

<400> SEQUENCE: 27
cgtgctgcta                                                              10

<210> SEQ ID NO 28
<211> LENGTH: 13
<212> TYPE: DNA
<213> ORGANISM: Artificial Sequence
<220> FEATURE:
<223> OTHER INFORMATION: synthetic oligonucleotide

<400> SEQUENCE: 28
cactataagc act                                                          13

<210> SEQ ID NO 29
<211> LENGTH: 13
<212> TYPE: DNA
<213> ORGANISM: Artificial Sequence
<220> FEATURE:
<223> OTHER INFORMATION: synthetic oligonucleotide

<400> SEQUENCE: 29
agtctgataa gct                                                          13

<210> SEQ ID NO 30
<211> LENGTH: 10
```

```
<212> TYPE: DNA
<213> ORGANISM: Artificial Sequence
<220> FEATURE:
<223> OTHER INFORMATION: synthetic oligonucleotide

<400> SEQUENCE: 30
ctggcagctt                                                              10

<210> SEQ ID NO 31
<211> LENGTH: 11
<212> TYPE: DNA
<213> ORGANISM: Artificial Sequence
<220> FEATURE:
<223> OTHER INFORMATION: synthetic oligonucleotide

<400> SEQUENCE: 31
ggcaatgtga t                                                            11

<210> SEQ ID NO 32
<211> LENGTH: 9
<212> TYPE: DNA
<213> ORGANISM: Artificial Sequence
<220> FEATURE:
<223> OTHER INFORMATION: synthetic oligonucleotide

<400> SEQUENCE: 32 agacggatc                                                                9

<210> SEQ ID NO 33
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 33
caagctcaga cggatccga                                                    19

<210> SEQ ID NO 34
<211> LENGTH: 10
<212> TYPE: DNA
<213> ORGANISM: Artificial Sequence
<220> FEATURE:
<223> OTHER INFORMATION: synthetic oligonucleotide

<400> SEQUENCE: 34
ggctcaatca                                                              10

<210> SEQ ID NO 35
<211> LENGTH: 12
<212> TYPE: DNA
<213> ORGANISM: Artificial Sequence
<220> FEATURE:
<223> OTHER INFORMATION: synthetic oligonucleotide

<400> SEQUENCE: 35
cagttccaaa ag                                                           12

<210> SEQ ID NO 36
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 36
```

```
ctcaagtgtg atccctgag                                                    19
```

<210> SEQ ID NO 37
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 37

```
agggatcaca cttgaggtc                                                    19
```

<210> SEQ ID NO 38
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 38

```
gctgcgatcg atggtcaggt cctgagtgtg atccctgaga cct                         43
```

<210> SEQ ID NO 39
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 39

```
gctgcgatcg atggtcaggt gctgtctcag ggatcacact tga                         43
```

<210> SEQ ID NO 40
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 40

```
caggacctga ccatcgatcg cagc                                              24
```

<210> SEQ ID NO 41
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 41

```
gaggtagtag gttgtata                                                     18
```

<210> SEQ ID NO 42
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 42

```
acaacctact acctcaaa                                                     18
```

<210> SEQ ID NO 43
<211> LENGTH: 18
<212> TYPE: DNA
<213> ORGANISM: Artificial Sequence

```
<220> FEATURE:
<223> OTHER INFORMATION: synthetic oligonucleotide

<400> SEQUENCE: 43
ggtagtaggt tgtgtggt                                                 18

<210> SEQ ID NO 44
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 44
acacaaccta ctacctca                                                 18

<210> SEQ ID NO 45
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 45
gaccaccttg cgatcgggta cagcctacta cctca                              35

<210> SEQ ID NO 46
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 46
tgcgggtaca gcacctacct tgcggttgtg tggtt                              35

<210> SEQ ID NO 47
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 47
gtttgaggta gtaggttgtg                                               20

<210> SEQ ID NO 48
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 48
aacctactac ctcaaaccac                                               20

<210> SEQ ID NO 49
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 49
gaggtagtag gttgtgtg                                                 18
```

```
<210> SEQ ID NO 50
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 50
acaacctact acctcaaa                                                  18

<210> SEQ ID NO 51
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 51
gaggtagtag gttgtatg                                                  18

<210> SEQ ID NO 52
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 52
acaacctact acctcaaa                                                  18

<210> SEQ ID NO 53
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 53
gtagaggtag taggttgc                                                  18

<210> SEQ ID NO 54
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 54
acctactacc tctactat                                                  18

<210> SEQ ID NO 55
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 55
ttgtatagtt gaggtagg                                                  18

<210> SEQ ID NO 56
<211> LENGTH: 18
<212> TYPE: DNA
<213> ORGANISM: Artificial Sequence
<220> FEATURE:
<223> OTHER INFORMATION: synthetic oligonucleotide
```

```
<400> SEQUENCE: 56
acctcaacta tacaacct                                                18

<210> SEQ ID NO 57
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 57
gaggtagtag tttgtacagt a                                            21

<210> SEQ ID NO 58
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 58
tgtacaaact actacctcat a                                            21

<210> SEQ ID NO 59
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 59
agcacgtaaa tattggcg                                                18

<210> SEQ ID NO 60
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 60
ccaatattta cgtgctgc                                                18

<210> SEQ ID NO 61
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 61
gcaggtagta aagtgcttat                                              20

<210> SEQ ID NO 62
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 62
agcactttac tacctgcact                                              20

<210> SEQ ID NO 63
```

```
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 63
gatgttgata gcttatcaga c                                          21

<210> SEQ ID NO 64
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 64
tgataagcta tcaacatcag t                                          21

<210> SEQ ID NO 65
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 65
ctgcctgttg aagaact                                               17

<210> SEQ ID NO 66
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 66
ttcttcaact ggcagct                                               17

<210> SEQ ID NO 67
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 67
tcacattgcc agggat                                                16

<210> SEQ ID NO 68
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 68
cctggcaatg tgatgg                                                16

<210> SEQ ID NO 69
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 69
```

```
gatccgtctg agcttggct                                                   19

<210> SEQ ID NO 70
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 70
caagctcaga cggatccga                                                   19

<210> SEQ ID NO 71
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 71
ccgcgccaat atctga                                                      16

<210> SEQ ID NO 72
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 72
gatattggcg cggctc                                                      16

<210> SEQ ID NO 73
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 73
aaaaattcgt cactaccact g                                                21

<210> SEQ ID NO 74
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 74
tggtagtgac gaattttttgt t                                               21

<210> SEQ ID NO 75
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 75
gaccaccttg cgatcgggta cagc                                             24

<210> SEQ ID NO 76
<211> LENGTH: 24
<212> TYPE: DNA
```

```
<213> ORGANISM: Artificial Sequence
<220> FEATURE:
<223> OTHER INFORMATION: synthetic oligonucleotide

<400> SEQUENCE: 76
tgcgggtaca gcacctacct tgcg                                          24

<210> SEQ ID NO 77
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 77
ctcaagtgtg atccctgaga c                                             21

<210> SEQ ID NO 78
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 78
tcagggatca cacttgaggt c                                             21

<210> SEQ ID NO 79
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 79
tttgaggtag taggttgtat a                                             21

<210> SEQ ID NO 80
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 80
acaacctact acctcaaact a                                             21

<210> SEQ ID NO 81
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 81
tttgaggtag taggttgtgt g                                             21

<210> SEQ ID NO 82
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 82
acaacctact acctcaaacc ac                                            22
```

```
<210> SEQ ID NO 83
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 83
tttgaggtag taggttgtat g                                                 21

<210> SEQ ID NO 84
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 84
acaacctact acctcaaacc at                                                22

<210> SEQ ID NO 85
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 85
atagtagagg tagtaggttg c                                                 21

<210> SEQ ID NO 86
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 86
acctactacc tctactatgc a                                                 21

<210> SEQ ID NO 87
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 87
aggttgtata gttgaggtag g                                                 21

<210> SEQ ID NO 88
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 88
acctcaacta tacaacctcc t                                                 21

<210> SEQ ID NO 89
<211> LENGTH: 17
<212> TYPE: DNA
<213> ORGANISM: Artificial Sequence
<220> FEATURE:
```

```
<223> OTHER INFORMATION: synthetic oligonucleotide
<221> NAME/KEY: modified_base
<222> LOCATION: 1
<223> OTHER INFORMATION: adenylated
<221> NAME/KEY: modified_base
<222> LOCATION: 17
<223> OTHER INFORMATION: dideoxycytidine

<400> SEQUENCE: 89
ctgtaggcac catcaat                                                  17
```

METHODS AND COMPOSITIONS FOR DETECTION OF SMALL RNAS

CROSS REFERENCE

This application is the National Phase entry of International Application No. PCT/US2010/030922, filed Apr. 13, 2010, which claims the benefit of priority of U.S. Provisional Application No. 61/168,887, filed on Apr. 13, 2009, the contents of each are incorporated by reference herein in their entireties.

GOVERNMENT SUPPORT

This invention was made with government support under Small Business Innovation Research grant 1R43CA134277-01A1 awarded by the National Institute of Health. The government has certain rights in the invention.

FIELD OF THE INVENTION

The present invention is in the field of molecular cell biology. More specifically, it concerns methods and compositions that find use in the identification, detection, quantification, expression profiling and stability of small RNAs, both naturally occurring and man-made. The present invention finds use in a variety of genomic research and diagnostic applications, including medical, agricultural, food and biodefense fields. The RNA(s) of interest may represent biomarker(s) indicating infection such as viral and bacterial, or other diseases such as cancer, genetic and metabolic disorders.

BACKGROUND AND RELATED ART

The discovery of microRNAs (miRNAs) and other short non-coding RNAs (such as siRNA, piRNA, and snRNA) has led to a rapid expansion of research elucidating their expression and diverse biological functions. These functions include regulation of development, cell proliferation, differentiation, and the cell cycle as well as translation or stability of target mRNAs (Zamore & Haley 2005; Bushati & Cohen 2007). The DNA sequences encoding miRNAs are transcribed by RNA polymerase II as long pri-miRNAs that are processed, first by Drosha into pre-miRNA (70-90 nt) and then by Dicer to yield mature miRNAs consisting of 21-22 nt single strands (Bartel 2004; Zamore & Haley 2005; Kim & Nam 2006). Hundreds of miRNAs have been identified, which may cooperatively regulate greater than one-third of all human genes (Lewis et al. 2005; Lim et al. 2005; Kim & Nam 2006). Recent studies have shown that distinct miRNA expression patterns are associated with various types of cancer (Lu et al. 2005a; Cummins & Velculescu 2006; Esquela-Kerscher & Slack 2006; Hammond 2006a; Pfeffer & Voinnet 2006; Hernando et al. 2007; Wu et al. 2007) and viral infections (Cullen 2006; Dykxhoorn 2007; Pan et al. 2007). Thus, miRNAs may be considered as potential diagnostic biomarkers as well as potential drug targets for antisense agents (Hutvagner et al. 2004; Meister et al. 2004; Krutzfeldt et al. 2005; Davis et al. 2006; Hammond 2006b; Orom et al. 2006; Weiler et al. 2006; Zhang & Farwell 2008).

In most cases, expression levels of many different miRNA species (rather than a single miRNA) are changed in the course of disease, and therefore should be assayed simultaneously for monitoring progression of the disease and response to therapy. For example 27 human miRNAs are either down-regulated (let-7a, let-7b, let-7c, let-7d, let-7g, miR-16, miR-23a, miR-23b, miR-26a, miR-92, miR-99a, miR-103, miR-125a, miR-125b, miR-143, miR-145, miR-195, miR-16, mir199a, miR-221, miR-222, miR-497) or up-regulated (miR-202, miR-210, miR-296, miR-320, miR-370, mir498, miR-503) in prostate carcinoma (Mattie et al. 2006; Porkka et al. 2007). Cancer biopsies are often formalin fixed, which is incompatible with mRNA isolation and analysis due to the RNA-protein cross-links, covalent modifications and degradation of long RNA that occur during the fixation process. However, short miRNAs have significant advantages as biomarkers because they are much less affected by such modifications (Li et al. 2007; Xi et al. 2007).

It is commonly expected that many more naturally occurring small RNAs are still to be discovered. Once identified and validated as biomarkers and/or therapeutic targets, specific miRNA(s) require sensitive and accurate detection and quantification in biological and clinical samples. The copy number of individual miRNAs may vary from less than 10 to about 50,000 per cell, and their expression profiles vary with the age, health and treatment of cells and where they are in the cell cycle (Chen et al. 2005; Ahmed 2007). A variety of methods for measuring the levels of known miRNAs have been already developed, including but not limited to: Northern blots (Valoczi et al. 2004; Aravin & Tuschl 2005; Ramkissoon et al. 2006; Pall et al. 2007); nuclease-protection (Lee et al. 2002; Overhoff et al. 2004; Aravin & Tuschl 2005; Winkler et al. 2006); DNA primer-extension (Seitz et al. 2004; Sioud & Rosok 2004); sandwich hybridization assays using ELISA and DNA dendrimers (Barad et al. 2004; Lu et al. 2005a; Mora & Getta 2006); direct labeling of miRNAs and hybridization to slide or bead arrays (Krichevsky et al. 2003; Babak et al. 2004; Barad et al. 2004; Calin et al. 2004; Liu et al. 2004; Nelson et al. 2004; Shingara et al. 2005; Yeung et al. 2005; Xia 2006; Gottwein et al. 2007; Tang et al. 2007; Wang et al. 2007); pre-amplification and labeling of target sequences and hybridization to slide or bead arrays (Saba & Booth 2006; Mattie et al. 2006); RT-PCR with TaqMan detection probes (Chen et al. 2005; Jiang et al. 2005; Jacobsen et al. 2005; Lu et al. 2005b; Raymond et al. 2005; Winkler et al. 2006); ligation-assisted PCR wherein miRNA serves as a ligation splint (Brandis et al. 2006; Sorge & Mullinax 2006; Maroney et al. 2007; Chamnongpol & Souret 2008), the Invader assay (Allawi et al. 2004); rolling circle amplification (RCA) of target-specific padlock probes (Jonstrup et al. 2006; Van Huffel 2006); and single miRNA molecule detection based on hybridization with short LNA-DNA probes (Neely et al. 2006).

Many of these methods have been adapted from previously established mRNA assays with modifications that accommodate the differences between mRNA and miRNA. MicroRNAs are much smaller than mRNAs and are neither capped nor polyadenylated. These characteristics make it hard to isolate a pure fraction of miRNAs, limit the number of labels that can be chemically or enzymatically introduced into miRNA molecules, and disallow the use of standard PCR primers (see below).

Northern hybridization of miRNA targets with labeled oligonucleotide probes is still considered as the "gold standard" for the simultaneous characterization of miRNAs and their longer precursors (pri- and pre-miRNAs). This method, however, is inadequate for a number of reasons. First, short unmodified RNAs cannot be efficiently cross-linked to support membranes used in nucleic acid hybridization assays. Second, even when cross linking occurs there is significant variability dependent on the number of U residues present; and third, cross-linked species have reduced ability to hybridize with probes (Valoczi et al. 2004; Pall et al. 2007). Two other methods that rely on gel-electrophoresis techniques are:

nuclease-protection of labeled DNA or probes, which are usually longer than target miRNA targets; and reverse-transcription extension of primers, which are usually shorter than miRNA targets. The major limitations of all three of these methods are poor sensitivity, preventing detection of low-copy miRNAs, and low throughput and multiplexing capabilities.

Some other methods of miRNA detection employ direct chemical or enzymatic modification of the RNAs (Wark et al. 2008). For example, platinum (Babak et al. 2004) and alkylating (Enos et al. 2007) agents that preferentially bind purine bases (G>A) are used for chemical labeling of miRNAs. Drawbacks of these approaches include: (1) efficacy of labeling depends on number and position of the purine bases, which vary for different miRNA species; (2) the number of introduced labels into the same miRNA species may vary; and (3) these modifications may reduce the affinity of the miRNA for probes (Ahmed 2007). Alternatively, modification of miRNAs can be made through oxidation of the 2',3'-diol on their 3' termini (Liang et al. 2005; Beuvink et al. 2007), but it is a laborious, multi-step procedure and also causes partial degradation of the RNA.

Enzymatic approaches applied to miRNA modification involve either RNA or DNA ligases. miRNA labeling methods usually involve derivatives of pCp and T4 RNA ligase (Cameron & Uhlenbeck 1977) and their efficiency varies depending on last few nucleotides located at the 3' end of the miRNA (Cao 2004; Esquela-Kerscher & Slack 2004; Nelson et al. 2004; Enos et al. 2007; Wang et al. 2007). Moreover, T4 RNA ligase tends to circularize small RNAs naturally carrying 5'-p and 3'-OH, including miRNAs (Aravin & Tuschl 2005; Nichols et al. 2008). The RNA circularization prevents 3'-end labeling or adapter attachment (another approach involving T4 RNA ligase), and, therefore, makes the majority of small RNA undetectable by current ligation-based methods. To prevent circularization, the 5'-p ends of RNAs must be dephosphorylated. The application of T4 RNA ligase for attachment of adapter or linkers to small RNA does not require prior knowledge of the RNA sequence and, therefore, is used mostly for discovery of new small RNAs. For this purpose, universal linkers are attached at each end of small RNAs followed by conventional PCR amplification, cloning, and sequencing (Aravin & Tuschl 2005; Pfeffer et al. 2005; Cummins et al. 2006; Michael 2006). A similar approach was also applied for expression profiling of miRNAs, wherein asymmetric PCR was used after conventional PCR and the resulting single-stranded PCR products were hybridized to target-specific oligonucleotide probes attached to color-coded beads (Lu et al. 2005a).

Splint-assisted ligation by T4 DNA ligase is an alternative strategy for the attachment of adapter oligonucleotides to target RNA. This reaction is not very efficient for ligation of RNA (rather than DNA) between the 3'-OH and 5'-p ends and its efficiency depends on the sequence near the ends to be ligated (Moore & Query 2000). Hence the use of ligases to label miRNAs may lead to biased representations of the different miRNAs species. Similar to T4 DNA ligase, T4 RNA ligase 2 ligates RNA and DNA ends but in both splint-assisted and splint-independent manners (Ho & Shuman 2004; Nandakumar & Shuman 2004; Nichols et al. 2008). Another commonly used enzymatic technique is polyadenylation of miRNAs at their 3' ends (Aravin & Tuschl 2005; Shi & Chiang 2005; Ahmed 2007; Wark et al. 2008), which allows the use a DNA polymerase primer extension with oligo(dT)-primers. This technique is of limited value, however, because polyadenylation-based assays cannot detect all miRNA species (Enos et al. 2007). Both sequence and structure of the RNA may affect the poly(A) polymerase processivity (Yehudai-Resheff et al. 2000). Moreover, poly(A) polymerase cannot extend RNAs having a 2'-OMe modification on their 3' terminal nucleotides (Ebhardt et al. 2005; Yang et al. 2006) and, therefore, polyadenylation cannot be currently used for detection of such RNAs (Enos et al. 2007). Although the 2'-OMe modification is not typical for animal miRNAs, this modification is common for plant siRNAs and miRNAs as well as for piRNAs from *Drosophila* and animals (Li et al. 2005; Yu et al. 2005; Aravin et al. 2007; Horwich et al. 2007; Yang et al. 2007).

RNAs are known to serve as primers for nucleic acid polymerization. A variety of DNA polymerases, reverse transcriptases and mutated RNA polymerases can catalyze the polymerization of DNA using RNA primers with both DNA and RNA templates. For example, the Klenow fragment of DNA polymerase I has been used for the selective labeling and detection of specific RNAs in a mixture (Huang & Szostak 1996, 2003; Huang & Alsaidi 2003). RNA-primed array-based Klenow enzyme assays (RAKE) have been used for labeling (during primer extension) and detection of miRNAs by hybridization to DNA capture probes attached either to microarray slides (Nelson et al. 2004; Yeung et al. 2005; Berezikov et al. 2006; Getts et al. 2006; Genisphere 2007) or beads (Jacobsen et al. 2005). Also, the ability of miRNAs to serve as primers was employed for miRNA detection in vitro using circular DNA probes and RCA (Jonstrup et al. 2006; Van Huffel 2006) as well as for detection of miRNA in situ using ultramer DNA probes (Nuovo et al. 2009). Finally, RNA-dependent extension of the miRNA by both DNA (reverse transcriptase) and RNA (RdRp) polymerases has been used for identification of mRNA sequences targeted by these miRNAs by (Rana 2004; Vatolin et al. 2006).

Target RNA can serve as a template for RT-PCR. The major problem for direct RT-PCR of small RNAs is related to their size—at only 20-27 nt, they are nearly the same size as an ordinary PCR primer while two primers are required for exponential amplification. For this reason, the first RT-PCR assays were developed for miRNA precursors, which are more than twice as long as mature miRNAs (Schmittgen et al. 2004; Jiang et al. 2005). This methodology, however, may not lead to accurate representation of the biologically relevant profile, because levels of the precursors do not always correlate with those of the mature miRNAs due to the rapid processing of the miRNA precursors and the longevity of active miRNAs associated with the RISC complex (Bartel 2004; Jiang et al. 2005; Lao et al. 2007).

One approach for amplifying miRNA relies on having only a short overlap between primer and miRNA sequences (Chen et al. 2005; Raymond et al. 2005; Raymond 2007; Sharbati-Tehrani et al. 2008; Sharbati-Tehrani & Einspanier 2008). Unfortunately, ordinary short RT-PCR primers fail to hybridize stably at the temperatures needed for the PCR extension step. Moreover, miRNA sequences differ significantly in GC-content, both among different miRNA species (in the range 24 to 73% GC) and between the 5' and 3' halves of individual miRNAs (Hammond 2006c). As a result, primers binding to different miRNAs would not be equally effective under given conditions, compromising both sequence-specificity and efficacy of the PCR amplification (Esquela-Kerscher & Slack 2004; Winkler et al. 2006). An additional problem is the difficulty of distinguishing minor differences in sequence and/or length between different miRNA isoforms (Sioud & Rosok 2004; Hammond 2006c). To address these problems, extended target-specific primers forming short but stable duplexes with the 3' ends of miRNAs have been used by three groups. One group used stem-and-loop RT primers having only 6 nt complementary to the 3' end of target miRNAs along with two more PCR primers, wherein one primer was corresponding to the 5'-end of target sequence and another primer was corresponding to the stem-and-loop sequence, and Taq-Man probes (Chen et al. 2005). The second group used combo RT primers, which comprised 7-12 nt complementary to the 3' end of target miRNAs and an additional sequence encoding sequence for second PCR primer, along with two more PCR primers, wherein one LNA-DNA primer corresponded to the 5'-end of target sequence and the other primer corresponded to the additional sequence (Raymond et al. 2005; Raymond 2007). And third group used similar combo RT primers (but without LNA modifications) along with three additional PCR primers, wherein one PCR primer corresponding to the 5'-end of target sequence was the combo primer and other two primers corresponded to the additional sequences of the combo primers (Sharbati-Tehrani et al. 2008; Sharbati-Tehrani & Einspanier 2008).

A second approach for assaying short mature miRNA by RT-PCR is the extension of short target sequences (miRNA or complementary cDNAs) either by polyadenylation (Shi & Chiang 2005; Illumina 2007; Kreutz et al. 2007), or ligation of adapter oligonucleotides (Lu et al. 2005b; Dawson & Womble 2006; Mishima et al. 2007).

Simultaneous amplification of many target sequences in one reaction under the same conditions (multiplex PCR) could increase assay throughput and allow the use of smaller samples. However, reported multiplex PCR reactions are restricted to amplification of five to ten targets (Broude et al., 2001). The reasons for this are that conventional PCR primers specific to different targets tend to form dead-end dimers when mixed and extended together, and there is also increased cross-hybridization of primers with non-target sequences (Brownie et al. 1997). As a result, primer design for multiplex PCR is not a trivial task, requiring tedious optimization of PCR conditions and it still often fails—especially for short RNA targets with high variation of GC-contents such as miRNAs. There is an added technological challenge because of overlap in the emission spectra of available fluorescent dyes. Currently at most six dyes can be assayed simultaneously within the same sample. One approach to achieve uniform multiplex PCR amplification is using combo primers, wherein each combo primer combines different pairs of target-specific sequence and an additional Zip-code sequence. PCR with combo primers is usually performed in two rounds of amplification: the first round is performed with a relatively low concentration of the combo primers while the second round uses a high concentration of shorter primers comprising only the Zip-code sequences. A wide variety of 20-27 nt Zip-code or functionally similar sequences can be associated with (designated to) targets of interest (Gerry et al. 1999; Ye et al. 2001; Fan et al. 2000; Hirschhorn et al. 2000). Such sequences share several common features: (1) they are designed to be unique, not represented in the sample to be tested; (2) have similar $T_m$ so that annealing and extension can be performed under the same stringent condition; and (3) do not cross-hybridize to each other or to another or nucleic acids that can be present in a sample (Shoemaker et al. 2006; Smith et al. 2001; Shuber et al. 2005; Lin et al. 2006; Pinto et al. 2006).

RNA size and sequence play key roles in any RNA detection method relying on a sequence-specific binding (hybridization) of target RNAs either with substantially complementary capture probes or primers. The differences in thermostability between perfect and mismatched duplexes depend on length and sequence as well as the type and position of mismatches. The trade-off between high affinity for the target and low sequence-specificity of binding is a major limitation for designing allele-specific hybridization probes and multiplex probes targeting sequences with different GC-content (Toulme et al. 2001; Demidov & Frank-Kamenetskii 2004). Increasing the affinity of these agents to their intended targets simultaneously decreases their selectivity. Hybridization and primer-extension assays dealing with individual sequences can be optimized for maximum selectivity by adjusting temperature, incubation time, salt, and formamide concentration in the hybridization and washing steps. However, multiplexing assays, in which multiple probe-target hybridizations are conducted simultaneously under the same conditions, lack this customizing option. There are so-called stringency elements known in art that can improve sequence-specificity of hybridization probes and primers including: (1) modified nucleotides (e.g. LNA), which provide higher affinity to AT-rich sequences, placed into specific positions in the probe/primer sequence (Braasch et al. 2002; Valoczi et al. 2004; Fluiter et al. 2005); (2) dividing of probes/primers into smaller fragments that are complementary to adjacent sites in target RNA (Maher & Dolnick 1988; Kandimalla et al. 1995; Wang et al. 2003); (3) stem-loop (hairpin) structures with short single-stranded overhangs complementary to the target 3'-end, which enhance stability through contiguous stacking interactions between the probe and target ends (Lane et al. 1998; Chen et al., 2005; Wang et al. 2007); (4) partially double-stranded probe/primers that bind with target in through competitive or replacement hybridization process (Vary 1987; Li et al. 2002; Kong et al. 2004; Huang et al. 2007; Luk et al. 2007); (5) folding-back sequences that are complementary to one or to both ends of the probe/primer sequence (Roberts & Crothers 1991; Hertel et al. 1998; Ohmichi & Kool 2000; Bortolin & Zastawny 2007); (6) "molecular beacon"-like structures that have short complementary "arms" flanking the antisense sequence at both ends (Bonnet et al. 1999, Hartig et al. 2004; Hopkins & Woodson 2005); and (7) use of substantially complementary sequences that have few mismatches to the intended target in specific positions (Guo et al. 1997; Delihas et al. 1997; Brukner et al. 2007).

The rapidly expanding list of different proprietary methods of miRNA detection indicates that no current technology is perfect or has clear advantage over its competitors. Because RT-PCR methods have very good sensitivity, sequence specificity, and dynamic range, they are frequently used as method of choice for expression profiling of defined miRNAs as well as validating results obtained by other common methods such as microarray and northern blot assays (Ahmed 2007). However, none of these methods is particularly simple, with most requiring numerous steps that render them laborious, time consuming and expensive. Moreover, the need for cumbersome and costly temperature cycling equipment limits the wide adoption of even PCR-based methods for point-of-care diagnostic applications, an area in which isothermal amplification techniques could provide simpler and more cost-effective solutions.

Before the present invention, the circularization of small RNAs naturally carrying 5'-p and 3'-OH by T4 RNA ligase was regarded as an obstacle and explicitly avoided (Aravin & Tuschl 2005) while short lengths of small RNA targets was recognized as factor limiting the use of conventional PCR primers in current assays (Chen et al. 2005; Jiang et al. 2005). Aspects of the present invention include methods and compositions for detection of known small RNAs as well as the discovery of new small RNAs. We capitalize on the ability of small RNA targets or their conjugates with oligonucleotide adapters to be easily circularized. The circular RNA templates provide amplification of the target (and adapter) sequences via synthesis of multimer nucleic acids that can be either labeled for direct detection or subjected to PCR amplification and detection. The structure of small circular RNAs and their corresponding multimer nucleic acids provide certain advantages, including unmatched flexibility in design of conventional RT and PCR primers as well as allowing the use of overlapping dimer-primers for efficient and sequence-specific amplification of short target sequences. As compared to previously described methods, aspects of the present invention allow a reduction in the number of steps and reagents while increasing sensitivity and accuracy of detection of small RNAs with both 2'OH and 2'-OMe at their 3' ends.

SUMMARY OF THE INVENTION

Aspects of the invention include methods of detecting the presence of a known target RNA in a sample, including the steps of: a) circularization of target RNA by ligation of its 5'- and 3'-ends; b) synthesis of multimer nucleic acid (MNA) comprising multiple repeats of sequences that are complementary to the target RNA by rolling circle amplification (RCA); and c) assaying for the presence of the MNA, thereby detecting the presence of the target RNA in a sample.

In certain aspects of the invention, an adapter (or linker) is ligated to the RNA target before the circularization. In this embodiment, the invention includes the following steps: a) ligating an adapter oligonucleotide to the target RNA that yields an extended target polynucleotide (a target-adapter conjugate); b) circularization of the extended target polynucleotide by ligation of its 5'- and 3'-ends; c) synthesis of MNA comprising multiple repeats of sequences that are complementary to the target RNA and the adapter by RCA; d) assaying for the presence of the MNA, thereby detecting the presence of the target RNA in a sample.

Aspects of the invention also include methods for discovering (or identifying) an unknown RNA in a sample, including the general steps of: a) ligating an adapter (or linker) oligonucleotide to all RNA molecules present in a sample that results in extended polynucleotide library; b) circularizing each of the extended polynucleotides by ligation of its 5'- and 3'-ends; c) reverse transcription of the extended polynucleotide using a first oligonucleotide primer, which sequence is complementary to 5'-end sequence of the adapter, yielding multimer DNA strand (cDNA) comprising multiple repeats of sequences that are complementary to the target RNA and the adapter; d) PCR amplification of the cDNA sequences using the first primer and a second oligonucleotide primer, which sequence corresponds to 3'-end sequence of the adapter, yielding double-stranded DNA fragments encoding different RNA sequences flanked by the end sequences (sense and antisense) of the adapter; and e) sequencing of the DNA fragments to discover (or identify) the RNA in the sample.

In certain embodiments of the invention, a method of RNA circularization is selected from: direct ligation using an RNA ligase 1 or CircLigase; splint-assisted ligation using a DNA ligase or RNA ligase 2; and a chemical ligation. Using bacteriophage RNA ligase 1 or CircLigase are preferable methods since they are universal (not dependent on target-sequences) and allow multiplexing at the ligation/circularization step(s).

In certain embodiments of the invention, the circularization of a target RNA or extended target RNA (target-adapter conjugate) is followed by degradation of linear nucleic acids by an exonuclease or mixture of exonucleases.

In some embodiments of the invention, the target RNAs comprise the following features: a) size ranging from 10 to 100 nucleotides (nt); b) 5'-phosphate (5'-p) or other naturally existing 5'-end group such as: cap, 5'-triphosphate (5'-ppp), and 5'-hydroxyl (5'-OH) that can be converted to 5'-p before the ligation and/or circularization; c) 3'-hydroxyl (3'-OH); d) 2'-OH or 2'-OMe at the target 3'-end. In preferred embodiments, target RNAs are miRNAs and other small RNAs having lengths in the range of 19-40 nt. However, some embodiments of the invention are not limited for small RNA applications and may be equally applied for any RNA that can be circularized.

In some embodiments of the invention, the assayed samples represent extracts from biologically and clinically relevant tissues or cells and are selected from: crude nucleic acid extract; total RNA extract; fraction of small RNAs which length is limited by a method of purification.

In preferred embodiments of the invention, multiple target RNAs are simultaneously detected or discovered in the samples.

In certain embodiments of the invention, the adapter oligonucleotide comprises the following features: a) size ranging from 10 to 100 nucleotide, and preferably from 20 to 30 nucleotides, in length; b) consist of RNA, or DNA or mix of DNA and RNA residues or their chemical analogs; c) a sequence selected from: promoter for an RNA polymerase; a sequence which is not substantially complementary or corresponds to any sequence that can be present in the sample; a Zip-code sequence; a homopolynucleotide linker; and a sequence encoding one or two linkers used for cloning and sequencing (including next-generation sequencing); d) 3'-OH; e) 5'-group selected from: 5'-p and 5'-OH; f) 3'-end group selected from 3'-OH and 3'-p; g) 2'-group (at 3'-end) selected from: 2'-OH and 2'-OMe; h) attached to 3'-end of any of the RNA targets; i) attached to 5'-end of the RNA targets carrying 2'-OMe at their 3'-ends. In some embodiments of the invention, the adapter (or linker) is adenylated by incubation of corresponding non-adenylated oligonucleotide with RNA ligase 1 in the presence of ATP, wherein the oligonucleotide has 5'-p and 3' end groups are is selected from combinations: 2'-OH with 3'-p; or 2'-OMe with 3'-OH.

In some embodiments of the invention, the circularized RNA target is used as a template for rolling-circle reverse transcription (RT-RCA) that yields multimer cDNA in two steps: a) binding of a circular target RNA with an oligonucleotide RT primer; and b) enzymatic extension of the RT primer by reverse transcriptase. In certain embodiments of the invention, the RT primer is target-specific and contains a sequence that is substantially complementary to any regions of the circular target RNAs, wherein the complementary sequence is ≥6 nt in length, and, preferentially, from 8 to 18 nt in length. In certain embodiments of the invention, the RT primer is target-specific and contains a sequence, which is substantially complementary to the target RNA, wherein the complementary sequence is ≥6 nt in length. Preferentially, the 3'-ends of RT primers comprise stretches of 10 to 18 nt complementary to any parts of the circular target RNAs. In other embodiments of the invention, the RT primers are supplied as a mixture of fully or partially randomized oligonucleotide sequences ranging from 6 to 10 nt in length. In certain embodiments of the invention that are related to circular target-adapter conjugates, the universal (target-independent) RT primer is complementary to the adapter (or linker). In certain embodiments of the invention, multiple circular target RNAs get reverse transcribed simultaneously in multiplex format.

In some embodiments of the invention, the circularized RNA target or target-adapter conjugate is used as a template for transcription that yields multimer cRNA. The method of the transcription is selected from: a) promoter-less, which is preferred for circular RNA of 19-40 nt; and b) promoter-dependent, which is preferred for target-adapter conjugate of ≥40 nt (total length). In the latter embodiments, the cRNA is synthesized in two steps: a) binding (or annealing) an oligo-deoxynucleotide comprising one strand of a double stranded promoter for appropriate RNA polymerase (e.g., T7 or T3) to a circular extended polynucleotide that encodes the second, complementary strand of the promoter, thereby forming a functional RNA polymerase promoter structure, and b) synthesizing cRNA by transcription using an RNA polymerase specific for the promoter.

In some embodiments of the invention, a multimer cDNA obtained by RT-RCA of a circular target-adapter conjugate is used as a template for transcription by a bacteriophage RNA polymerase, yielding multiple copies of multimer ccRNA. In certain embodiments, this ccRNA is synthesized by: a) binding an oligo-deoxynucleotide comprising one strand of double stranded promoter for the RNA polymerase to the multimer cDNA encoding the second complementary strand of the promoter; b) optionally extending the oligo-deoxynucleotide (i.e., using it as a primer) by DNA polymerase; c) synthesizing multiple copies of ccRNA, which is complementary to the cDNA, by the RNA polymerase.

In some embodiments of the invention, a multimer cRNA obtained by the transcription methods described above serves as a template for reverse transcription to synthesize a single copy of ccDNA strand in following steps: a) binding an oligonucleotide RT primer that is substantially complementary to a cRNA sequence (for example, sequences in the target or in the adapter); b) synthesizing the ccDNA uisng a reverse transcriptase, and c) optionally degrading the cRNA strand (e.g., by RNAse H or alkali treatment).

In some embodiments of the invention, the RT primers described above are not immobilized on a solid support (or substrate) so that synthesized cDNAs stay in solution as well as the multimer cRNAs obtained by transcription methods. In certain embodiments of the invention, the multimer nucleic acids synthesized in solution are subjected to affinity capture through non-covalent binding with substantially complementary anchor oligonucleotide(s) immobilized on a solid support. Optionally, the anchor oligonucleotide can be enzymatically extended to provide synthesis of yet another complementary multimer DNA strand which will be covalently attachment to the solid support. In other embodiments of the invention, the RT primers described above are immobilized on a solid support and their enzymatic extensions provide direct covalent attachment of synthesized multimer cDNAs to the solid support. In certain embodiments, the solid support is selected from: beads (e.g. plastic, glass, magnetic or coded); membranes; filters; slides; microtiter plates; and microcapillaries.

In some embodiments of the invention, the attachment of multimer cDNAs (both non-covalent and covalent) can be use for purification of the cDNAs and/or their detection. In contrast to the purification task, certain embodiments of the detection task includes an arraying (or attachment) of target-specific oligonucleotides to target-designated beads, or spots, locations, or compartments on a solid surface (e.g., in the form of an array). In certain embodiments of the invention, the target-specific oligonucleotides comprise stringency elements (e.g., chemical modifications or competitive secondary structures) to provide adequate sequence-specificity of binding to homologous target sequences.

In some embodiments of the invention, the synthesized multimer nucleic acids (MNA) are labeled and subjected for detection without further nucleic acid amplification. This approach is best suited for the detection of abundant target RNAs.

Any convenient method for labeling MNA may be used, where in some embodiments of the invention, MNA is labeled using one or more of: a) an enzymatic labeling during the MNA enzymatic synthesis; and b) a chemical labeling after the MNA enzymatic synthesis. Any convenient label may be used, including, but not limited to: a radioactive isotope, a fluorophore, chemiluminescent moiety, a gold nanoparticle, a quantum dot, a hapten/ligand that can be recognized by antibody or aptamer conjugated with a signal-generating moiety.

In other embodiments of the invention, surface-bound MNA (either covalently or non-covalently bound to an anchor oligonucleotide on a solid support) is subjected to sandwich hybridization with signal oligonucleotide probes, which are substantially complementary (or corresponding) to either target or adapter sequences. The signal oligonucleotide probes are labeled before or can be labeled after the hybridization. In certain embodiments, the signal probes, which are complementary to target sequences, also comprise stringency elements (as described above). In some embodiments of the invention, the unlabeled signal oligonucleotide probe contains additional universal sequences that are complementary to a secondary, labeled nucleic acid probe such as branched DNA (bDNA) or DNA dendrimer. In certain embodiments, signal oligonucleotide probes are "muted" probes that induce a signal upon degradation by extension of the anchor oligonucleotide using a DNA polymerase with 5'-exonuclease activity.

In some embodiments of the invention, the synthesized multimer nucleic acids (MNA) are subjected to detection by real-time qPCR without the need for TaqMan probes. This method can be employed for the detection of both abundant and low-copy target RNAs because of its increased sensitivity. Optionally, the MNA can be subjected to affinity purification by capture on the immobilized anchor oligonucleotides and separated from the irrelevant nucleic acids before the PCR.

In preferred embodiments of the invention, PCR of multimer cDNA is performed using a pair of forward and reverse primers that are: a) overlapping at their 5' ends (are substantially complementary to each other and can form a dimer) and have non-overlapping overhangs at their 3' ends; b) complementary or correspond to overlapping segments of a repetitive target sequence; and c) form more thermostable duplex with respective target sequences than with each other. In certain embodiments of the invention, the 5'-end overlap is ≥2 nt shorter than the target sequences while the 3'-end overhangs are ≥1 nt long.

In some embodiments of the invention, the RT primer also serves as a reverse PCR primer along with additional forward PCR primer, whereas in other embodiments the RT primer has different sequence than the PCR primers.

In other embodiments of the invention, the RT and/or PCR primers are extended primers that comprise target-specific sequences at their 3' ends, which are substantially complementary or correspond to the target sequences, and adapter-specific sequences at their 5' ends, which are substantially complementary or correspond to the adapter sequences.

In other embodiments of the invention, the RT and/or PCR primers are combo primers that comprise target-specific sequences at their 3' ends and additional sequences at their 5' ends that are selected from: promoter for RNA polymerase, Zip-code, tag or ID sequence, a sequence which is not substantially complementary or corresponds to any sequence that can be present in the sample; a sequence encoding one or two linkers used for cloning and sequencing (including next-generation sequencing). In certain embodiments of the invention, the RT and/or PCR primers are combo primers that are used for first few rounds of conventional PCR, while another set of two PCR primers, which correspond to the additional sequences, is used for real-time qPCR. In other embodiments, first few rounds of PCR amplification is performed with only one combo primer, which is target-specific, and universal primer, which is specific to the adapter sequence, while the universal primer and another PCR primer, which is complementary to the additional sequence in combo PCR primer, are used for the real-time qPCR. In preferred embodiments, both the adapter and additional sequences are Zip-code sequences.

In certain embodiments of the invention, small target RNAs are detected and their amounts are quantified using the following steps: a) multiplex circularization of target RNAs (e.g., using RNA ligase 1 or CircLigase); b) multiplex synthesis of the corresponding multimers by RT-RCA using a mixture of short (8-10 nt) target-specific RT primers and a reverse transcriptase; c) singleplex real-time qPCR using target-specific dimer-primers that overlap for 15-16 nt at their 5'-ends and have 2-3 nt overhangs at their 3' ends.

DESCRIPTION OF THE DRAWINGS

FIG. 1. Schemes for small RNA circularization by ligation of the RNA 5' and 3' ends (miRNA is shown as an example). A: Intramolecular ligation using either a bacteriophage T4 RNA ligase 1 or T4 RNA ligase 2; or thermostable mutant bacteriophage RNA/DNA ligases (e.g. CircLigase I or CircLigase II or ThermoPhage ligase); or RNA ligases from other sources with similar properties; or chemical ligation of the RNA ends. B: Splint-assisted ligation using either a bacteriophage T4 RNA ligase 2 or T4 DNA ligase; or RNA/DNA ligases from other sources with similar properties; or chemical ligation of the target RNA ends aligned in a duplex structure with appropriate splint oligonucleotide, which is complementary to both ends of a target RNA.

FIG. 2. Schemes for synthesis of a polynucleotide consisting of tandem repeats of the complement of a small RNA by rolling circle amplification (RCA) of the circular form of the small RNA (miRNA is shown as an example). A: Reverse transcription (RT) of a circular miRNA (shown in FIG. 1) by RCA through extension of an RT primer by a reverse transcriptase lacking RNAse H activity (RT-RCA). Products of this reaction are multimeric cDNAs. Above: examples of various alignments of RT primers with the same circular miRNA template. B: Promoter-less transcription (T-RCA) with an RNA polymerase that can use small RNA circles as templates (used, for example, by RNA viruses, viroids or virusoids). Products of this reaction are also multimeric cRNAs.

FIG. 5. Comparison of RT-PCR primer designs for exponential amplification of monomer and multimer miRNA sequences. A: Forward (F) and reverse (R) primers for RT-PCR of monomeric small RNA sequences (or their cDNA) (miRNA is shown as an example). Only a pair of short suboptimal primer sequences not overlapping at their 3' ends can be used. The combined length of these sequences is equal to or shorter than the length of the miRNA (19-24 nt). B: Primers for RT-PCR of an MNA such as is generated by RT-RCA. MNA templates allow shifting of the alignment of the primer sequences across the boundary between two monomer sequence units, as well as the use of longer primers that overlap at their 5'-ends. C: Structures for allowed (left panel) and non-allowed (right panel) primer-dimers. The allowed dimers can be formed by a pair of primers that are partially complementary (overlap) at their 5'-ends; when hybridized to each other, their 3' ends are not extendable by a polymerase absent a template. The non-allowed dimers are formed by a pair of PCR primers that overlap at their 3'-ends, and, therefore, can be extended when hybridized to each other, producing non-target-specific (dead-end) amplicons.

FIG. 10. Comparison of RT-PCR primer designs for selective PCR amplification of homologous monomer and multimer miRNA sequences. A: Polymorphic sites in miRNAs representing certain let-7 miRNA isoforms (shown by dots). B: Forward (F) and reverse (R) primers for the RT-PCR of homologous monomer miRNA sequences (or their cDNAs). C: Primers for the RT-PCR of RT-RCA-generated MNA. MNA structure allow unlimited shifting the primer alignment including straddling of the boundaries between the monomer target sequences, and use of longer primers, which can overlap at their 5'-ends if necessary, to both adjust their $T_m$ and place primer 3' ends at the positions opposing mismatches.

A: Using the 3'-phosphate (3'-p). First, the ligation is carried out with an RNA ligase 1 (or RNA ligase 2) in the absence of ATP (–ATP) to prevent circularization of miRNA carrying 5'-p and 3'-OH. After purification of the miRNA-adapter conjugate, the 3'-p blocking group is removed by Polynucleotide kinase (it could be done under both –ATP and +ATP conditions). Then, the conjugate having now 5'-p and 3'-OH gets circularized by RNA Ligase or CircLigase (in the presence of ATP). B: Using 2'-OMe modification at the adapter's 3' end. There are only two steps. This modification prevents the adapter circularization by T4 RNA ligase during the conjugation reaction, but allows the purified conjugate circularization by CircLigase. C: Using a short adapter oligonucleotide, which is only 6-9 nt long and has a standard 2'-OH at its 3' end. The short length of the adapter prevents it from circularization by T4 RNA ligase during the conjugation reaction, but allows the purified conjugate circularization by T4 RNA ligase or CircLigase.

Figure 15:
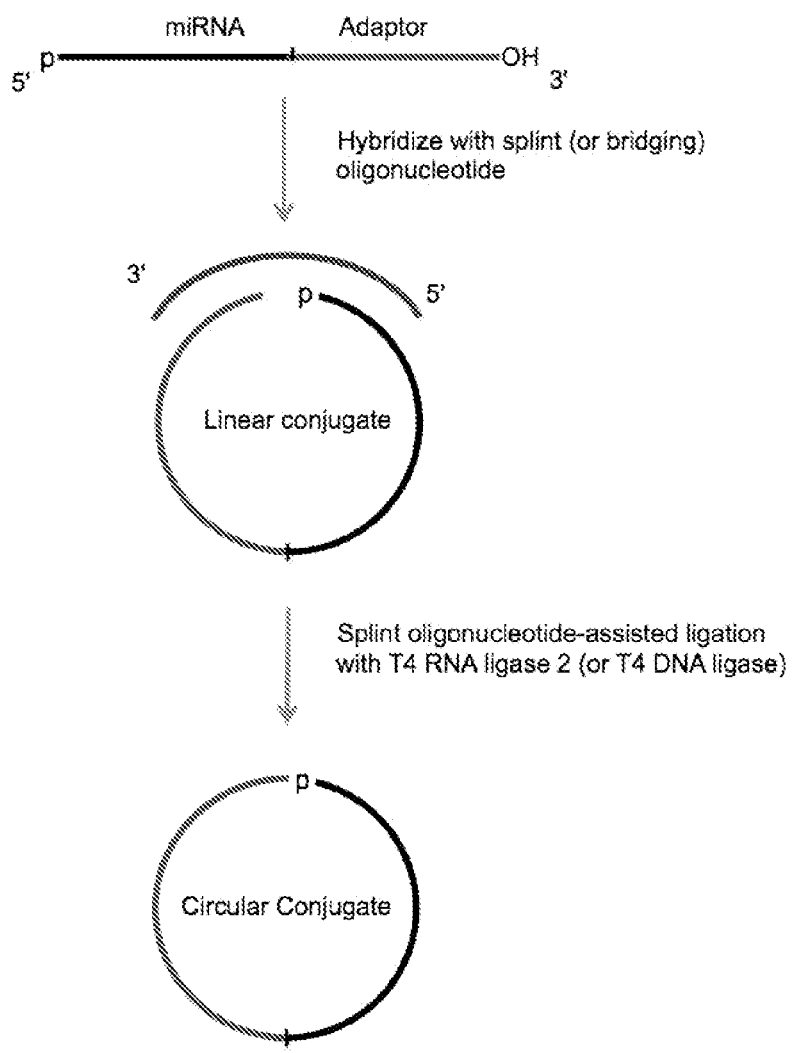

FIG. 15. Scheme for a splint-assisted circularization of a miRNA-adapter conjugate. Splint-assisted ligation using either a bacteriophage T4 RNA ligase 2 or T4 DNA ligase; or RNA/DNA ligases from other sources with similar properties; or chemical ligation of the target RNA ends aligned in a duplex structure with appropriate splint oligonucleotide, which is complementary to both 5' end sequence of miRNA and 3'-end sequence of the adapter.

Figure 16:
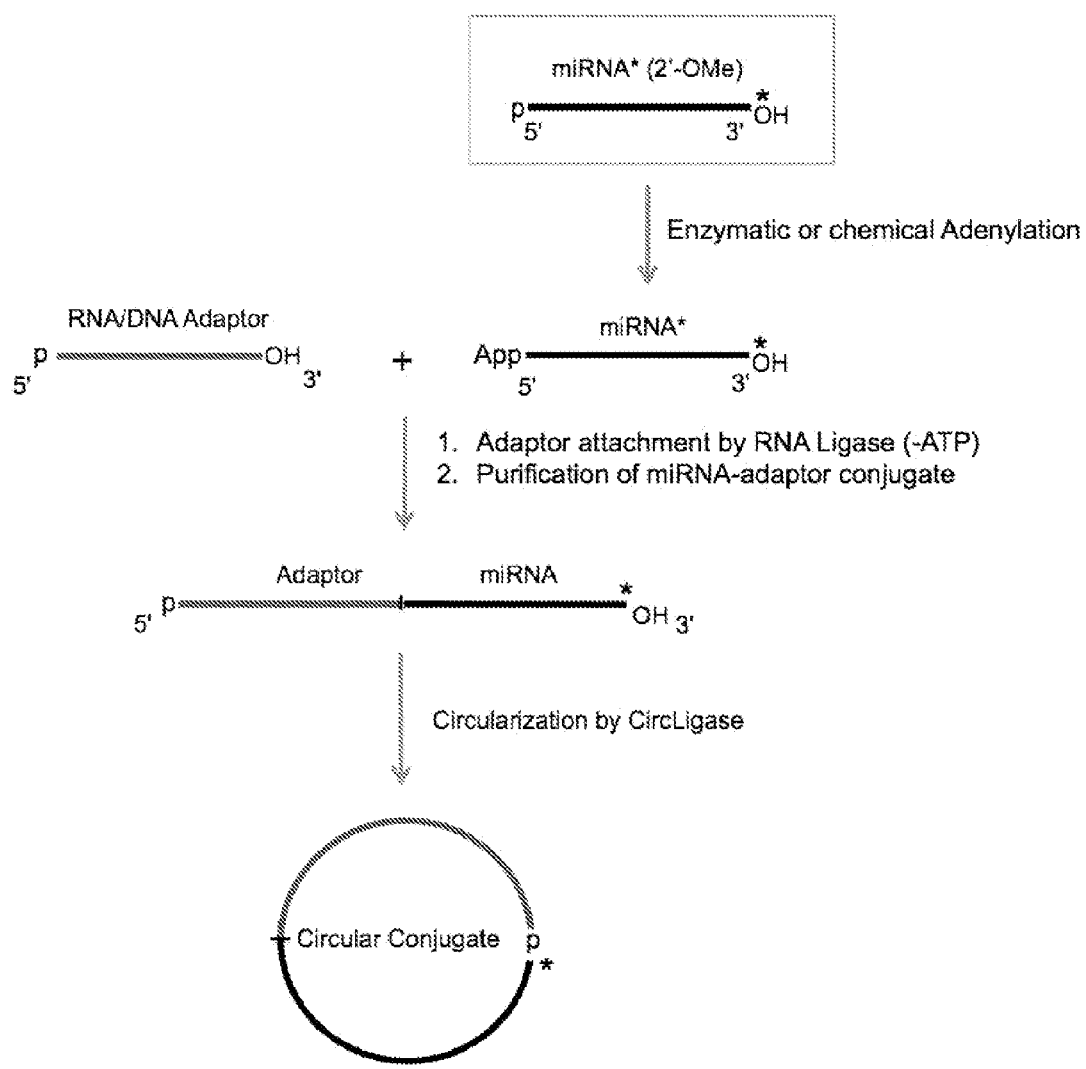

FIG. 16. Scheme for conjugation of 2'-OMe small RNAs with an adapter oligonucleotide and circularization of the conjugate (miRNA is shown as an example). This approach is similar to the scheme described in FIG. 14B except the miRNA is now have 2'-OMe modification while an adapter has 2'-OH at its 3'-end. The 2'-OMe miRNA naturally carrying 5'-phosphate and 3'-OH is adenylated by incubation with T4RNA ligase 1 in the presence of ATP (+ATP) without circularization. The conjugation reaction is carried out with an RNA ligase 1 (or RNA ligase 2) in the absence of ATP (–ATP) to prevent circularization of the adapter carrying 5'-p and 3'-OH. After a purification of miRNA-adapter conjugate, it gets directly circularized by RNA Ligase or CircLigase (in the presence of ATP).

Figure 17:
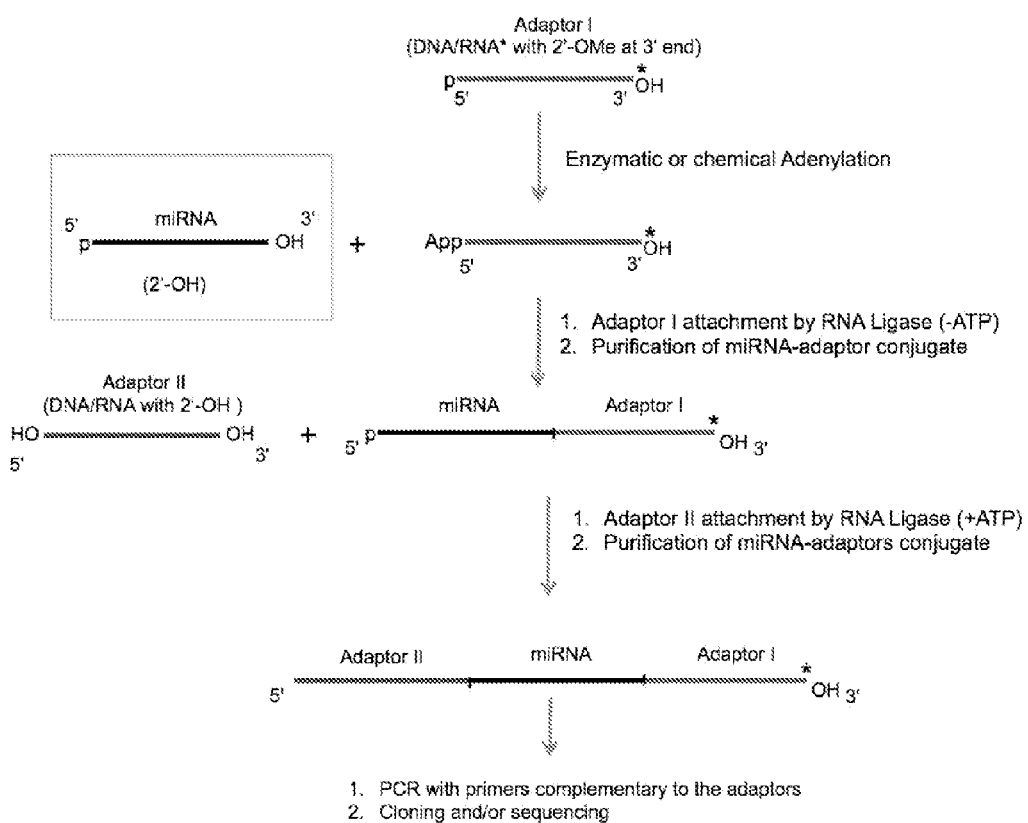

FIG. 17. Schemes for preparation of sequencing libraries of small RNAs using adenylated linker/adapter oligonucleotides with a 2'-OMe blocking group at its 3' end (miRNA is shown as an example). This approach is similar to the conventional two-adapter schemes of small RNA libraries preparation (Pfeffer et al. 2005) except the blocking group is 2'-OMe while 3'-OH remains unblocked. This modification prevents the adapter circularization by T4 RNA ligase during the conjugation reaction.

Figure 18:
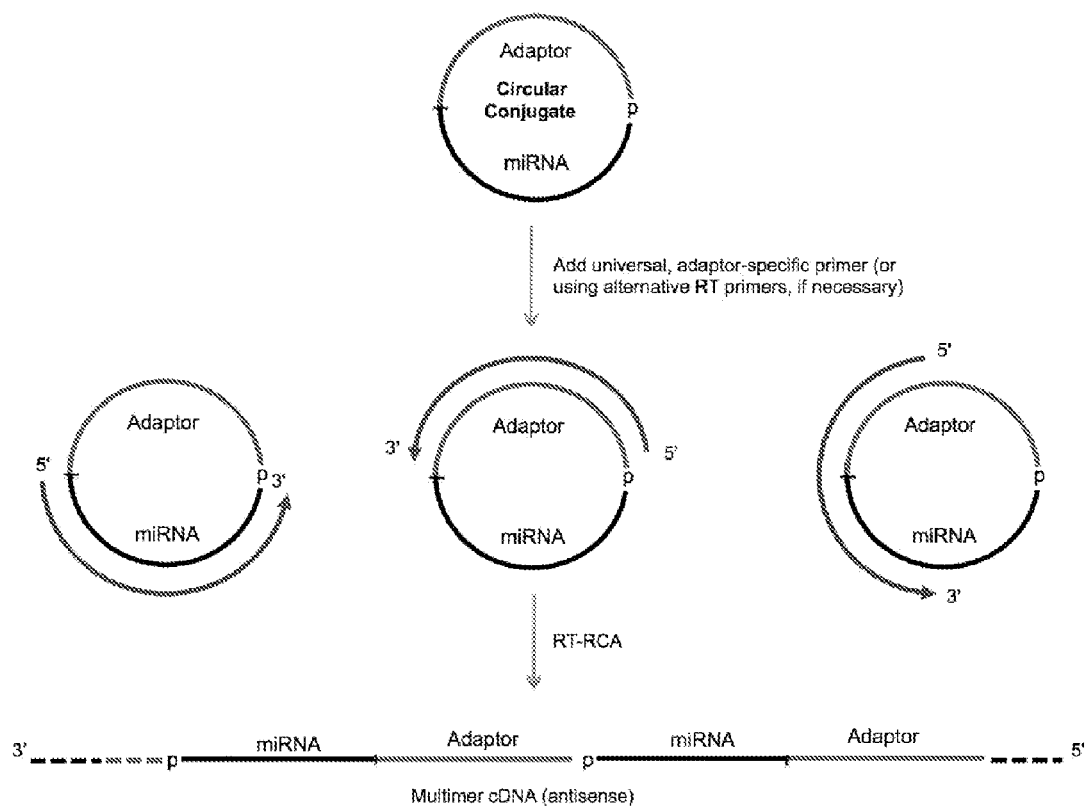

FIG. 18. Schemes for synthesis of multimeric polynucleotides by RT-RCA of circular small-RNA-adapter conjugates (miRNA is shown as an example). Reverse transcription (RT) of circular miRNA-adapter conjugates (from in FIGS. 14-16) by RCA extension of a RT primer using a reverse transcriptase lacking RNAse H activity. The primer extension can be run using reverse transcriptase (e.g. SuperScript II) that can use RNA and RNA-DNA chimeras as templates. The obtained multimeric cDNA product comprises multiple repeats of tandem target and adapter sequences. Alignments of RT primers with the circular miRNA-adapter template may vary (some examples are shown).

FIG. 19. Scheme for synthesis of multimer cRNA by transcription-mediated RCA using the circular small-RNA-adapter conjugates as templates (miRNA is shown as an example). A: Promoter-dependent transcription by appropriate RNA polymerase using a double-stranded promoter formed by a promoter-encoding adapter strand (antisense) and an added sense oligonucleotide, which is complementary to the adapter. RNA polymerases that are able to use both DNA and RNA as template can be used. B: Promoter-less transcription using an RNA polymerase that can recognize an RNA circle as template and initiate RNA-dependent RNA synthesis.

Figure 20:
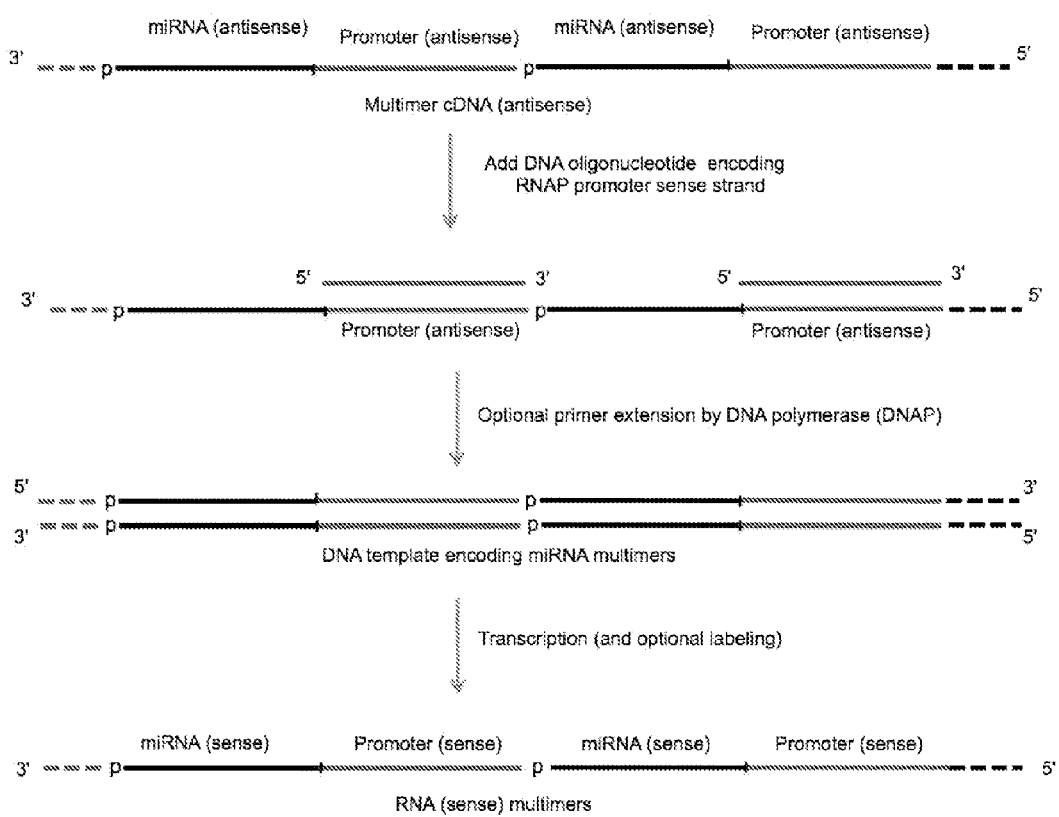

FIG. 20. Scheme for synthesis of multimer nucleic acids by promoter-dependent transcription from a multimer cDNA template consisting of repeats of small-RNA-adapter complements (miRNA is shown as an example). The transcription is initiated from a double-stranded promoter for RNA polymerases formed by the hybridization of the promoter-encoding adapter strand (antisense) with an added oligonucleotide (sense strand). Bacteriophage RNA polymerases (e.g. T7, T3 and SP6 RNAP) can be used for this purpose. Single-stranded cDNA or double-stranded DNA, obtained by the extension of the added oligonucleotide (sense promoter strand) with a DNA polymerase, can serve as templates.

FIG. 21. Schemes for detection of multimer nucleic acids, which consist of repeats of small-RNA-adapter complements using an anchor oligonucleotide probe immobilized on a solid support (miRNA is shown as an example). A: Direct detection by hybridization (capture) of labeled multimer cDNA or cRNA with a target-specific anchor probe. Labeling of the multimer nucleic acids (MNA) can be accomplished either enzymatically (e.g., during reverse transcription for cDNA or transcription for cRNA) or by post-transcriptional chemical modification. B: Sandwich hybridization of non-labeled MNA. There are two steps. The first step is target-specific capture of the MNA on the immobilized probe. The second step is hybridization with multiple signal oligonucleotide probes that correspond to the adapter sequence.

FIG. 22. Schemes for the detection of multimer nucleic acids (MNA), which consist of repeats of small-RNA-adapter complements, by enzymatic extension of an oligonucleotide primer immobilized on a solid support (miRNA is shown as an example). A: Capture of multimer nucleic acids (MNA) by hybridization with the target-specific primer; followed by the primer extension with DNA polymerase (for cDNA) or with reverse transcriptase (for cRNA); and simultaneous enzymatic labeling of ccDNA product. B: Capture of MNA on the target-specific primer; followed by sandwich hybridization with "muted" signal probes, which sequence corresponds to the adapter sequence. The signal probes are design to induce a signal upon degradation by extension of the target-specific primer using a DNA polymerase with 5'-exonuclease activity.

Figure 23:
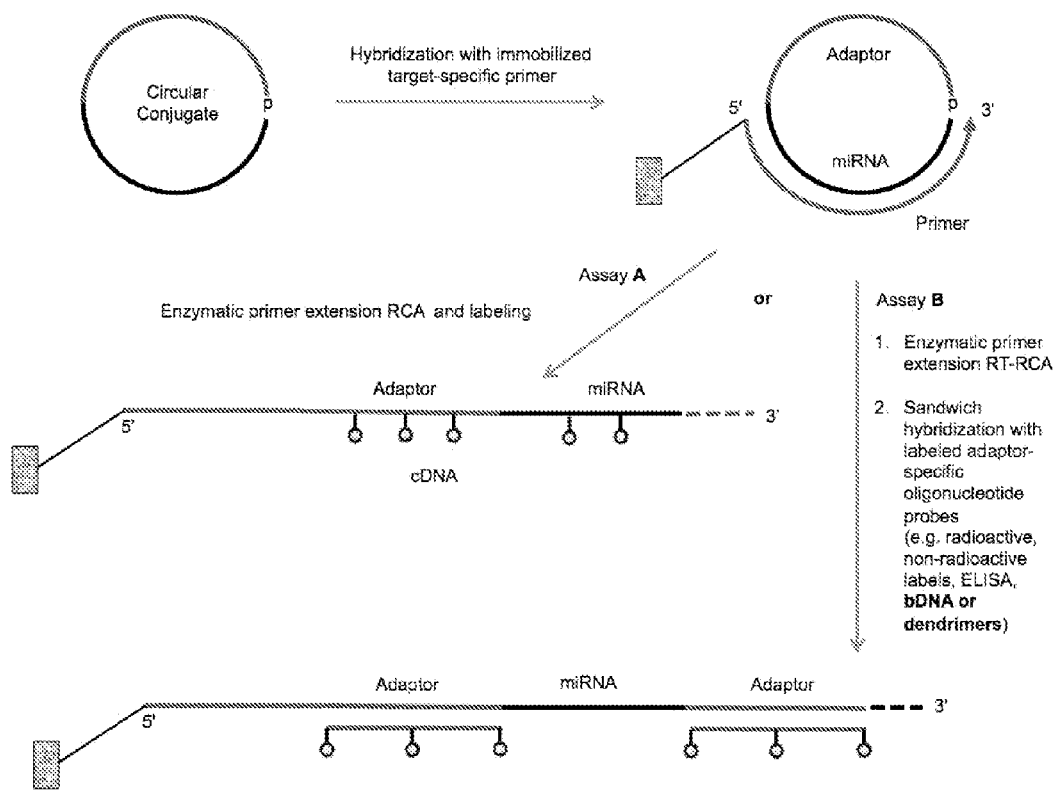

FIG. 23. Schemes for detection of circular small RNA-adapter conjugates by enzymatic extension of oligonucleotide primer immobilized on a solid support (miRNA is shown as an example). Capture of the circular conjugate by hybridization with the target-specific primer is followed by the rolling circle primer extension yielding multimer cDNA product. This cDNA comprises multiple repeats of tandem target and adapter sequences. When the adapter is RNA, an ordinary RNA-dependent DNA polymerase (reverse transcriptase) can be used. However, when the adapter is DNA or DNA-RNA chimera, a DNA polymerase that can use both RNA and DNA templates (e.g. SuperScript III) should be used. Assay A is using enzymatic labeling of multimer cDNA strand during primer extension. Assay B is using hybridization of non-labeled cDNA extension product with multiple signal oligonucleotide probes, in which the sequence corresponds to the adapter sequence.

Figure 24A:
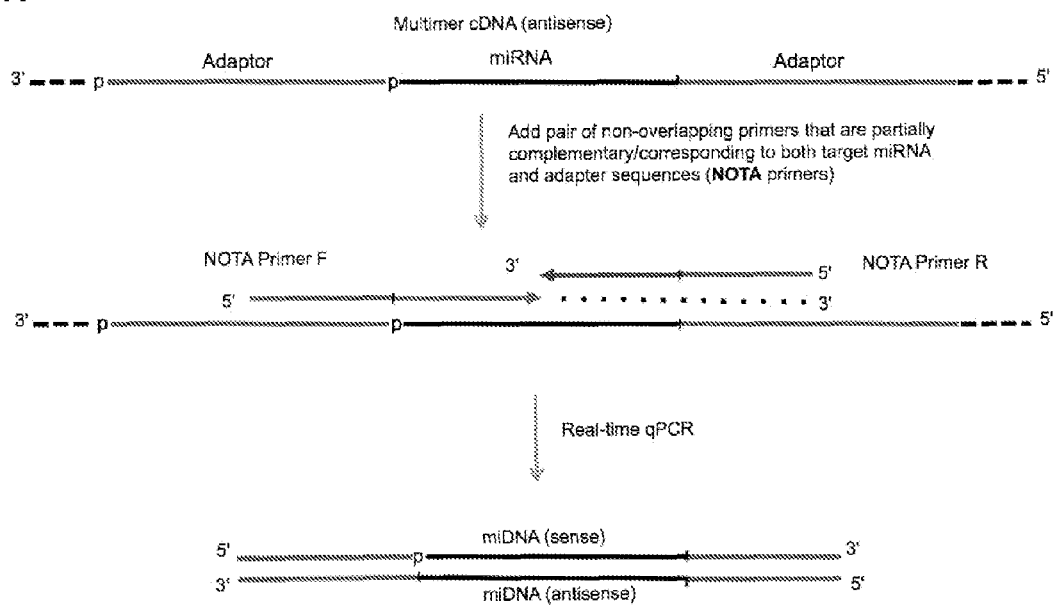
Figure 24B:
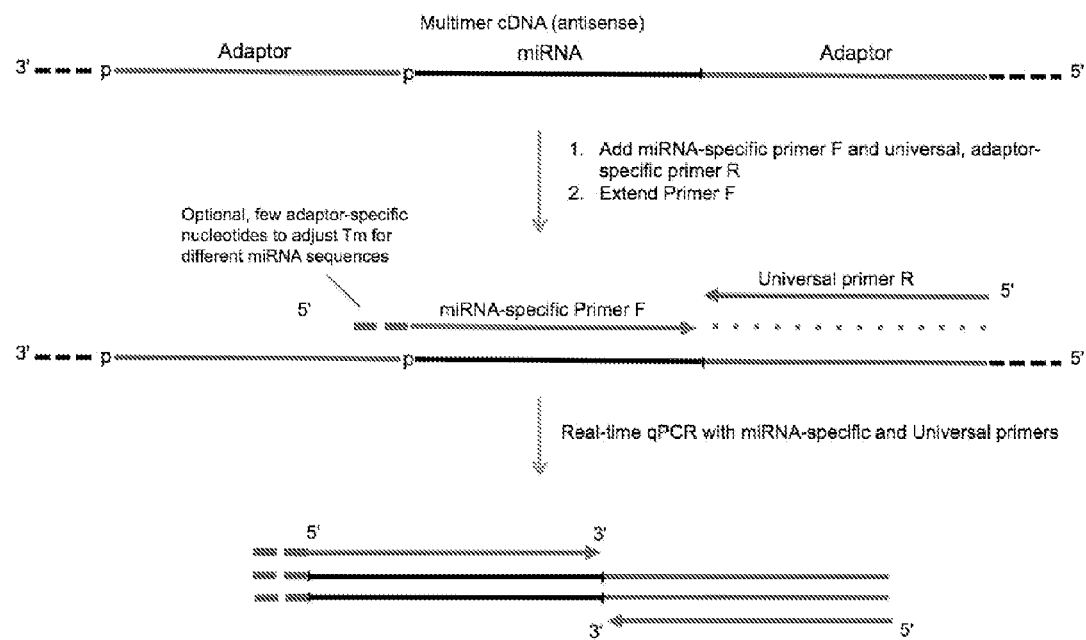
Figure 24C:
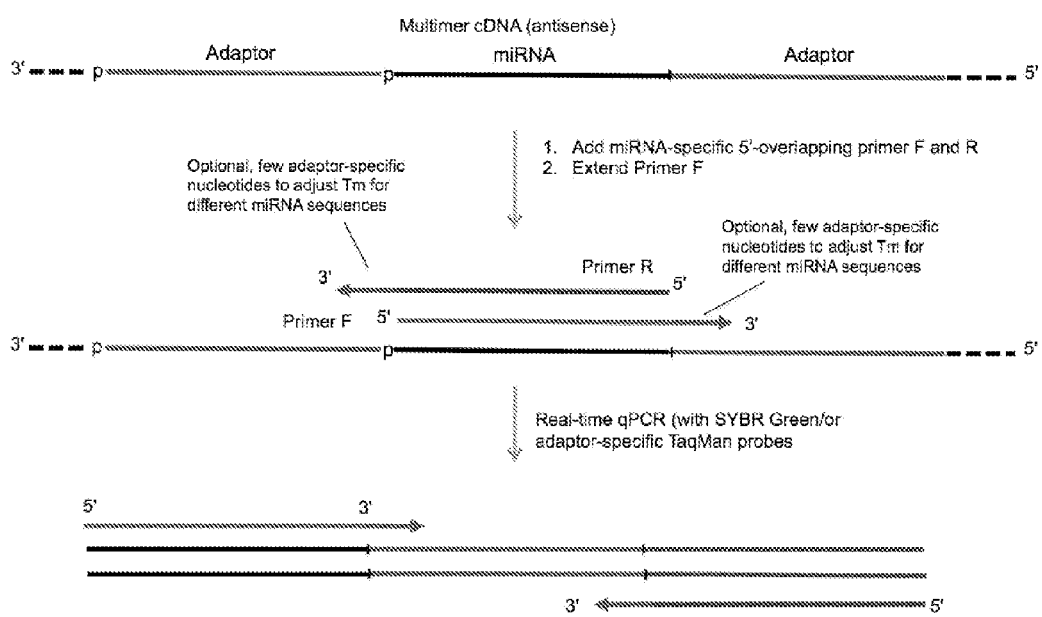

FIG. 24. Schemes for PCR amplification of multimer cDNAs consisting of repeats of small-RNA-adapter complements (miRNA is shown as an example). A: Using non-overlapping primers that both are partially complementary/corresponding to both small RNA targets and adapter sequences. B: Using non-overlapping primer pair, in which one primer is specific to target miRNA sequence whereas second primer is universal, adapter-specific. First primer may have short (1-5 nt) 5'-end extension, which partially complementary to adapter sequence. C: Using 5'-overlapping primers that both are specific to target miRNA sequence and have short (1-5 nt) 5'-end extension, which partially complementary to adapter sequence. The appropriate selected adapter-specific sequences (in all cases) allow adjustments and balancing these primers $T_m$.

Figure 25:
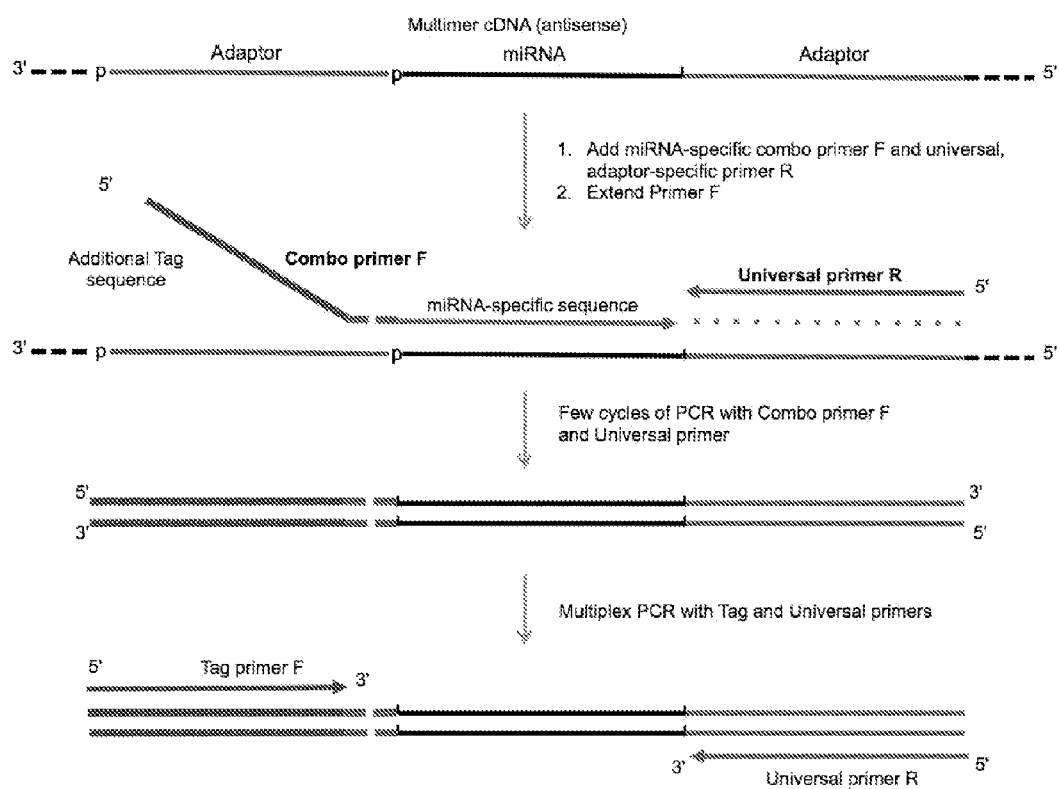

FIG. 25. Scheme for PCR amplification of multimer cDNAs, which consist of repeats of small-RNA-adapter complements, using target-specific combo primer and universal primer (miRNA is shown as an example). Combo primer comprises a 3'-end target miRNA-specific sequence, which corresponds to target sequences, and a 5'-end Additional Tag Sequence (ATS), which is not related to the target sequence but can be uniquely designated to the target or be universal, target-independent. The target-specific sequences may have short (1-5 nt) 5'-end extension, which partially complementary to adapter sequence to allow adjustments and balancing these primers $T_m$.

FIG. 26. Schemes for RT-PCR amplification of circular small RNA-adapter conjugates using a pair of primers, primer R serving as both RT and reverse PCR primer and primer F serving as the forward PCR primer (miRNA is shown as an example). A: Using non-overlapping, combo primers that are partially complementary/corresponding to adapter sequence only (NOCA primers). These reverse combo primer R serves as both RT and PCR primer while forward primer F serves as PCR primer only. These combo primers comprise adapter-specific sequences and additional upstream (5'-end) sequences, which are not substantially complementary or correspond to any sequence that can be present in a sample to be analyzed such as Zip-code/Taq sequences (universal or designated to specific target sequences) or adapter/linker sequences used for cloning and sequencing (including next-generation high throughput sequencing). These primers allow producing monomer PCR amplicons that can be directly used with the next-generation-sequencing if the adapter sequence encodes the method-specific primers. B: Using overlapping combo primers that are partially complementary/corresponding to adapter sequence only (FOCA primers). These combo primers are similar to NOCA primers except they substantially overlap in the middle. FOCA primers can form stronger duplexes with the complementary target sequences than with each other. These primers allow using shorter adapter but still function as NOCA primers. C: Using universal 5'-overlapping primers that are complementary/corresponding to adapter sequence only (FO primers). These primers allow producing multimeric PCR amplicons encoding multiple repeats of various miRNA sequences. The adapter sequences in this case are selected to encode appropriate cloning/sequencing linkers and/or restriction sites. D: Using miRNA-specific 5'-overlapping primers that are partially complementary/corresponding to both adapter and target miRNA sequences (FOTA primers). The target-specific sequences allow to selectively amplify miRNA sequences of interest (e.g. for expression profiling by either HTS sequencing or RT-qPCR). FOTA primers function similar to FO primers except they generate multimeric PCR amplicons encoding repeats of the selected miRNA sequences.

FIG. 27 (Example 1). Circularization of miRNAs, containing 2'-OH at their 3'-ends by T4 RNA Ligase 1 and CircLigase. A: Structures of hsa-let-7b miRNA (let-7b) and hsa-miR-127 miRNA (miR-127). B: Linear, 5'-$^{32}$P-labeled let 7b and miR-127 miRNAs were incubated with or without T4 RNA Ligase 1 and CircLigase and analyzed by gel-electrophoresis as described in Example 1. Both miRNAs were efficiently circularized by both enzymes.

FIG. 28 (Example 2): Circularization of miRNAs, containing either 2'-OH or a 2'-OMe at their 3'-ends. A: Circularization by T4 RNA Ligase 1. Linear, 5'-$^{32}$P-labeled let 7b miRNAs were incubated with or without T4 RNA ligase and analyzed by gel-electrophoresis as described in Example 2A. This enzyme can efficiently circularize only 2'-OH miRNAs whereas linear 2'-OMe miRNA is converted to its adenylated form (see panel D) without circularization. B: Circularization by CircLigase. Linear, 5'-$^{32}$P-labeled let 7b miRNAs were incubated with or without T4 RNA ligase and analyzed by gel-electrophoresis as described in Example 2B. This enzyme can efficiently circularize both 2'-OH and 2-OMe miRNAs. Circular miRNAs are resistant to exonuclease treatments while their linear form get degraded. C: Circularization of miRNAs with varying 3' end nucleotide with T4 RNA Ligase 1: 5'-$^{32}$P-labeled let-7b, let-7g, miR-16 and miR-23a, all containing 2'-OMe modification at the 3' end (and let-7b with a 2'-OH) and ending with U, A, G and C respectively were incubated in presence of T4 RNA Ligase 1 and analyzed by gel-electrophoresis as described in Example 2C. The inhibitory effect of the 2'-OMe modification on circularization by T4 RNA Ligase 1 strongly depends on the 3' end nucleotide: U~A>>C>G. The 2'-OH form of let-7 mRNA with 3'-U is circularized with high efficiency whereas its 2'-OMe form does not circularize all. D: Structures of adenylated 5' end (left) and 2'-OH/2'OMe 3' ends (right).

FIG. 29 (Example 3). Circular miRNA templates can be reverse transcribed by RCA extension of primers of different length (RT-RCA). A: Using trace amount of $^{32}$P-labeled primers. Circular let-7b miRNA was hybridized with 5'-$^{32}$P-labeled oligodeoxynucleotide primers of 10, 12 and 14 nt followed by reverse transcription and product analysis by gel-electrophoresis as described in Example 3A. B: Using non-radioactive RT primers: Circular miR-127 miRNA was hybridized with excess of non-radioactive oligodeoxynucleotide primers of 10 and 14 nt followed by reverse transcription and product analysis by gel-electrophoresis as described in Example 3B. All tested DNA primers generate multimer extension products consisting of miRNA complement repeats with similar efficiency showing no significant dependence on the primer length. However, the RT primer excess (over circular miRNA templates) provide higher efficiency of RT-RCA reactions.

Figure 6A:
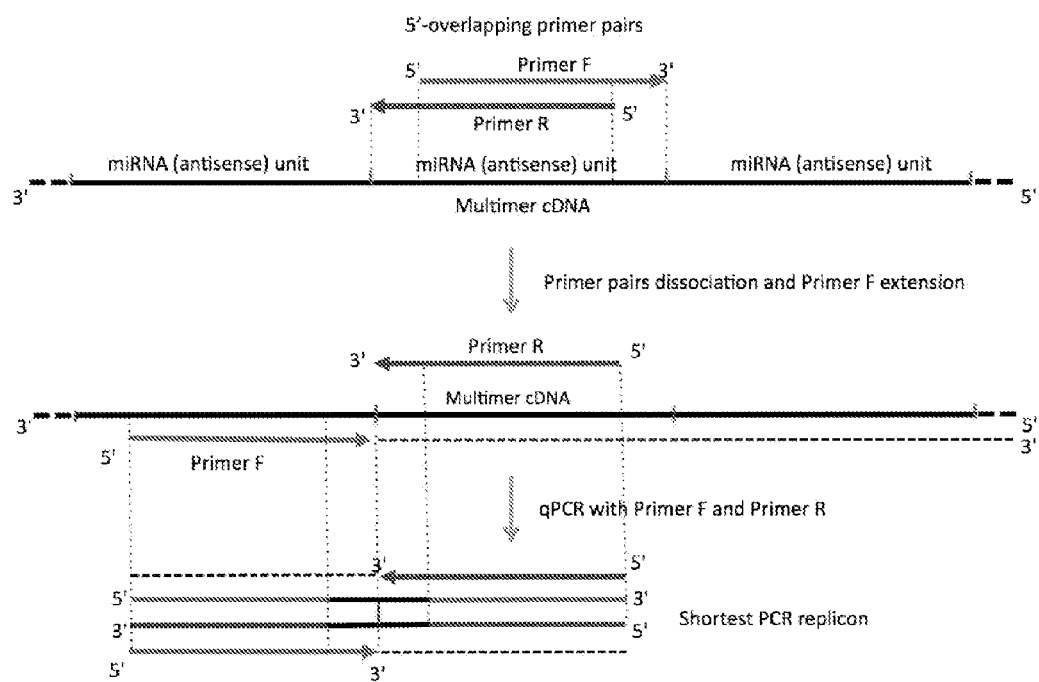
FIG. 6. Use of 5'-overlapping primers for amplification of RCA-generated multimeric cDNA (miR-ID approach; miRNA is shown as an example). miRNA-specific 5'-overlapping primer pairs that are complementary at their 5' ends and have short single-stranded overhangs at their 3' ends form more stable duplexes with their respective target sequences than with each other. A: Dissociation of the 5'-overlapping primer primers followed by extension of q forward primer (complementary to the multimeric cDNA) and PCR with both reverse and forward primers, generating multimeric PCR amplicons. The shortest amplicon is shown as an example. The alignment between primers and miRNA sequence repeats may vary. The combination of the consecutive steps of circularization (FIG. 1A), RT-RCA (FIG. 2A) and qPCR (described in this figure) represents the miR-ID approach for small RNA detection. B: Examples of possible alignments of the 5'-overlapping primer pairs with target miRNA sequences, including straddling of the boundaries between the monomer units. C-D: Examples of relative alignments of primers with linear and circular monomer miRNA sequences. The reverse primer R can serve both as RT and reverse PCR primer along with forward PCR primer F.
Figure 30:
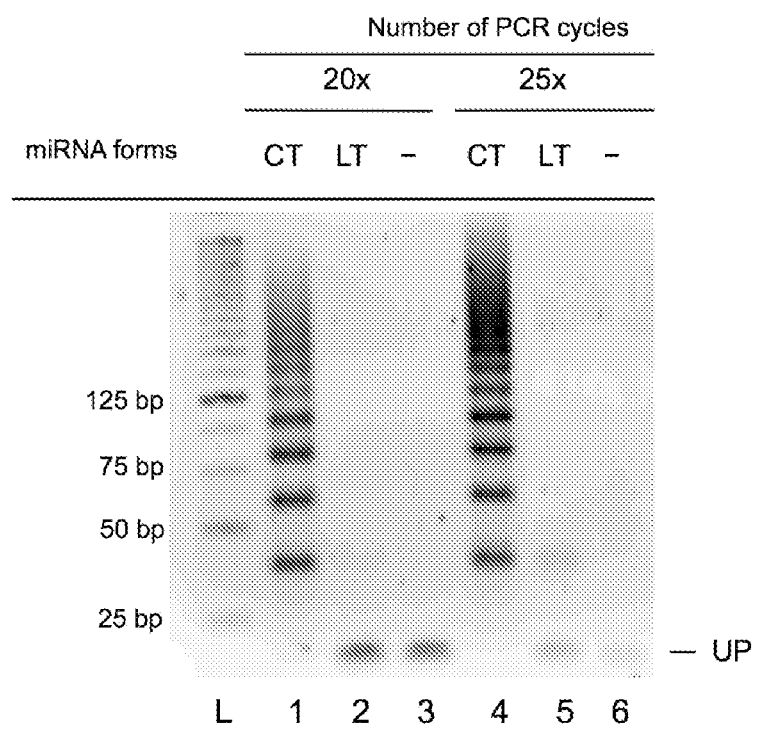

FIG. 30 (Example 4). RT-PCR amplification of circular miRNA by 5'-overlapping primers generates multimer cDNA. Both circular let-7b miRNA target (CT) and its linear form (LT) were assayed. Samples containing no miRNA target marked as "−" were used as negative controls. An 18 nt Primer R was used for both RT-RCA and PCR reactions along with the 18 nt Primer F used for PCR reaction. The reactions were carried out and analyzed by gel-electrophoresis as described in only as described in Example 4. Alignments of these 5'-overlapping primers with the linear and circular miRNA targets is shown in FIG. 6C. As expected, no amplification products were detected for the linear non-circularized (linear) miRNA. Circular miRNAs generate multimer cDNA amplification products that get elongated with increased number of PCR cycles. This elongation is result of additional OE-PCR process (see FIG. 8) which running in parallel with normal PCR reaction.

FIG. 31 (Example 5). Testing sensitivity of small RNA detection miR-ID assay (miRNA was used as an example).

This assay consists of three consecutive steps: (1) circularization of the miRNA (FIG. 1A); (2) RT-RCA of the circularized miRNAs (FIG. 2A), and (3) real-time qPCR with 5'-overlapping primers (FIG. 6A) using SYBR Green for signal detection. A: Using T4 RNA Ligase 1 in the circularization step. This is a default format for this new assay. Standard curves for different concentrations of lin-4 miRNA varying from 0.2 nM to 0.02 fM were generated using miR-ID and TaqMan microRNA RT-PCR assays as described in Example 5A. Both assays have similar dynamic range, but miR-ID is about 30 times more sensitive than the TaqMan assay based on Ct=5 between the corresponding standard curves ($2^5$=32). The superior sensitivity of miR-ID is can be explained by additional signal amplification provided by RT-RCA and OE-PCR. B: Using T4 RNA Ligase 2 in the circularization step. This is an alternative format for miR-ID, which may have limited application since not all miRNAs can be circularized by a splint-assisted ligation. However, this approach allows simultaneous circularization and RT-RCA reactions that may have certain advantages (such as higher sensitivity and shorter assay time) for assaying of appropriate miRNA targets. Standard curves for different concentrations of lin-4 miRNA varying from 0.2 nM to 0.02 fM were generated as described in Example 5B and compared to those fort the first miR-ID and TaqMan assays. This, alternative miR-ID assay, provides even higher (about 8 times) sensitivity than the first miR-ID while both miR-ID assays provide much higher sensitivity than the TaqMan assay.

Figure 12A:
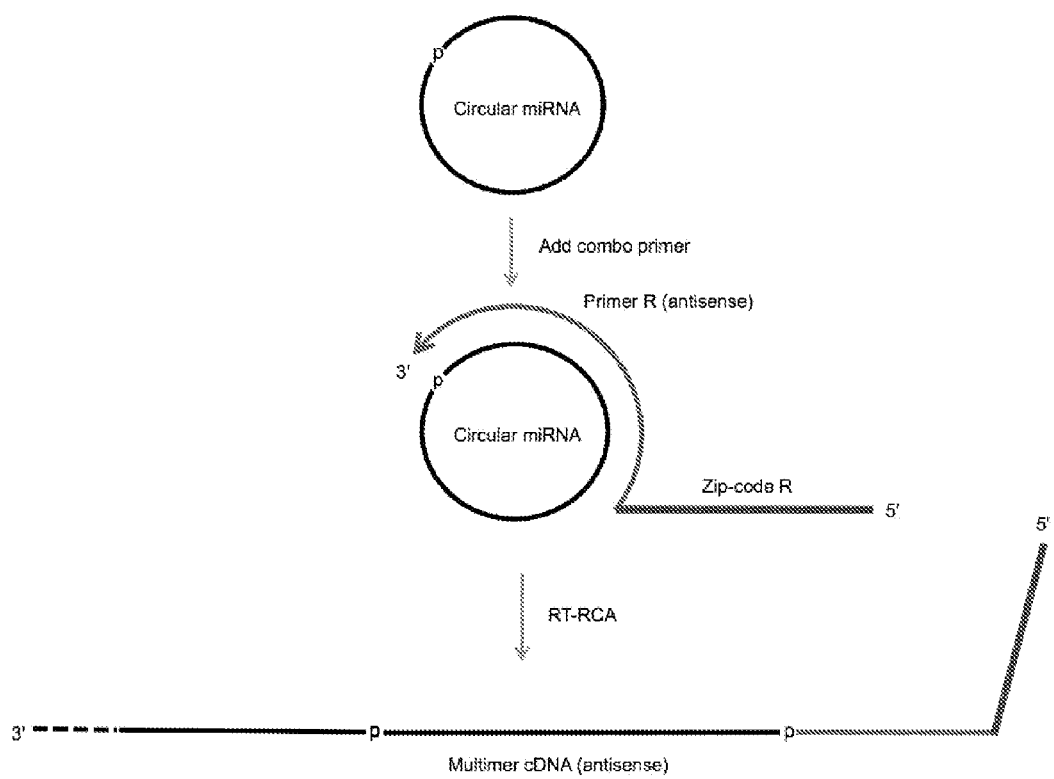
FIG. 12. Combo RT primers can be used both as RT and PCR primers. These primers have the structure and functions as described in FIG. 11, but here RT primers are used for both reverse transcription step (A) and for PCR step as a reverse PCR primer (B) where as in FIG. 11 multimeric nucleic acids (MNA) templates were generated differently (as shown in FIG. 2).
Figure 12B:
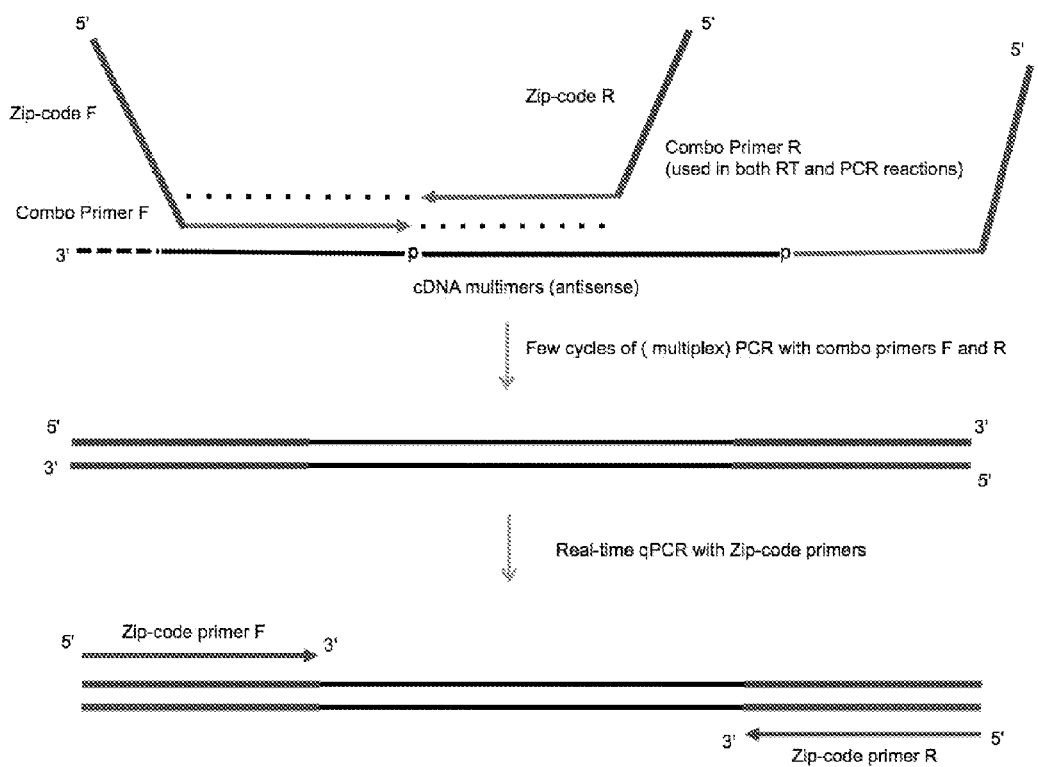
Figure 32:
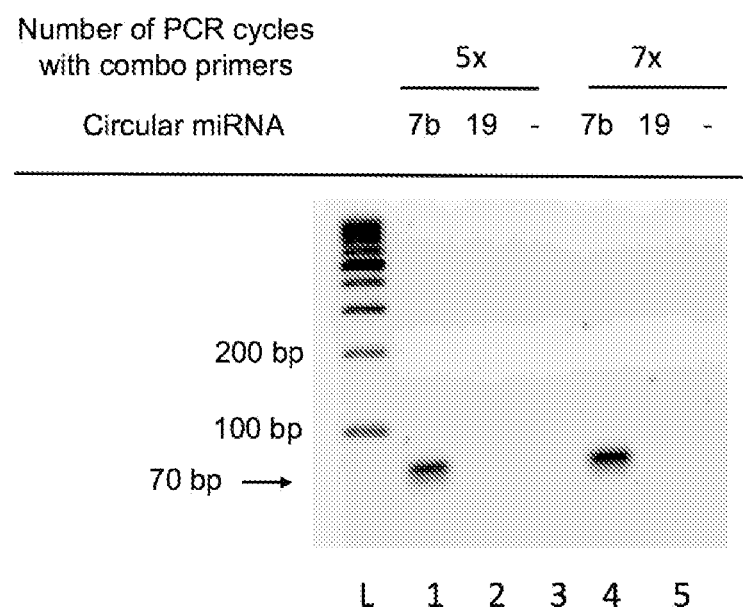

FIG. 32 (Example 6). Detection of small RNA by RT-PCR using combo primers (let 7b miRNA was used as an example). 35 nt combo Primer R and Primer F comprise two different sets of 11 nt miRNA-specific sequences at their 3' ends and 24 nt Zip-code sequences at their 5' ends. Alignments of these primers with the circular miRNA target and the corresponding multimer cDNA are shown in FIG. 12A and FIG. 12B, respectively. This assay was performed in three steps: (1) RT with the combo Primer R; (2) few cycles of PCR pre-amplification with the combo Primers R and F (number of the cycles is as indicated); and (3) 30 cycles of PCR with additional 24 nt Zip-code primers R and F. The reactions were performed and final products analyzed as described in Example 6. Only a single, target-specific product corresponding to expected 70 bp replicon was observed whereas the unrelated RNA19 and the negative control (−) showed no products. The use of combo primers provides target-specific signal pre-amplification (128 times for 7 PCR cycles) before PCR with the Zip-code primers that are amenable for multiplex PCR.

Figure 33:
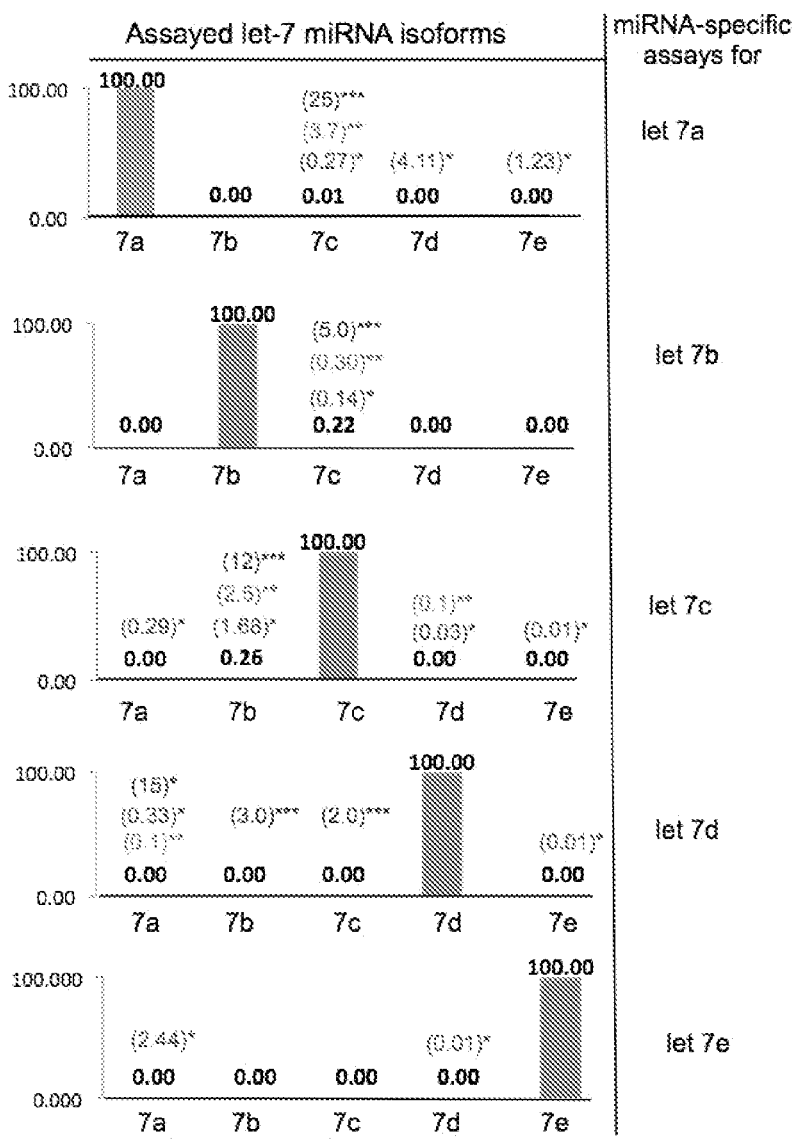

FIG. 33 (Example 7). Discrimination of closely related miRNAs in miR-ID assays A: Sequence alignments of human let-7 miRNA isoforms a-e. The differences between let-7a and the other isoforms are shown in red. let-7a: SEQ ID NO:2; let-7b: SEQ ID NO:3; let-7c: SEQ ID NO:4; let-7d: SEQ ID NO:5; let-7e: SEQ ID NO:6 B: Comparison of the qPCR signal data obtained for cross-assays of the let-7 miRNA isoforms by all isoform-specific PCR primers. The miR-ID assays were performed in a cross-reaction manner (every miRNA isoform was subjected to qPCR with every PCR primer set) as described in Example 7. The maximum signal in each assay was normalized to 100, and the other values were calculated relative to the maximum signal. Experimental data were plotted on a linear scale. Values (others than 0.0) for corresponding miRNA RT-PCR assays from Qiagen's miScript/SYBR Green (*), ABI's TaqMan ()(Chen et al. 2005) and LNA/SYBR Green (*)(Raymond et al. 2005) are shown in parentheses. miR-ID can easily discriminate miRNA species that differ by as little as 1 nt while demonstrating superior sequence specificity in comparison to the other methods commonly used for miRNA detection.

FIG. 34 (Example 8). Discrimination between mature miRNA and pre-miRNA. A: Sequences and structure of mature let-7b miRNA and its precursor (pre-miRNA). The sequence of the mature miRNA is highlighted in the pre-miRNA structure. B: Representative RT-qPCR amplification curves for synthetic let-7b and pre-let-7b using RT-PCR primers specific to the mature form. Mature let-7b and pre-let-7b were assayed using miR-ID as described in Example 8. A ΔCt~12 between the mature miRNA and pre-miRNA assayed at the same concentration using the miRNA-specific primers implies at least a 4000-times ($2^{12}$=4096) discrimination between these two RNA forms.

Figure 35:
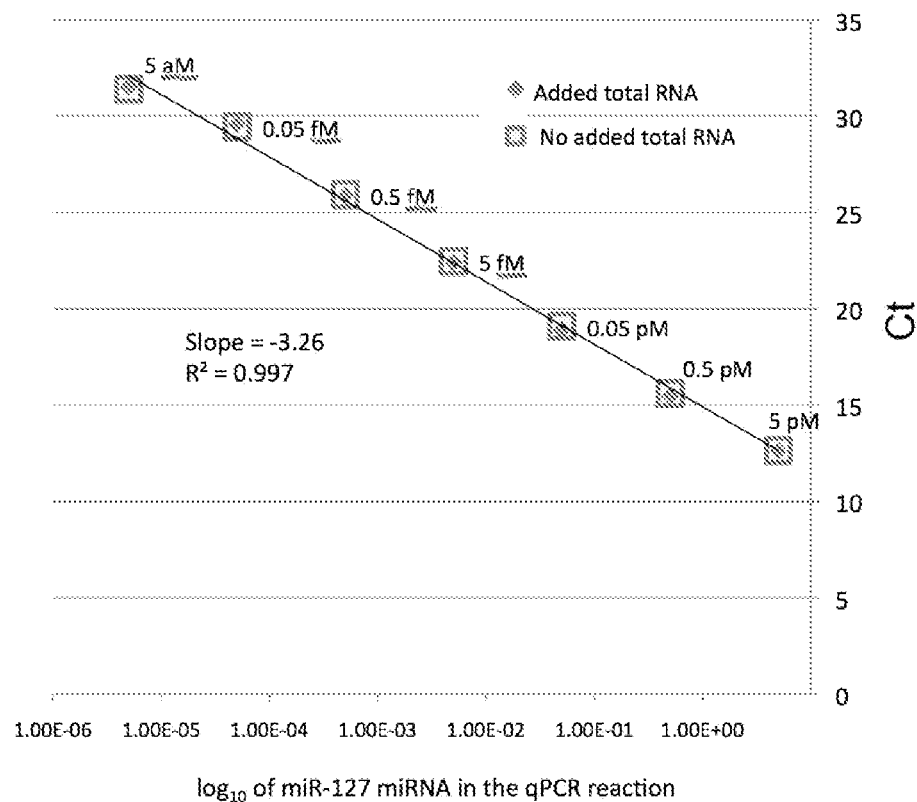

FIG. 35 (Example 9). Sensitivity and detection limit of an individual miRNA are not affected by presence of total RNA. Various concentrations of synthetic miR-127 were assayed using miR-ID in absence (red squares) or presence of 20 ng of total RNA extracted from Jurkat cells as described in Example 9. The presence of the total RNA had no effect on the assay sensitivity as shown by complete overlapping of the corresponding standard curves.

FIG. 36 (Example 10). Detection of endogenous miRNAs in total cellular RNA and Cell lysate. A: Using total cellular RNA. The endogenous human let-7b and miR-16 miRNAs were assayed by miR-ID in different amounts of total RNA extracted from as described in Example 10A. Based on standard curves for these miRNAs, they can be detected even in 20 pg of total RNA comparable to an average amount of RNA from a single cell (Yu et al. 2006). MiR-127, which is not expressed in these cells, provided Ct=40 of the background level at all total RNA concentration tested. B: Using cell lysate. The endogenous let-7b miRNAs were assayed by miR-ID in different amounts of cell lysate from Jurkat cells as described in Example 10B. Standard curves for detection of let-7b in both total RNA and cell lysate are shown for comparison. The detection of the same miRNA in purified fraction of total RNA extracted from the same cells provided only marginally better sensitivity (ΔCt~2) compared to the crude cell lysate.

FIG. 37 (Example 11). Linear fold-change values of mouse miRNAs in total RNA extracted from various tissues. 100 ng of mouse total RNA from brain, heart, liver, thymus, lung, embryo and ovary were subjected to miR-ID assay as described in Example 11. Sno234 (small nucleolar RNA) was utilized as the endogenous reference for normalization of RNA input and efficiency of RT-PCR reactions. Average (R=0.86) linear fold expression values for miRNAs let-7a, miR-16, miR-20, miR-21 and miR-22 relative to the liver expression (chosen as the calibrator tissue, in which expression value was normalized to 1) is shown. The found relative miRNA expression levels were in good correlation with the expression profiles of the same miRNAs in corresponding tissues previously obtained by TaqMan micro RNA assay (Chen et al. 2005).

Figure 38A:
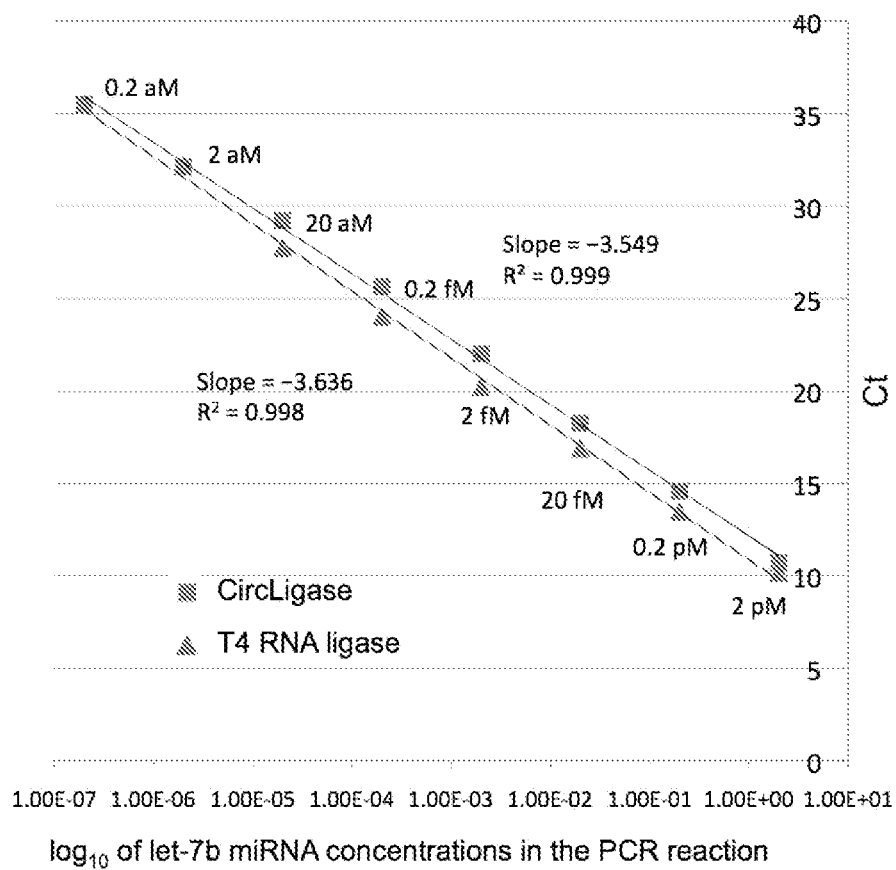

FIG. 38 (Example 12). Discrimination between 2'-OH and 2'-OMe miRNA forms in miR-ID assays using T4RNA Ligase 1 and CircLigase in the circularization step. A: T4 RNA ligase 1 and CircLigase II provide similar signals in miR-ID assays for 2'-OH miRNAs. Various concentrations of synthetic let-7b miRNA, which have a 5'-p and 2'-OH/3'-OH at its 3' end, was subjected to circularization by T4 RNA ligase 1 or CircLigase II in separate reactions and further assayed in similar steps as described in Example 12A. These two RNA ligases, which have very similar circularization efficiency (see FIG. 27B), also provide similar standard curves for normal human miRNAs carrying 2'-OH group at its 3' end (2'-OH miRNAs). B: Identification and detection of miRNAs having 2'-OMe modification at their 3' ends (2'-OMe miRNAs). Synthetic miRNAs (let-7g, let-7b and miR-16; Table 1), having a 5'-p and a 2'-OMe/3'-OH at the 3' end were subjected to circularization by T4 RNA ligase 1 or CircLigase II and further assayed in similar steps as described in Example 12B. The 2'-OMe miRNAs, which were tested in this examples had different 3'-end nucleotides as indicated in the bottom panel. Shown relative signal intensities for each miRNA using alternative ligase treatments demonstrate that that miR-ID can detect small RNAs carrying both 2'-OH and 2'-OMe groups at their 3' ends RNAs as well as distinguish them from each other using similar ability of CircLigase and T4RNA Ligase 1 to circularize the 2'-OH miRNAs but significantly different abilities of these enzymes to circularize the 2'-OMe miRNAs. The discrimination between these miRNA forms seems do not significantly affected by the different 3' end nucleotides. C: Determination of percentage methylation of miRNAs in a mix containing both 2'-OH and 2'-OMe forms. Synthetic let-7b miRNAs, which had 5'-p and either 2'-OH/3'-OH or 2'-OMe/3'-OH at the 3' end, were mixed in different pre-defined proportions of the 2'-OMe modification. Identical samples of these mixtures were circularized using either T4 RNA Ligase 1 or CircLigase II and further assayed in similar steps as described in Example 12C. The normalized data is shown demonstrating the miR-ID ability not only detect both 2'-OH and 2'-OMe miRNA forms but also to determine their ratio in samples.

FIG. 39: Enzymatic conversion of small RNA termini into a form detectable by miR-ID. The shown naturally occurring modifications at RNA termini can prevent small RNA circularization and therefore their detection by miR-ID. However, these modified ends can be converted into ligatable forms by standard enzymatic treatments as indicated. The need for the specific treatment (before the circularization step) for detection of certain small RNAs would indicate the presence of the corresponding modifications at their ends.

Figure 11A:
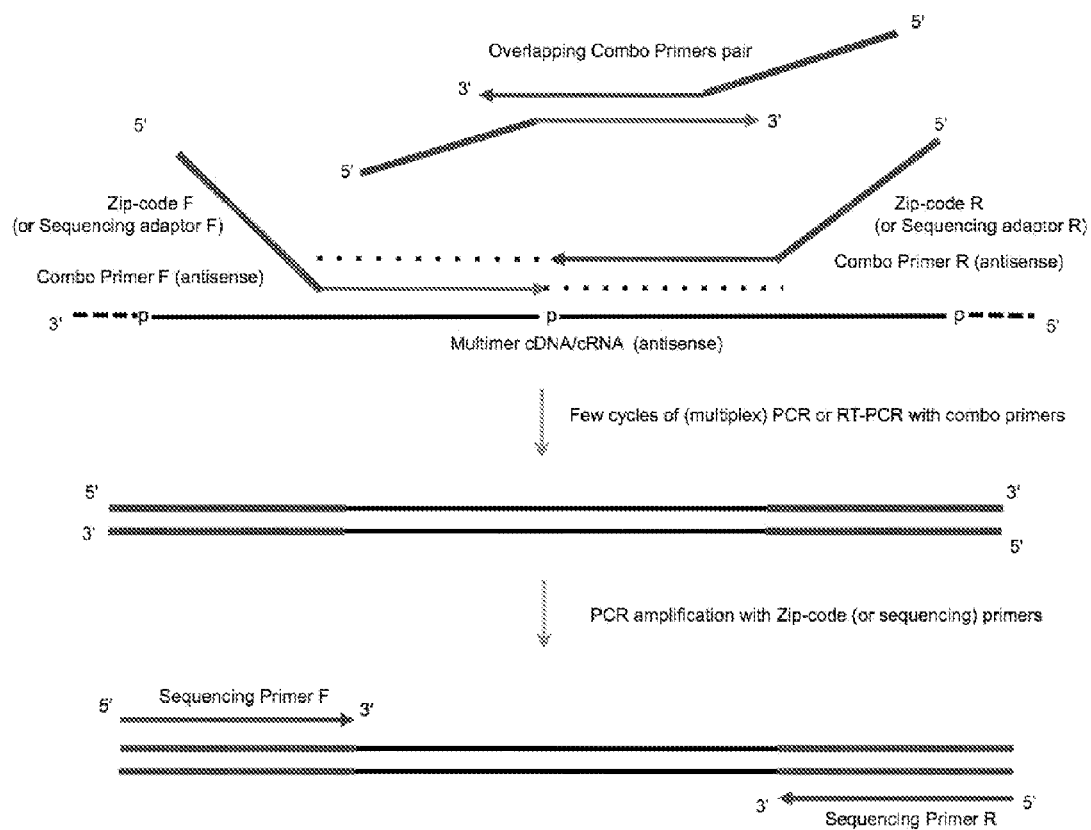
FIG. 11. Combo primers for multiplex amplification of multimer nucleic acid sequences. These combo RT and PCR primers comprise target-specific sequences and additional upstream (5'-end) sequences, which are not substantially complementary or correspond to any sequence that can be present in a sample to be analyzed. These primers can substantially overlap in the middle but still form stronger duplexes with the complementary multimeric nucleic acids (MNA) strands generated as shown in FIG. 2. The 5'-end additional sequences of combo primers can play several functions. A: Additional sequences comprising either Zip-code/Taq sequences (universal or designated to specific target sequences) or adapter/linker sequences used for cloning and sequencing (including next-generation high throughput sequencing). Such combo primers are used for the first few rounds of PCR (if the template is multimer cDNA) or RT-PCR (if the template is multimer cRNA), while another set of two PCR primers, which are complementary to the additional sequences, is used next for either multiplex qPCR (for analytical purpose) or preparative PCR (for sequencing purpose). B: Short (1-5 nt) additional sequences can be used for optimization of primer $T_m$ as well as to prevent overlap-extension amplification (if necessary). Such primers are used in the first few PCR rounds at a lower annealing temperature (based on the target specific sequence), followed by increasing the annealing temperature (based on the entire primer length, including the 5' overhang sequence) for the remaining cycles.
Figure 40:
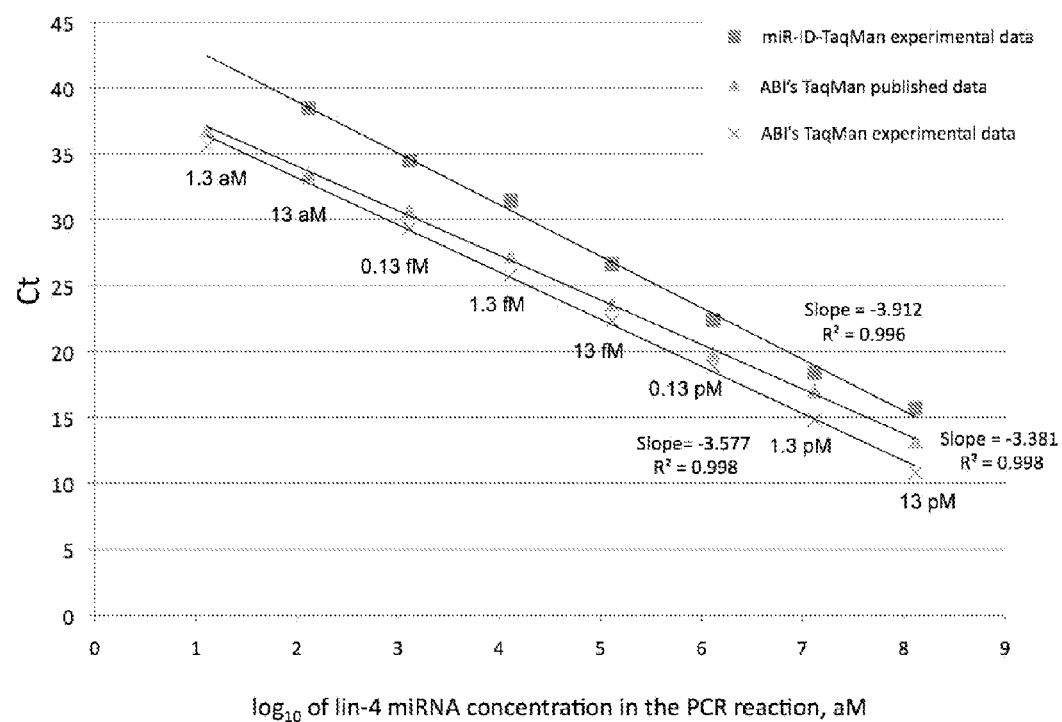

FIG. 40 (Example 13). Testing dynamic range and sensitivity of detection of modified miR-ID assay using overlapping combo primers and TaqMan probes (miR-ID-Taq assay). Here we used overlapping combo primers rather than the 5'-overlapping primers used in the default miR-ID assay (FIG. 31). These combo primers are specific to target miRNA repetitive sequences at their 3' ends and have Tag sequence (i.e. Zip-code) uniquely designated (but not related) to the target (FIG. 11A). The custom TaqMan probe complementary to the Tag sequence were used as schematically described in FIG. 13B. Various concentrations (1.3 nM, 0.13 nM, 13 pM, 1.3 pM, 0.13 pM, 13 fM and 1.3 fM) of synthetic lin-4 were assayed as described in Example 13. The obtained standard curve were compared to standard curves for the standard TaqMan assay for this miRNA. The detection limit for this miR-ID-Taq assay was determined to be 13 aM (equivalent to 70 copies of lin-4) in the PCR reaction. Based on ΔCt=5, current miR-ID-Taq assay was found about 30-times less sensitive than the TaqMan assay. However, the performance of this new assay can be improved after optimization of the probe design and assay conditions.

FIG. 41 (Example 14). Modified miR-ID assay using isothermal strand-displacement technique instead of PCR for signal amplification (miRSA assay). This method shares the same circularization (FIG. 1A) and RT-RCA steps (FIG. 2A) with miR-ID, but differs in step 3. In this last step, miRSA use isothermal, hyperbranched strand-displacement (HSDA) reaction (FIG. 7) rather that PCR (FIG. 6A) while both methods employ similar 5'-overlapping primer pairs. A: Semi-quantitative validation of HSDA using synthetic lin-4. Various concentrations of synthetic cel-lin-4 were subjected to miRSA assay and analyzed by gel-electrophoresis as described in Example 14A. Long amplification products and strong signal amplification even for 20 aM miRNA concentration demonstrate very high sensitivity of miRSA in this semi-quantitative experiment. B: Standard curve of lin-4 using HSDA. Various concentrations of synthetic lin-4 were subjected to real-time quantitative miRSA as described in Example 14B. The comparison of the standard curves obtained by miRSA and miR-ID assays indicate that they provide very similar sensitivities, which are about 30 times better than that for ABI's TaqMan assay. C: Demonstration of miRSA assay specificity by discrimination of closely related let-7 miRNA isoforms. Synthetic miRNAs let-7a, let-7b, let-7c, let-7d and let-7e (FIG. 33A) were subjected to real-time quantitative miRSA as described in Example 14C. The maximum signal in each assay was normalized to 100, and the remaining values were calculated relative to the maximum signal. Data was plotted on a linear scale. There were no non-specific amplifications recorded. Analysis of the discrimination factors between the let-7 isoforms assayed in cross-reaction manners demonstrates that miRSA provides superior sequence-specificity as compared to miR-ID (FIG. 33B).

Figure 14A:
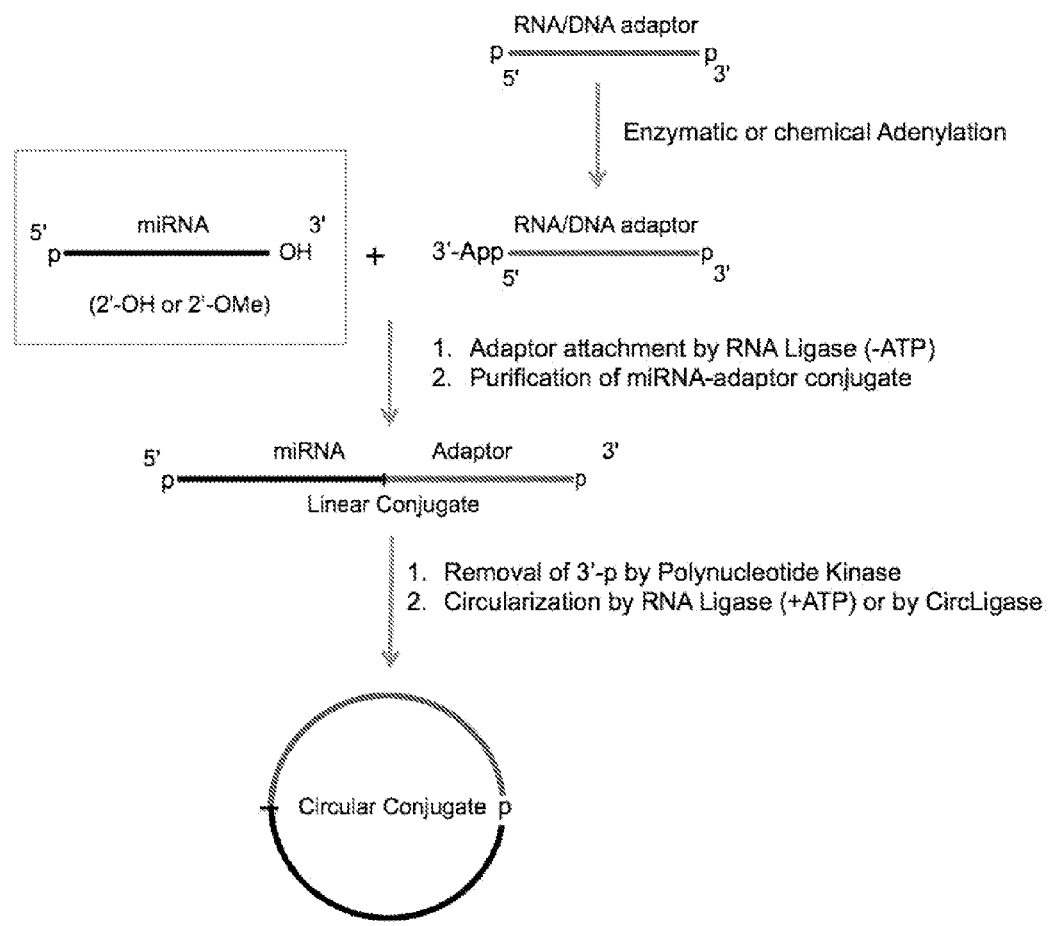
FIG. 14. Schemes for conjugation of small RNAs carrying 2'-OH (at its 3' end) with an adenylated adapter oligonucleotide and circularization of the conjugate. (miRNA is shown as an example). The adenylated adapter (DNA or RNA) can be obtained by appropriate enzymatic or chemical synthesis known in art. An adapter normally should have a blocking group at its 3' end to prevent circularization either during the adapter adenylation and/or attachment of the adenylated adapter to miRNA (conjugation reaction) by T4 RNA ligase. Three novel ways of protecting 3' ends on the conjugation step while allowing the circularization are described below.
Figure 14B:
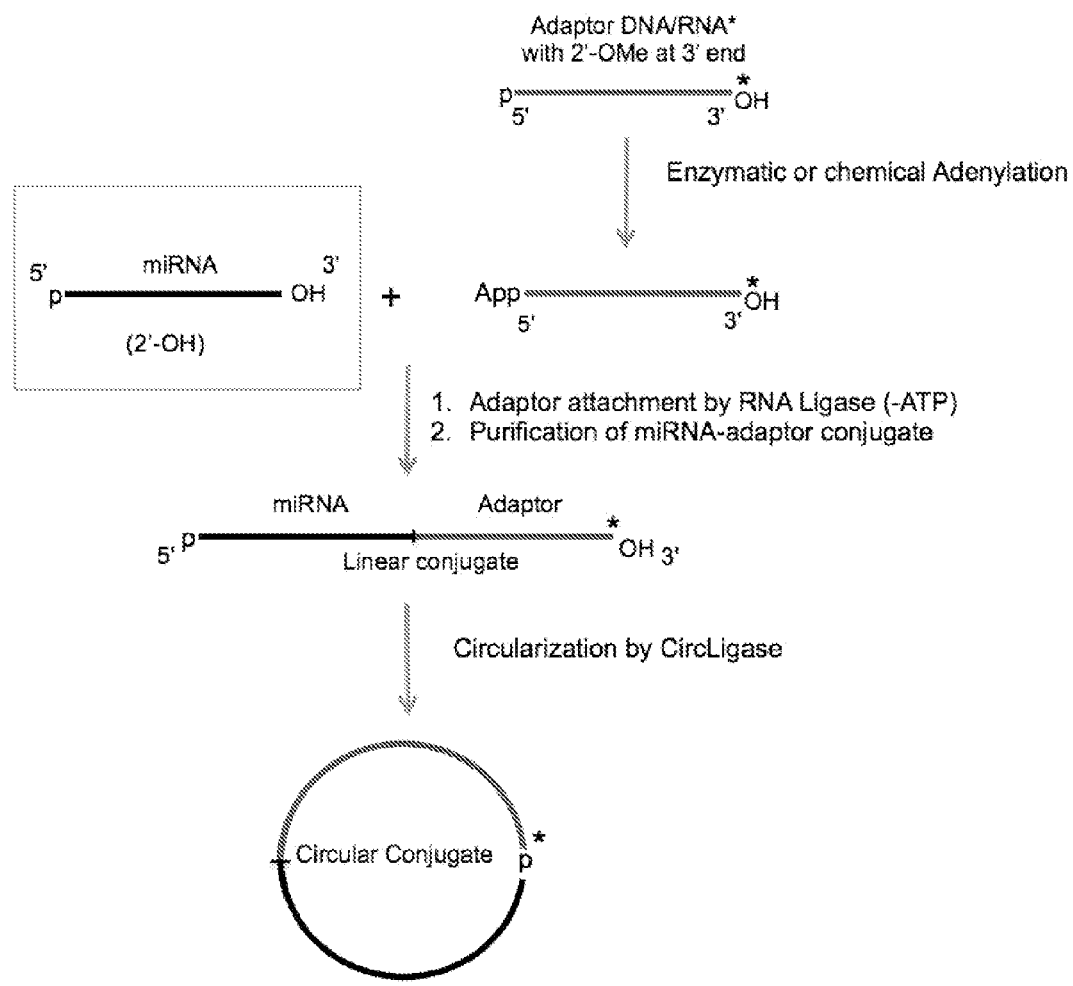
Figure 42:
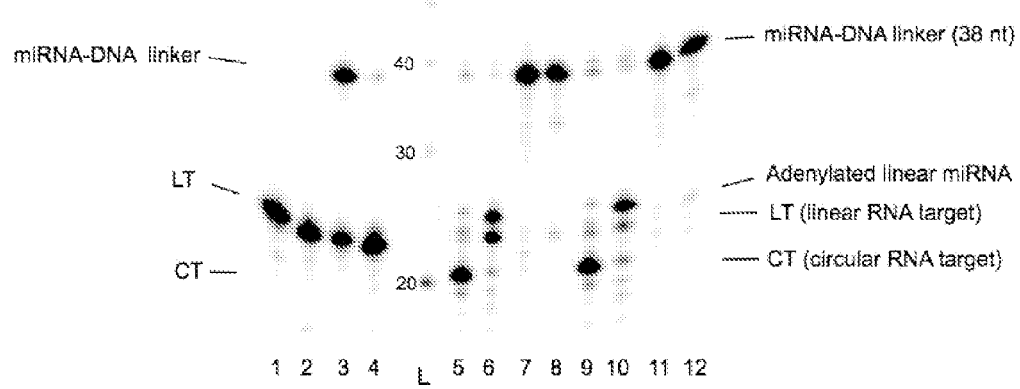

FIG. 42 (Example 15). Attachment of adenylated adapter to 2'-OH and 2'-OMe miRNAs by T4 RNA ligase 1. 5'-$^{32}$P-labeled linear let-7b miRNAs, which had 2'-OH or 2'-OMe at their 3' end, were incubated with adenylated (FIG. 28D) miRNA cloning adapter, (18 nt) and T4 RNA ligase 1; and reaction product were analyzed by gel-electrophoresis as described in Example 15. In the absence of ATP, the adenylated DNA rapidly ligated to the linear miRNAs (LT) regardless of the presence of 2'-OH or 2'-OMe ends (RNA-DNA product, which was up shifted in the gel). The 2'-OH end provides faster adapter ligation to miRNA than 2'-OMe end, but both ligation reactions were fully completed after 1 h. No circularization of the 2'-OH miRNAs occurred in the absence of ATP, whereas in the presence of ATP, no ligation of the 2'-OH miRNA with the adapter occurred. Instead, this miRNA underwent complete circularization after just 1 h forming CT product, which moved slightly faster than LT. The 2'-OMe miRNA could not be circularized by T4 RNA ligase 1-instead, this miRNA gets converted into the adenylated form, which moved slightly slower than LT. The fact that 2'-OMe RNA can be easily adenylated by T4 RNA ligase in the presence of ATP without self-circularization implies that the adenylated 2'-OMe modification at 3' end can be used as 3' end blocking group in RNA/DNA adapters as shown in FIG. 14B and FIG. 17.

DETAILED DESCRIPTION OF THE INVENTION

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Before the present invention, the circularization of small RNAs naturally carrying 5'-p and 3'-OH by T4 RNA ligase was regarded as an obstacle and explicitly avoided in detecting short RNAs (Aravin & Tuschl 2005). Additionally, the short length of small RNA targets was recognized as a factor limiting the use of conventional PCR primers as are the norm in current assays (Chen et al. 2005; Jiang et al. 2005).

In contrast, the methods of the present invention include the circularization of target RNAs and allow assaying of small RNAs with both 2'OH and 2'-OMe at their 3' ends. We capitalize on the ability of small RNA targets, or their conjugates with oligonucleotide adapters, to be circularized (it is noted here that the terms "adapter" and "adapter" are used interchangeably herein). The circular RNA templates provide a feature for the amplification of the target (and adapter) sequences via synthesis of multimer nucleic acids that can be either labeled for direct detection or subjected to PCR amplification and detection. The structure of small RNAs and their multimeric forms provide certain advantages, including unmatched flexibility in design of conventional RT and PCR primers as well as the use of overlapping dimer-primers for efficient and sequence-specific amplification of short target sequences. Our invention also reduces the number of steps and reagents while increasing the sensitivity and accuracy of detection of small RNAs in samples.

Aspects of the invention include methods of detecting the presence of a known target RNA in a sample, including the general steps of: a) circularizing the target RNA by ligation of its 5'- and 3'-ends; b) synthesis of multimer nucleic acid (MNA) comprising multiple repeats of sequences that are complementary to the target RNA by rolling circle amplification (RCA); and c) assaying for the presence of the MNA, thereby detecting the presence of the target RNA in a sample.

In some embodiments of the invention, the assayed samples represent extracts from biologically and clinically relevant tissues or cells and are selected from: crude nucleic acid extract; total RNA extract; and fractions of small RNAs whose length is determined by the method of purification.

In some embodiments of the invention, the target RNAs comprise the following features: a) size ranging from 10 to 100 nucleotides (nt); b) 5'-phosphate (5'-p) or other naturally existing 5'-end group such as: cap, 5'-triphosphate (5'-ppp), and 5'-hydroxyl (5'-OH) that can be converted to 5'-p before the ligation and/or circularization (FIG. 39); c) 3'-phosphate (3'-p) or 2',3'-cyclic phosphate (2',3'>p), which can be converted to 3'-OH before the ligation and/or circularization (FIG. 39); d) 3'-hydroxyl (3'-OH); e) 2'-OH or 2'-OMe at the target 3'-end. In preferred embodiments, target RNAs are miRNAs and other small RNAs of lengths in the range of 19-40 nt. However, some methods of the invention are not limited to small RNAs and are equally applicable for any RNA that can be circularized.

In preferred embodiments of the invention, multiple target RNAs are simultaneously detected or discovered in the samples.

In certain embodiments of the invention, the method of RNA circularization is selected from: direct ligation using T4 RNA ligase 1, T4 RNA ligase 2 or CircLigase or chemical ligation (FIG. 1A); splint-assisted ligation using T4 RNA ligase 2 or a DNA ligase or a chemical ligation (FIG. 1B). In certain embodiments, the use of bacteriophage T4 RNA ligase 1 or CircLigase is preferable since they are universal (not dependent on target-sequences) and allow multiplexing at the ligation/circularization step(s). In contrast, the splint-assisted ligation does require prior knowledge of RNA target sequences and therefore can be applied only for detection of known RNA rather than discovery new ones.

We demonstrated that T4 RNA ligase 1, which efficiently circularized 5'-phosphorylated 22 nt miRNA having 2'-OH and 3'-OH at its 3' end (FIGS. 27-28 and Example 1A), could not circularize miRNA having similar 2'-OMe at its 3' end (Example 2A and FIGS. 28A and 28C). However, we found that another enzyme, CircLigase (Epicentre), can effectively circularize miRNA with both 2'-OH and 2'-OMe groups at their 3' ends. We used exonuclease Exo I, which could degrade linear miRNAs but not their circular forms, to confirm the circularization. We found that Exo I can efficiently degrade linear 2'-OMe RNA albeit slower than its 2'-OH form (see Example 2B and FIG. 28B). Epicentre describes the CircLigase™ ssDNA Ligase as a thermostable ligase, which can efficiently circularize single-stranded DNA or RNA of >30 nt with 5'-p and 3'-OH (Polidoros et al. 2006). The ability of CircLigase to circularize small 2'-OMe RNAs was not described before our finding. There are other thermostable ligases homologous to T4 RNA ligase 1 that may act similarly to CircLigase (Blondal et al. 2003; Hjorleifsdottir et al. 2007).

In certain embodiments of the invention, the circularization of a target RNA or extended target RNA (target-adapter conjugate) is followed by degradation of linear nucleic acids by an exonuclease (e.g. Exo I, FIG. 28B) or mixture of exonucleases as an optional step to reduce a background signal that may evolve as result of unintentional amplification of unrelated RNA molecules. Since RNA ligase 1 preferentially ligates small RNAs with 5'-p and 3'-OH, whose length is in range of 10 to 30 nucleotides (Kaufmann et al. 1974), the degradation of nucleic acids that are not circularized may result in automatic enrichment of these small RNA in the samples.

Figure 29A:
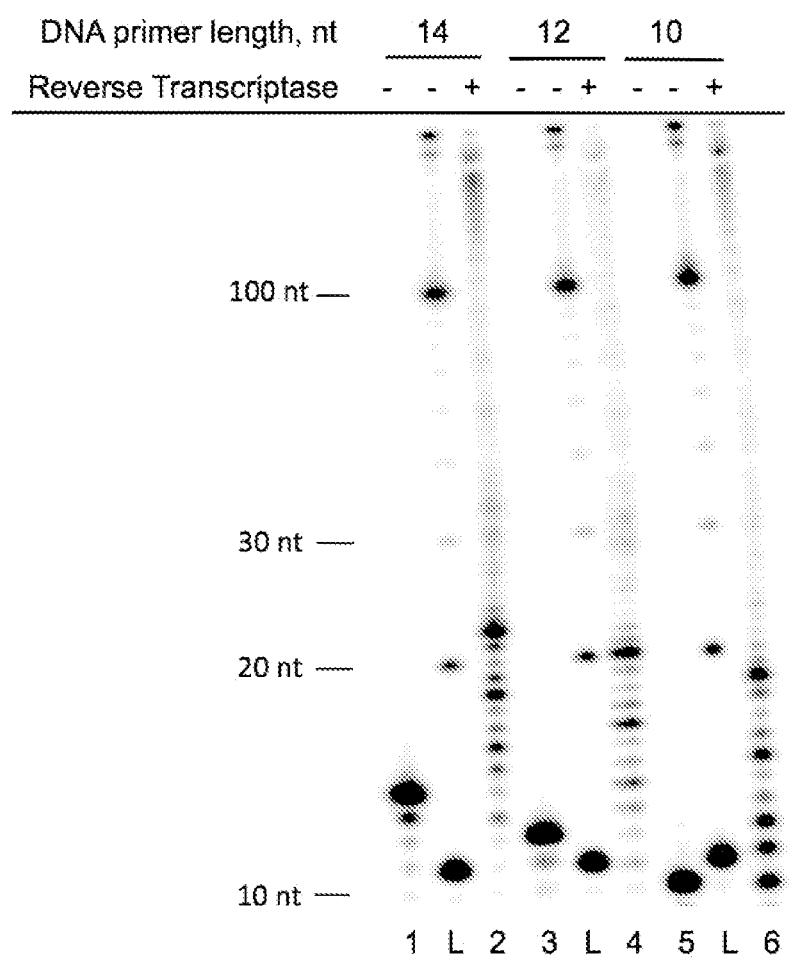
Figure 29B:
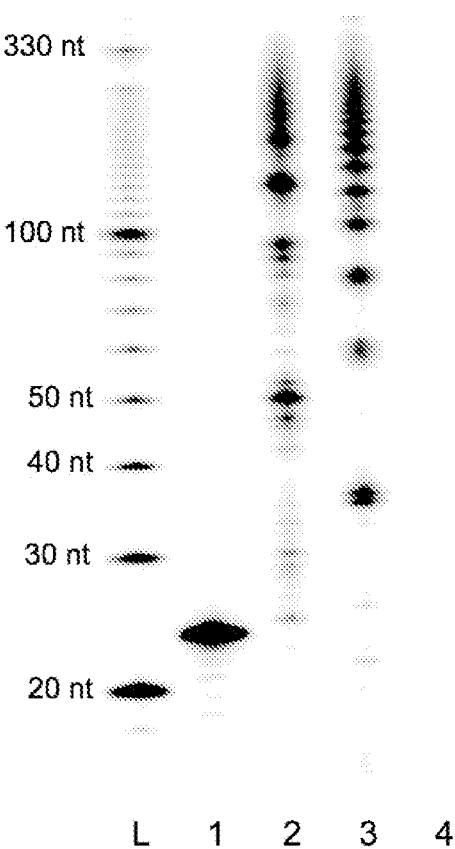

In some embodiments of the invention, the circularized RNA target is used as a template for rolling-circle reverse transcription (RT-RCA) which yields multimer cDNA in two steps: a) binding of circular target RNA with an oligonucleotide RT primer; and b) enzymatic extension of the RT primer by reverse transcriptase lacking RNAse H activity such as SuperScript II (FIGS. 2A and 29A-B). In certain embodiments of the invention, the RT primer is target-specific and contains a sequence substantially complementary to a region of the circular target RNAs, where in certain embodiments the complementary sequence is ≥6 nt in length, including from 8 to 18 nt in length. Since the maximum length of an oligonucleotide that can form a duplex with a small RNA circle is expected to be less than half the size of such a circle, one may expect that a small circular RNA would restrict the number of base pairs that could simultaneously be formed with an RT primer. However, we found that the efficacy of RT-RCA is not affected by the length of the RT primer as long as it can initiate the extension reaction. We demonstrated that 10, 12, 14 and 19 nt RT primers are equally efficient in RT-RCA of a 22 nt circular miRNA (see Example 3 and FIGS. 29A-B). However, we found that the overall efficacy of RT-RCA and yields of long multimer products for small circular RNA templates are comparatively small (see FIG. 29A). It is yet unclear why this is the case, but it is possible that small RNA circles disfavor either primer or reverse transcriptase binding. This result differs from RCA experiments with short and long DNA circle templates for DNA polymerases where long multimer products were predominant and were formed at high yields (Frieden et al. 1999).

In other embodiments of the invention, the RT primers are supplied as a mixture of fully or partially randomized oligonucleotide sequences, where in certain embodiments the oligonucleotides range from 6 to 10 nt in length. Although random primers are currently standard in many RT-PCR assays, they have several disadvantages in comparison to sequence-specific primers. A mixture of completely random primers of defined length comprises all possible sense and antisense sequences, and, therefore, could form numerous primer dimers that may produce primer multimer products that are not related to the targets. Also, random primers will extend on any RNA and DNA templates present in samples along with targets.

In some embodiments of the invention, small circular RNA targets can be used as a template for promoter-less transcription by an appropriate RNA polymerase that yields a multimer cRNA (FIG. 2B). The ability of recombinant viral RNA dependent RNA polymerases (RdRp) like HCV NS5BΔ21 to synthesize multimers of small (13-21 nt) circular RNA templates has been recently demonstrated (Ranjith-Kumar & Kao 2006). While it is known that DNA circles can serve as template for the promoter-less transcription by bacterial E. coli and bacteriophage T7 RNA polymerases (RNAP) (Frieden et al. 1999; Kool 2002), similar transcription reactions for small RNAs have yet to be reported. However, it is known that RNA can serve as template for RNA synthesis by bacteriophage T3 and T7 RNA polymerases (Leary et al. 1991; Arnaud-Barbe et al. 1998), although the transcription rate is lower than for DNA template strands.

In some embodiments of the invention, a multimer cRNA obtained by the transcription methods described above serves as a template for reverse transcription to synthesize a single copy of ccDNA strand in the following steps: a) binding an oligonucleotide RT primer that is substantially complementary to target antisense sequences; b) synthesizing ccDNA using RT; and c) degrading the cRNA strand by RNAse H or alkali treatment (optional step).

Figure 3C:
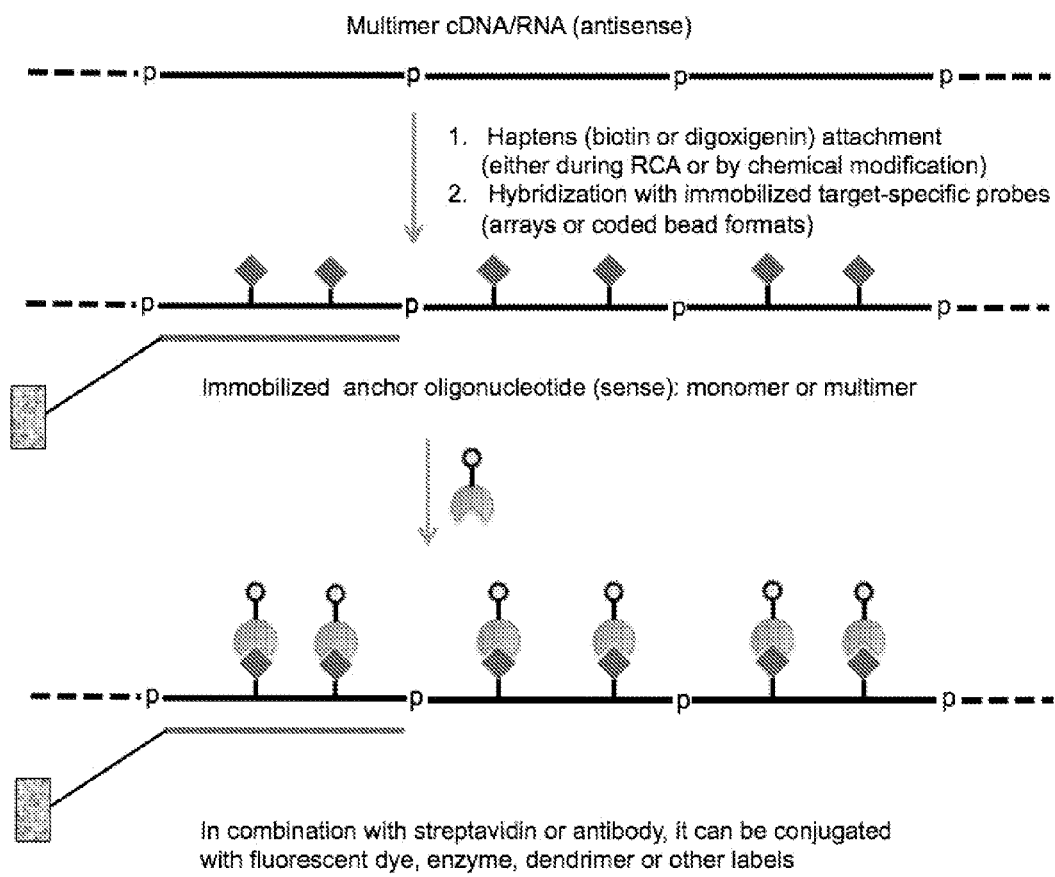
FIG. 3. Schemes for detection of a multimeric nucleic acid (see FIG. 2) using an anchor oligonucleotide probe or primer immobilized on a solid support. A: Capture of labeled multimer nucleic acids (MNA) by hybridization with target-specific anchor probes comprised of either monomers or tandem repeats of a sequence that corresponds to the target RNA. Labeling of the MNA can be accomplished either enzymatically (during reverse transcription for cDNA or transcription for cRNA) or by a post-transcriptional chemical modification. B: Capture of MNA by hybridization with a target-specific anchor probe that also serves as a primer, followed by primer extension using DNA polymerase (for cDNA) or reverse transcriptase (for cRNA) and simultaneous enzymatic labeling of ccDNA product. C: Capture of labeled MNA as in (A) but labeling is with haptens (e.g., biotin or digoxigenin) either enzymatically (during reverse transcription for cDNA or transcription for cRNA) or by a post-transcriptional chemical modification. The labeling is achieved through binding of the haptens with hapten-specific proteins (e.g. streptavidin or antibody) or aptamers conjugated with fluorescent or chemiluminescent tags, dyes, metal ions, enzymes, dendrimers or branched DNA (bDNA). D: Detection by sandwich-hybridization with oligonucleotide probes carrying either labels or haptens (including bDNA and dendrimers).
Figure 3D:
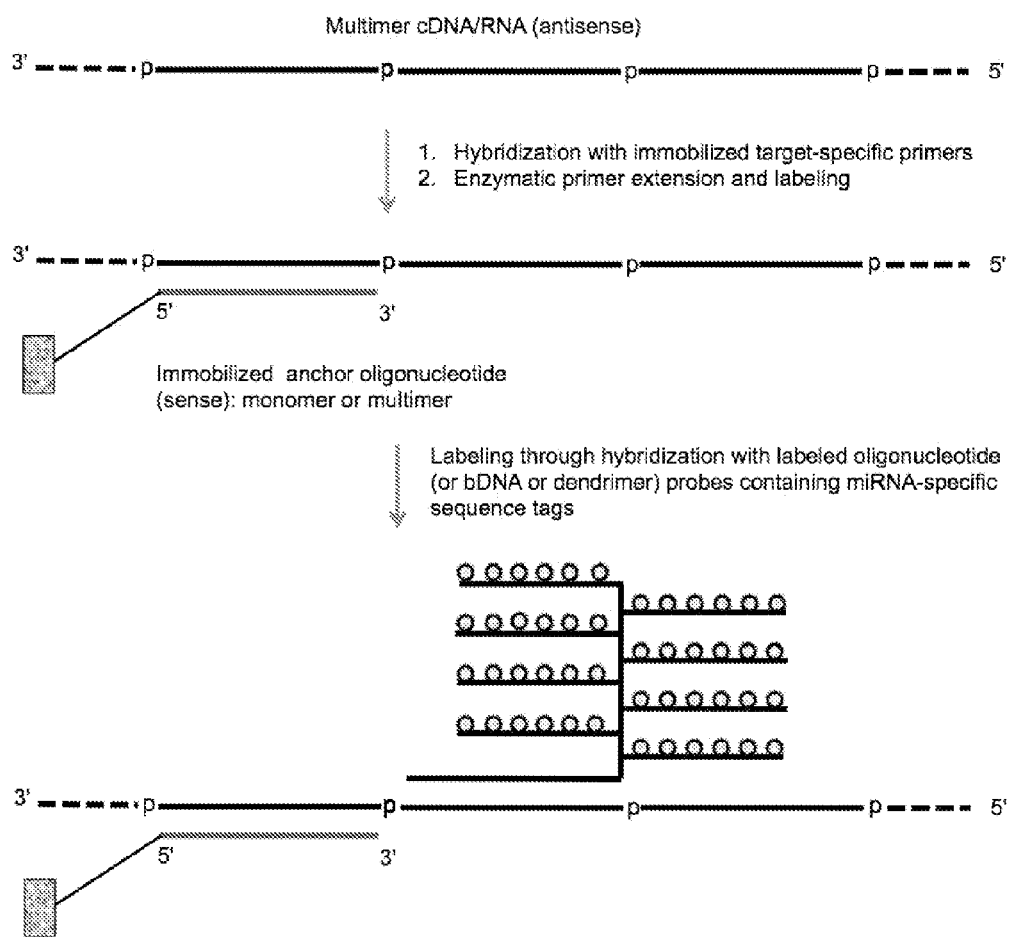
Figure 4A:
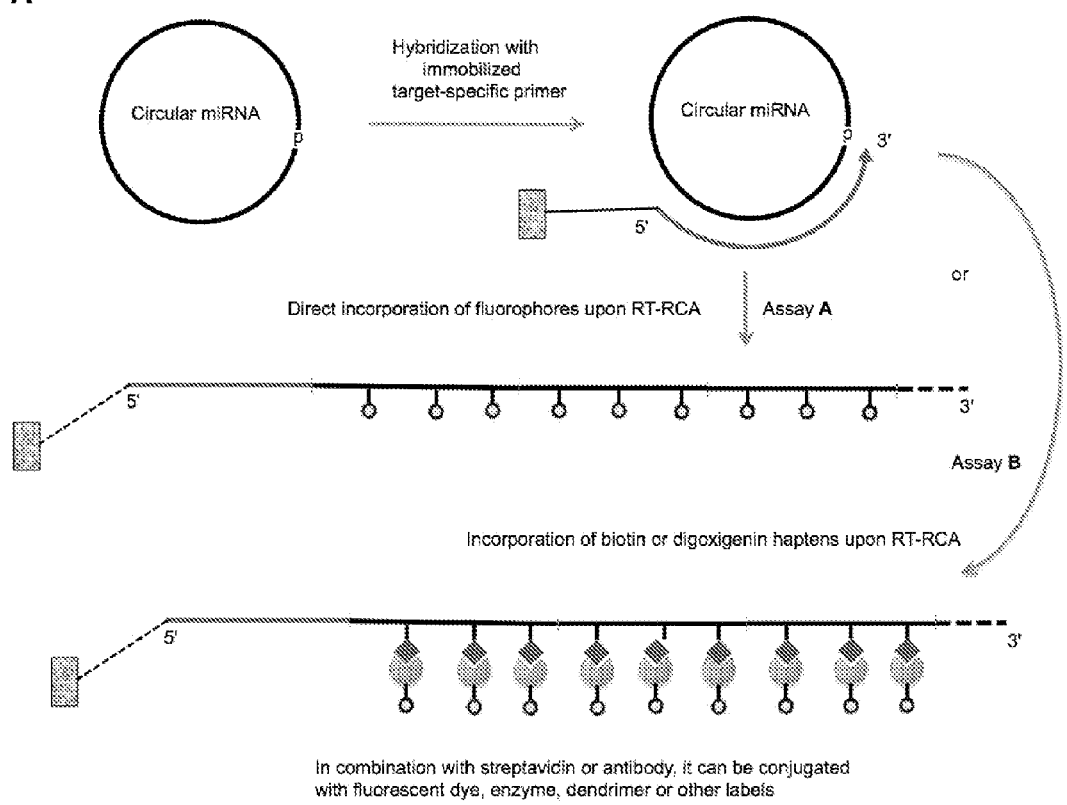
FIG. 4. Schemes for detection of small RNA circles using anchor oligonucleotide primers immobilized on a solid support (miRNA is shown as an example). A: Upon in vitro capture of circular target RNA by hybridization with the target-specific anchor probe, the RNA circle serves as a template and the anchor probe serves as reverse transcription (RT) primer. Rolling circle extension of the RT primer generates a multimeric cDNA strand consisting of tandem repeats of the complement of the small RNA, covalently attached to a solid support. Labeling of the multimer cDNA can be accomplished either enzymatically during reverse transcription (Assay A), or by hapten-assisted labeling (Assay B); or sandwich hybridization of the cDNA with target-specific signal probes (Assay C, not shown) as described in the legend to FIG. 3. B: In situ hybridization and RT-RCA using an RT primer complementary to the target miRNA circle. The RT-primers may have reactive groups (chemical of photochemical) at their 5' ends to allow immobilization of the synthesized multimeric cDNAs to the cellular matrix. Such immobilization may increase the detection sensitivity and specificity. The labeling of the target-specific multimeric cDNA can be accomplished as described above (in panel A). A sandwich hybridization assay is shown as an example.
Figure 4B:
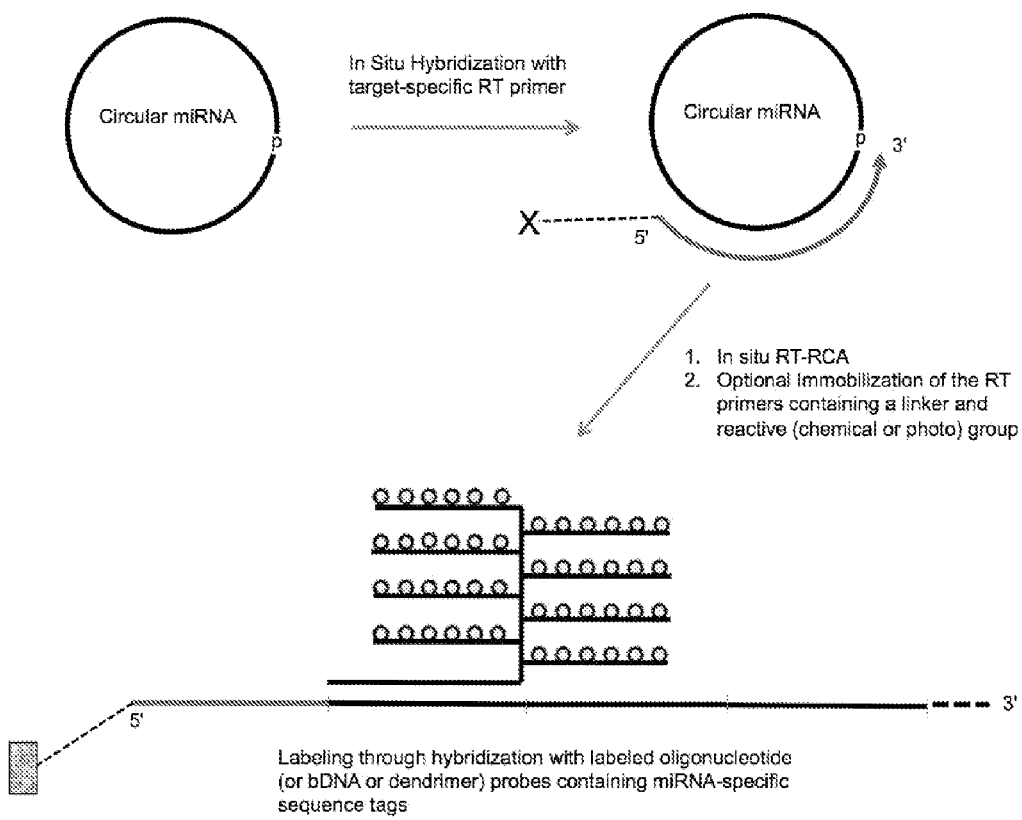

In some embodiments of the invention, the RT primers described above are not immobilized, and the synthesized cDNAs stay in solution, as is the case with the multimer cRNAs obtained by transcription methods. In other embodiments of the invention, the multimer nucleic acids synthesized in solution are subjected to affinity capture through non-covalent binding with substantially complementary anchor oligonucleotides immobilized on a solid support (FIGS. 3A, 3C and 3D). Optionally, the anchor oligonucleotide can be enzymatically extended to provide synthesis of yet another complementary multimer DNA strand which will be covalently attached to the solid support (FIG. 3B). In other embodiments of the invention, the RT primers described above are immobilized on a solid support and their enzymatic extensions provide direct covalent attachment of synthesized multimer cDNAs to the solid support (FIGS. 3B, 4A and 4B). Any convenient solid support can be employed, including solid supports selected from: beads (e.g. plastic, glass, magnetic or coded); membranes; filters; slides; microtiter plates; and microcapillaries.

In some embodiments of the invention, attaching the multimer cDNAs to a solid support (both non-covalent and covalent) can be use for purification and/or detection of the cDNAs. In contrast to purification, detection requires arraying (or attachment) of target-specific oligonucleotides to target-designated beads, or spots, or compartments on the solid surface/support. In certain embodiments of the invention, the target-specific oligonucleotides comprise stringency elements (chemical modifications or competitive secondary structures) to provide adequate sequence-specificity of binding to homologous target sequences.

In some embodiments of the invention, the synthesized multimer nucleic acids (MNA) are labeled and subjected to detection without further nucleic acid amplification. This approach is generally employed in the detection of relatively abundant small target RNAs, since small circular RNAs are not optimal templates for efficient signal amplification in comparison to conventional RCA methods that currently use exclusively circular DNA templates.

In some embodiments of the invention, a labeling method of the obtained multimer nucleic acids (MNA) is selected from: a) an enzymatic labeling either during MNA enzymatic synthesis (e.g., as shown in FIG. 3B) or after MNA synthesis; and b) a chemical labeling after the MNA enzymatic synthesis (e.g., as shown in FIG. 3A). Labels can be selected from: a radioactive isotope, a fluorophore, chemiluminescent moiety, a gold nanoparticle, a quantum dot, a hapten/ligand that can be recognized by antibody or aptamer conjugated with a signal-generating moiety (FIGS. 3C and 4A). These and other conventional labeling methods of MNA produced by RCA are known in the art (see Kool 2000).

In other embodiments of the invention, the MNA bound to a surface or solid support) (either covalently or non-covalently) is subjected to sandwich hybridization with signal oligonucleotide probes, which are substantially complementary (or corresponding) to either target or adapter sequences. The signal oligonucleotide probes are labeled before or can be labeled after hybridization (e.g., as shown in FIG. 4). In certain embodiments, the signal probes, which are complementary to target sequences, also comprise stringency element(s). In some embodiments of the invention, the unlabeled signal oligonucleotide probe contains additional universal sequences that are complementary to a secondary, labeled nucleic acid probe, such as branched DNA (bDNA) or DNA dendrimer (FIG. 3D).

In certain embodiments of the invention, cellular miRNAs can be detected by in situ hybridization and RT-RCA using RT primers complementary to the circularized form of the target miRNA. RT-primers having reactive groups (chemical of photochemical) at their 5' ends can provide immobilization of the synthesized multimeric cDNAs (consisting of tandem repeats of the sequence complementary to the small RNA) to the cellular matrix. Such immobilization may increase the sensitivity and specificity of detection. Labeling of the target-specific multimeric cDNA can be accomplished as described above. A sandwich hybridization assay using bDNA or dendrimers is shown as an example in FIG. 4B.

In certain embodiments of the invention, the synthesized multimer nucleic acids (MNA) are subjected to detection by real-time qPCR without the need for TaqMan probes. This approach allows detection of both abundant and low-copy number target RNAs because of its increased sensitivity. For this approach, the MNA synthesis is a way of making tandem repeats of target sequences rather than target sequence amplification. The repetitive target sequences present several advantages as described below.

In some embodiments of the invention, the RT primer also serves as a reverse PCR primer along with additional forward PCR primer, whereas in other embodiments the RT primer has a different sequence from the PCR primers. In certain embodiments of the invention, multiple circular target RNAs are reverse transcribed simultaneously in multiplex format (Example 11 and FIG. 37) using short (8-10 nt) target-specific RT primers that differ from the longer PCR primers. This approach presents several advantages: 1) the specificity of RT-PCR is increased because only those RNAs that contain a sequence complementary to the RT primers are reverse transcribed; and 2) the short sequence-specific RT primers do not need to be removed because they do not bind to the target or to other (even complementary) primers at the higher temperatures used for PCR.

Optionally, MNA can be subjected to affinity purification by capture on immobilized anchor oligonucleotides (e.g., on magnetic beads) and separation from the irrelevant nucleic acids (e.g., by washing) before PCR. This step serves to further reduce background and increase assay sensitivity.

The structure of small circular RNA targets and their corresponding multimer nucleic acids (MNA) provide unmatched flexibility in design of conventional RT and PCR primers in comparison to small linear RNA targets. For the linear targets, only a pair of short sub-optimal primer sequences that are not overlapping at their 3' ends can be used (e.g., as shown in FIG. 5A). As such, the combined length of these primer sequences is equal or shorter than the target size (for miRNA it is 19-24 nt). Since the majority of small RNA targets have different GC-contents at their 5'- and 3'-end sequences, it is problematic to design such primers that can be simultaneously efficient and sequence-specific. In contrast, primers for MNA templates allow shifting the primer sequences along a border of the monomer sequence unit, and allows the use of longer primers that can overlap (be complementary and form a dimer) at their 5'-ends (see FIGS. 5B and 6B). This allows design of primer pairs with more favorable/compatible $T_m$ and, therefore, efficacy of PCR (especially when many different targets are assayed simultaneously). The longer primers also allow using increased temperatures for primer annealing and extension steps that may improve specificity of the target sequence PCR amplification. FIG. 5C depicts exemplary structures for allowed (overlapping at their 5' ends) and non-allowed (overlapping at their 3' ends) primer-dimers. The 5'-overlapping primers are not normally extendable by a polymerase, whereas 3'-overlapping primers can extend and provide target-independent signal amplification (increase background noise reducing the assay sensitivity (Brownie et al. 1997). However, short ($\leq 2$ nt) overlaps of the primers at 3'-ends could be used occasionally since 1-2 bp duplexes are not stable under usual "hot-start" primer annealing and extension conditions (Raymond et al. 2005).

Figure 6B:
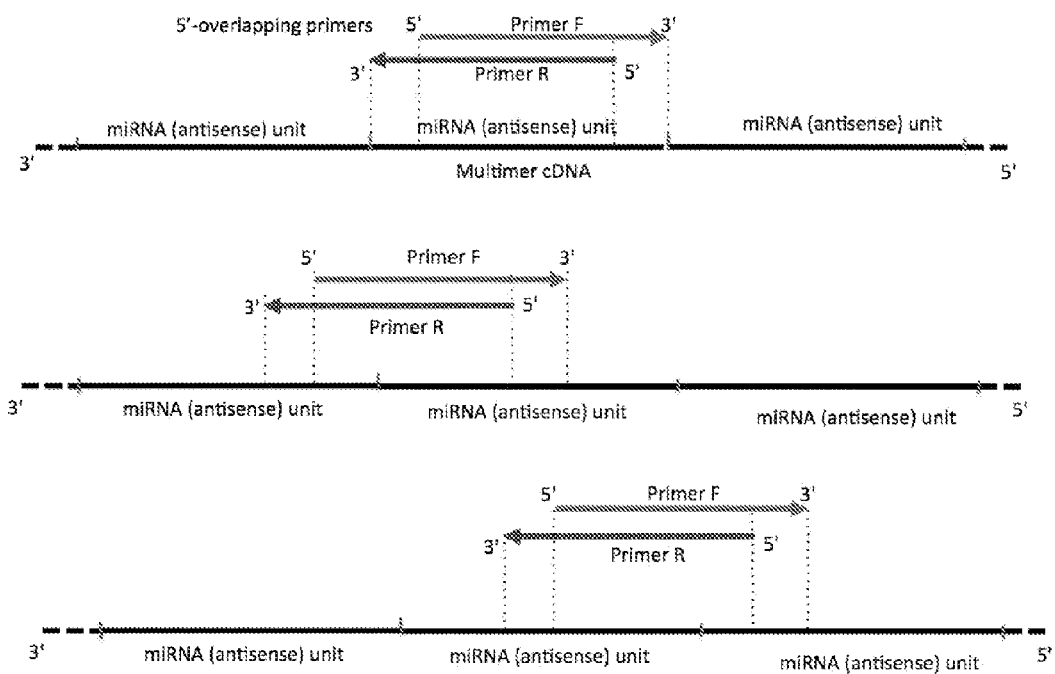

In certain embodiments of the invention, PCR of multimer cDNA is performed using a pair of forward and reverse primers that: a) overlap (are substantially complementary to each other and form a dimer) at their 5' ends and have non-overlapping overhangs at their 3' ends; b) are complementary or correspond to overlapping segments of a repetitive target sequence; and c) form a more thermostable duplex with their respective target sequences than with each other. In certain embodiments of the invention, the 5'-end overlap is at least 2 nt shorter than the target sequence while the 3'-end overhangs are at least 1 nt long. The tandem target sequences allow either keeping the alignment of primer sequences within the target sequence or shifting it across the target ends (FIG. 6B).

The 5'-end overlapping dimer-primers provide several advantages for amplification of short repetitive sequences over conventional (i.e., non-overlapping) RT and PCR primers used for amplification of short linear sequences:

(1) The dimer-primer target binding sites can be easily shifted along sequences of circular and multimer targets to adjust $T_m$ (melting and annealing temperature) and sequence specificity of the primer extension. Similar alignment changes with small linear target sequences are hardly possible for either conventional primers or the dimer-primers.

(2) For conventional RT-PCR primers, the segments that are complementary to a short linear target must likewise be very short. This limiting length requires reduced temperatures for their hybridization and extension which may result in sub-optimal efficacy and specificity of RT and PCR reactions. For tandem arrays of short target sequences, the dimer-primers can form substantially longer duplexes with the target, providing more efficient and specific amplification than conventional primers.

(3) The duplex structure of dimer-primers (formed via interaction of their complementary 5'-end overhangs) provides enhanced sequence-specificity of PCR by discriminating against partially complementary and mismatched non-target sequences (including single nucleotide polymorphisms [SNPs]) if they are present in samples with target sequences. For mismatch discrimination, the primers will form more thermostable duplexes with intended target sequences than with mutants/variants.

(4) Since the duplex structure of a dimer-primer must be melted before it can hybridize to a complementary target strand, such primers can provide "hot start" for every PCR cycle without the need for special enzymes or other tricks that are otherwise required (Kong et al. 2004). "Hot-start" PCR minimizes non-specific primer annealing and extension at low temperatures.

(5) The duplex structure of dimer-primers with short single-stranded overhangs also limits interaction with other dimer-primers allowing more targets to be assayed simultaneously in a multiplex format (FIG. 13A).

(6) Dimer-primers for RT-PCR of tandemly repeated short target sequences are ordinary, low-cost DNA oligonucleotides, and their design and optimization can be done using available techniques in the art.

Double-stranded PCR primers composed of a "primer strand" and a non-extendable "competitive" strand have been described (see Li et al. 2002; Kong et al. 2004). However, these double-stranded primers differ from those described herein in significant aspects. In these reports, two different sets of double-stranded primers were used for PCR amplification of target regions located between these primers. The Li et al. and Kong et al. primers employ a displacement hybridization mechanism, but they differ from our dimer-primers since only one strand of the double-stranded primers serves as a primer for extension of the target nucleic acid while the other strand of the double-stranded primer hybridizes with non-overlapping target sequences.

5'-overlapping PCR primers used for site-specific mutagenesis and splicing or shuffling of sequences of long double-stranded DNA have been described (Thisted 2003; Vallejo et al. 1994). The Thisted primers were designed to include a site-specific mutation in both strands of a nucleic acid encoding a gene of interest, whereas the Vallejo et al. primers were designed to remove certain DNA sequences or paste together certain DNA sequences using PCR. In both of these cases, the 5'-overlapping primers were employed to produce non-repetitive PCR products rather than for the amplification and detection of specific repetitive sequences as described herein. Our RT-PCR dimer-primer provides amplification of short repetitive (such as circular and multimer) sequences as well as any sequences inserted between these repeats.

We compared the efficacy of RT-PCR (in conventional format) with 5'-overlapping dimer-primers for circular and linear miRNA target (see Examples 4). In each experiment, an 18 nt RT primer was used for both rolling circle reverse transcription of circular let-7b miRNA target (CT) and for PCR of generated multimer cDNA as reverse PCR primer along with 18 nt forward PCR primer. First, we tested the target-primer alignment schemes shown in FIG. 6C, and found that the dimer-primers provide efficient RT-PCR amplification of multimeric but not monomeric templates when the primers are aligned with target sequence (FIG. 30). Different small RNA targets require different alignment schemes for optimal performance (combination of efficacy and sequence-specificity of signal amplification by PCR). Using higher annealing temperature and lower initial concentrations of PCR primers can provide preferential PCR amplification of multimer templates (rather than a monomer template) and lower background and increase sensitivity of the circular RNA detection.

Figure 7:
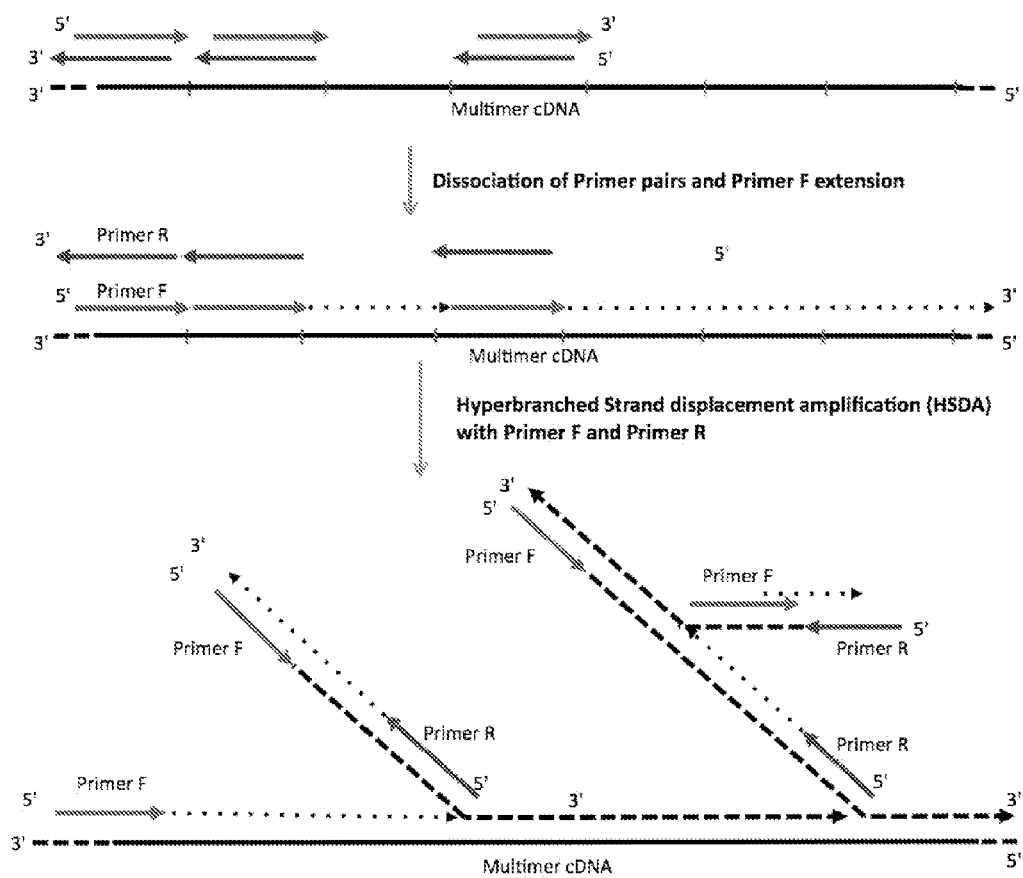
FIG. 7. Scheme for hyperbranched strand displacement amplification (HSDA) of multimeric cDNA consisting of tandem repeats of the small RNA complements using 5'-overlapping primers. This amplification scheme shares common elements with the previously described hyperbranched RCA (HRCA) mechanism (Lizardi et al. 1998; Zhang et al. 2001), but differs from HRCA in several important aspects: (1) HSDA uses 5'-overlapping primers whereas HRCA uses non-overlapping primers; (2) there is no RCA amplification in this scheme; and (3) HSDA may occur simultaneously with overlap extension (described in FIG. 8). The primer positions shown here may vary as shown in FIG. 6B.

In certain embodiments of the invention, PCR amplification can be substituted by isothermal hyperbranched strand displacement amplification (HSDA) for amplification of multimeric cDNA using 5'-overlapping primers (FIGS. 7 and 41; and Example 14). This amplification scheme shares common elements with the previously described hyperbranched RCA (HRCA) mechanism (Lizardi et al. 1998; Zhang et al. 2001), but differs from HRCA in several important aspects: (1) HSDA uses 5'-overlapping primers whereas HRCA uses non-overlapping primers; (2) there is no RCA amplification in this scheme; and (3) HSDA may occur simultaneously with overlap extension (described in FIG. 8).

Figure 8:
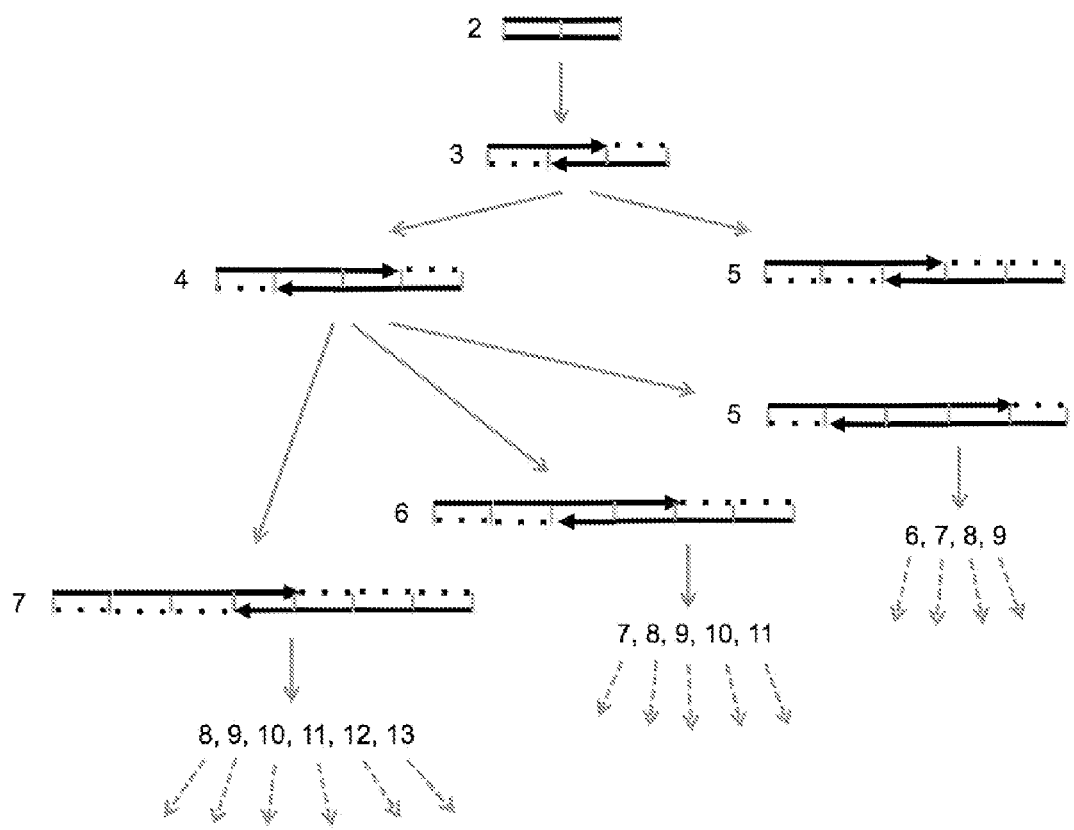
FIG. 8. Scheme of PCR-assisted multimerization of repetitive DNA sequences. Target-specific signal amplification by "primer-less" PCR with DNA multimers. Here, DNA multimers serve both as PCR template and PCR primers. After thermal denaturation, multimeric single-strands can reanneal such that they are shifted in alignment by one or more repeat units. Subsequent extension of recessed 3' ends generates longer multimers. Each PCR cycle provides progressive elongation of the multimers. This overlap extension PCR (OE-PCR) mechanism was previously described (Hemat & McEntee, 1994) but for synthetic purpose only. We estimate that this process can provide an additional 1.5-fold amplification per PCR cycle in comparison to ordinary exponential PCR.

We also found that multimer nucleic acids are generated not only by RT-RCA of circular templates but also by PCR of multimers themselves. Moreover, we observed longer multimer products occurring with increased of numbers of PCR cycles (see FIG. 30). Using higher annealing temperature and lower initial concentrations of PCR dimer-primers promote this process while providing lower background noise (amplification of target-independent products). The proposed elongation schemes are shown in FIG. 8.

We also found that target-specific DNA multimers could provide signal amplification without PCR primers present. In this case, DNA multimers serve both as the PCR template and subsequent PCR primers. Upon thermal denaturation and reannealing, multimeric single-strands anneal to each other with a shift. Extension of these shifted strands results in synthesis of longer multimers. As such, each PCR cycle results in progressively longer multimers. If "n" is the number of repeats in a multimer before the elongation, then the sizes of corresponding multimer products after each PCR cycle would vary from (n+1) to (2n−1), where the number of the formed multimer species will be (n−1) and their total size will be 1.5−n−(n−1). Therefore, an average multimer enlargement will be 1.5 per PCR cycle. The OE-PCR takes place when PCR primers are absent or available in limiting amounts—for example due to planned consumption during initial PCR cycles. This PCR variant can provide higher sensitivity than known in the art linear-after-exponential PCR (LATE-PCR) (Wangh et al. 2004; Pierce et al. 2005).

Previously, it was shown that multimer DNA templates subjected to conventional PCR with pairs of template-specific primers could generate longer multimers by similar reactions known as concatamer chain reaction (CCR) or overlap extension PCR (OE-PCR) (White et al. 1991; Hemat & McEntee 1994; Vallejo et al. 1994; Schellenberger 1998; Zhang et al. 1998). However, prior to this invention, no one has suggested using double-stranded multimer DNAs for signal amplification by PCR. Using small, limiting amounts of either a single forward primer or both forward and reverse PCR primers could significantly reduce background noise, thereby increasing detection limits.

Figure 9:
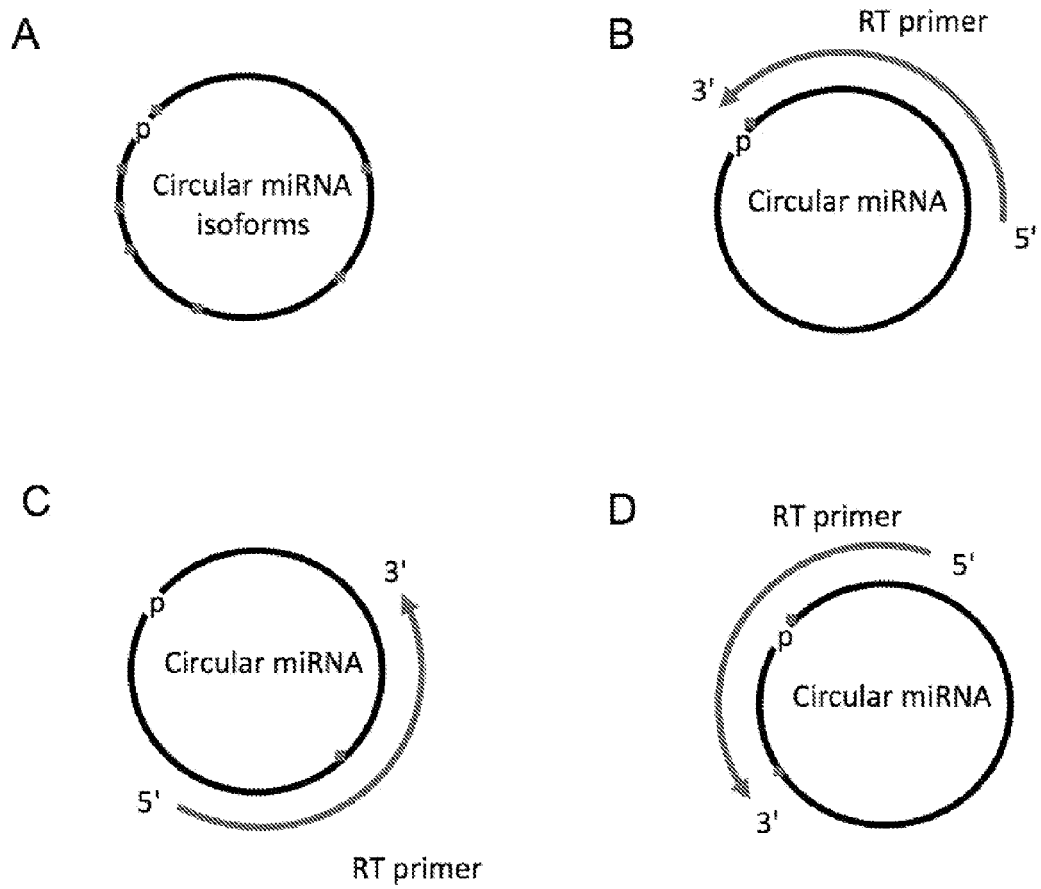
FIG. 9. Examples of RT primer designs for improved discrimination of homologous miRNA sequences at the RT-RCA step. A: Circularized human let-7 miRNA, with red dots indicating sites of nucleotides that differ among members of the let-7 family. B: Discrimination of these single nucleotide polymorphisms (SNP) using a primer whose 3' end is positioned opposing the SNP. C: Discrimination of the SNP using a primer positioned so as to provide the largest difference in $T_m$ for binding with matched vs mismatched targets. D: Combining schemes B and C can increase the discrimination between targets differing at two polymorphic sites. Besides increasing sequence specificity, the ability to adjust the alignment between templates and primers can also be used to optimize the efficiency of reverse transcription initiation (see FIG. 2A).

Another advantage of continuing repetitive target sequences over small monomer target sequence is the discrimination of the homologous sequences. For example, certain miRNA "families" comprise isoforms with mismatches, deletions and different lengths as shown in FIGS. 10A and 33A for the let-7 family. In general, RT and PCR primers can discriminate the homologous sequences through either: selective hybridization, i.e. when a correct sequence binds a target more strongly (has higher $T_m$) than an incorrect one; or selective primer extension, when only primers with correct 3' ends facing a complementary nucleotide in the target sequence can be extended. By contrast, non-complementary nucleotides at the same position in a mutant target will inhibit the primer extension and its PCR amplification. For a monomer miRNA sequence, the ability to adjust the relative positions of sub-optimal primers along the target sequence is very limited (FIG. 10B). Since 5'- and 3'-end sequences usually have different GC-contents, it is problematic to design PCR primers that can simultaneously be sequence-specific and provide efficient PCR amplification of different target sequences under the same conditions. In contrast, MNA templates allow shifting the primer sequences along a border of the monomer sequence unit, and use of longer primers, which can overlap at their 5'-ends if necessary, to both adjust their $T_m$ and place primer 3' ends at the positions opposing mismatches (FIG. 10O) to overcome this limitation. Because of the improved efficacy and sequence-specificity of the PCR amplification of the multimeric target sequences, real-time qPCR assays can be carried out without the need for expensive TaqMan probes. Similar to PCR primers designed for homologous MNA templates, circular miRNA targets also provide flexibility in shifting the positions of RT primers for optimal discrimination of the mismatches (FIG. 9).

In certain embodiments, the presence of small target RNAs is detected and their amounts quantified by the miR-ID approach using the following steps: a) multiplex circularization of target RNAs using T4 RNA ligase 1 or CircLigase (FIG. 1A); b) multiplex synthesis of the corresponding multimers (MNA) by RT-RCA using a mixture of short (8-10 nt) target-specific RT primers and a reverse transcriptase (FIG. 2A); c) singleplex real-time qPCR using target-specific 5'-overlapping primers (which overlap for 13-19 nt at their 5'-ends and have 2-4 nt overhangs at their 3' ends). An inexpensive, non-specific fluorescent dye such as SYBR Green or EVA Green can be used for signal detection. The qPCR step can be performed simultaneously for any number of different miRNAs under the same thermo-cycling conditions in the so-called "PCR array" or "virtual array" formats. These "virtual multiplexing" techniques, which use physically separated PCR primers specific to different miRNAs, are easy to automate and can compete with true multiplex qPCR methods.

The development of true multiplex PCR represents a technological challenge because of overlap in the emission spectra of available fluorescent dyes. Currently, at most six dyes can be assayed simultaneously within the same sample. Moreover, conventional PCR primers specific to different targets tend to form dead-end dimers (FIG. 5C) when mixed and extended together. In this respect, the 5'-overlapping primer pairs used in miR-ID have an advantage because their double-stranded structures can greatly reduce the cross-hybridization between different primer pairs and targets.

Figure 38B:
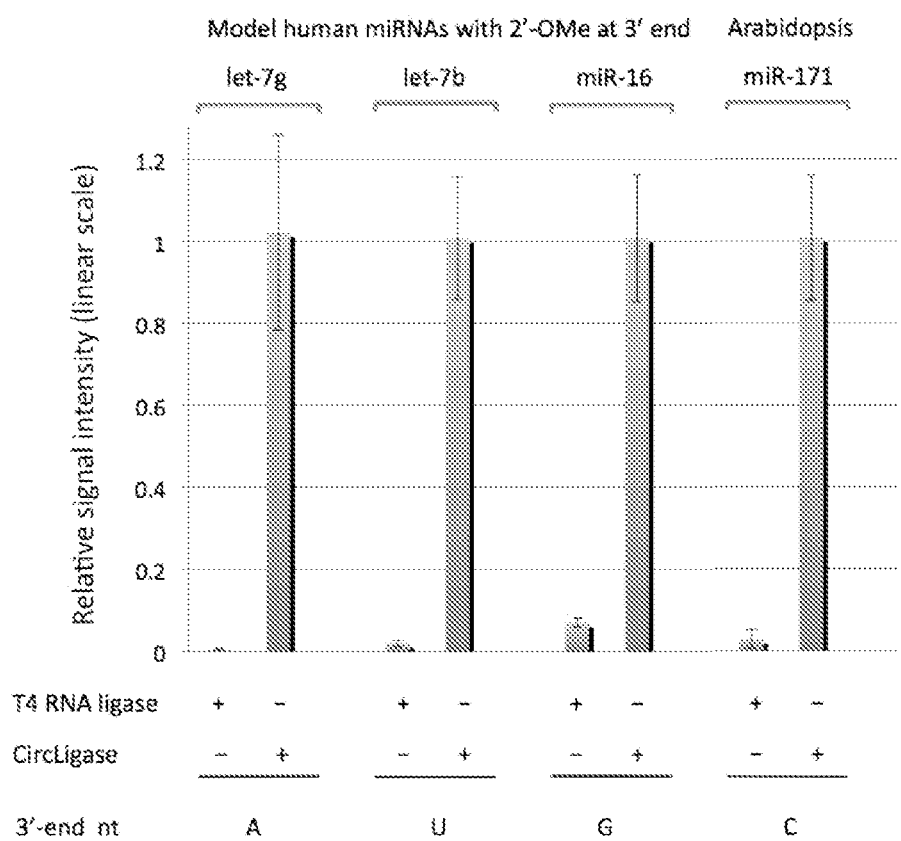
Figure 38C:
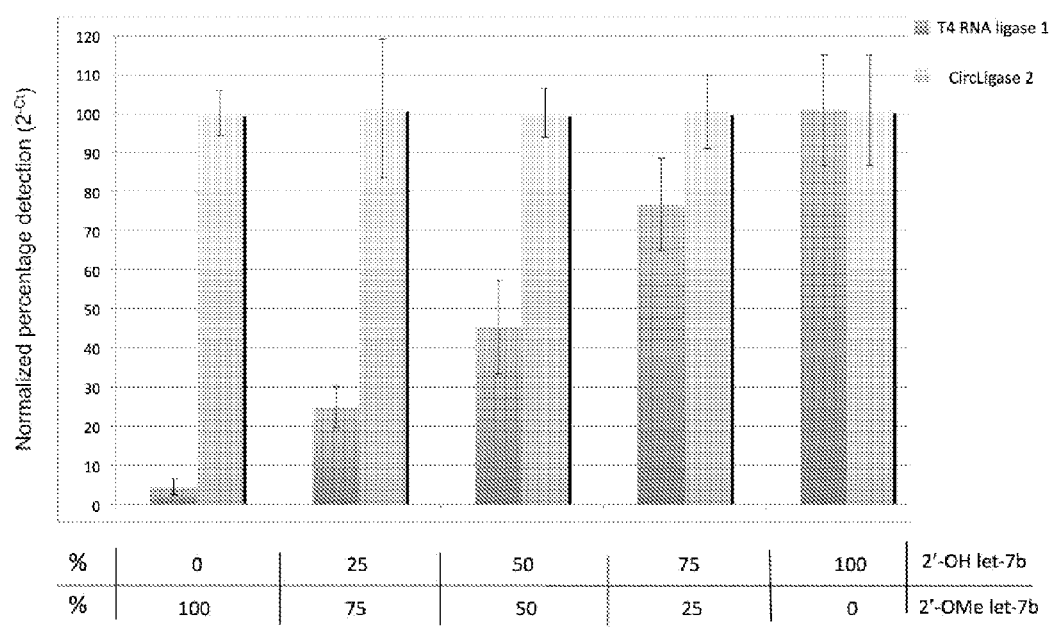

In certain embodiments, modified 5'-overlapping primers can be used for multiplex miR-ID assays. The modifications can be reporter dyes that have non-overlapping emission spectra together with and quenchers, incorporated either directly in the PCR primers or in TaqMan® probes complementary to the primers. The reporter dye should be quenched (and therefore not detectable) unless it is physically separated from the quencher as result of the primer extension or probe degradation. An example of such a design, with one member of the 5'-overlapping primer pairs having a reporter dye and the other a quencher positioned opposite the reporter dye, is shown in FIG. 13A.

miR-ID assays have been demonstrated to have superior sensitivity. For example, a comparison of standard curves for detection of lin-4 miRNAs by miR-ID and TaqMan RT-PCR microRNA assays (FIG. 31A and Example 5A) shows that miR-ID is about 30 times more sensitive than the TaqMan assay ($\Delta Ct=5$; $2^5=32$). The superior sensitivity of miR-ID is can be explained by the additional signal amplification provided by RT-RCA and OE-PCR. In an alternative miR-ID assay (FIG. 31B and Example 5B), which use T4 RNA ligase 2 instead of T4 RNA ligase 1, we achieved even higher sensitivity than for the original miR-ID assay. This alternative approach may have limited application since not all miRNAs can be circularized by splint-assisted ligation. However, this approach allows simultaneous circularization and RT-RCA reactions that may have certain advantages (such as higher sensitivity and shorter assay time) for assaying appropriate miRNA targets.

miR-ID has also been demonstrated to have superior sequence-specificity compared to other micro-RNA assays. As an example, we assayed five let-7 isoforms (FIG. 33A) in a cross-reaction manner where every miRNA isoform was subjected to each isoform-specific primer set (FIG. 33 and Example 7). miR-ID easily discriminated miRNA species that differ by as little as 1 nt, with stronger discrimination between isoforms than other RT-PCR methods commonly used for miRNA detection. We also showed that miR-ID can specifically detect mature miRNA in the presence of pre-miRNA (FIG. 34 and Example 8). The high specificity of miR-ID allows detection of specific miRNAs in total RNA (FIGS. 35-37 and Examples 9-11) and cell lysates (FIG. 36B and Examples 10B).

miR-ID also can detect small RNAs carrying either 2'-OH and 2'-OMe groups at their 3' ends RNAs and can distinguish these two forms from each other. For these purposes, we use the similar ability of CircLigase and T4RNA Ligase 1 to circularize the 2'-OH miRNAs but significantly different abilities of these enzymes to circularize the 2'-OMe miRNAs (FIG. 38 and Example 12). The discrimination between these miRNA forms is not significantly affected by variations in the 3' end nucleotides (FIG. 38B).

Figure 41A:
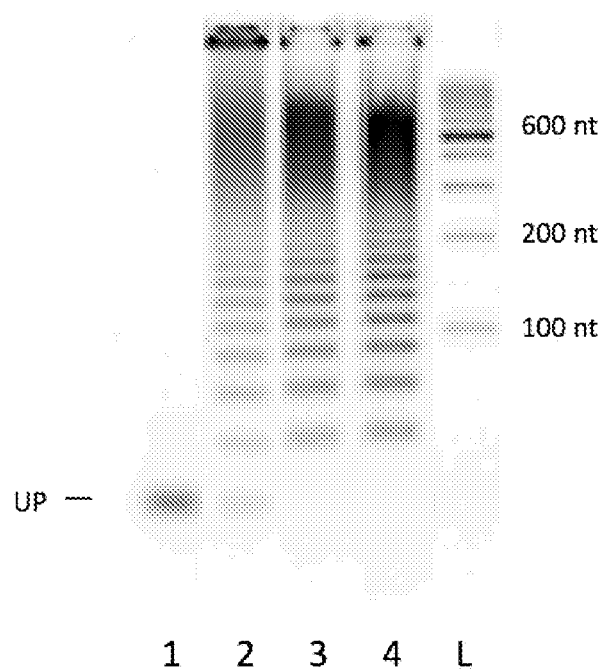

Yet another variant of miR-ID, uses an isothermal technique instead of PCR for signal amplification (miRSA assay). This method shares the same circularization (FIG. 1A) and RT-RCA steps (FIG. 2A) with miR-ID, but differs in step 3. In this last step, miRSA uses the isothermal, hyperbranched strand-displacement (HSDA) reaction (FIG. 7) rather than PCR (FIG. 6A). while both methods employ similar 5'-overlapping primer pairs. A comparison of the standard curves obtained by miRSA and miR-ID assays indicates that they provide very similar sensitivities, which are about 30 times better than that of ABI's TaqMan assay (FIG. 41A and Example 14A). Analysis of the discrimination between the let-7 isoforms assayed in a cross-reaction manner demonstrated that miRSA provides superior sequence-specificity (FIG. 41B and Example 14B), even in comparison to miR-ID (see FIG. 33B).

Figure 11B:
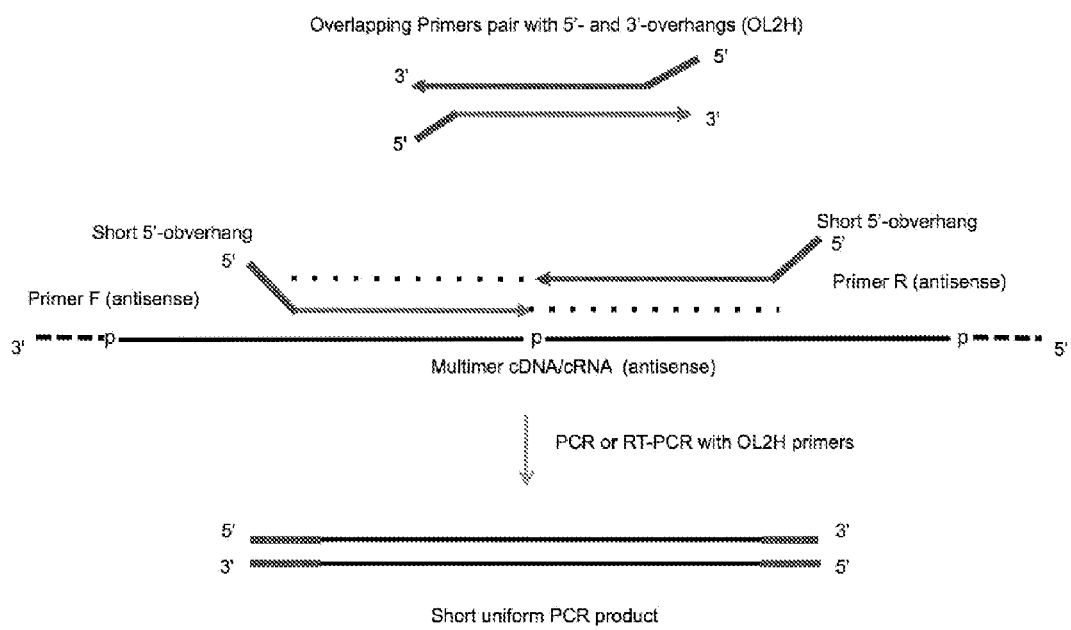

In other embodiments, the RT and/or PCR primers are combo primers that comprise target-specific sequences at their 3' ends and additional sequences at their 5' ends (e.g., as depicted in FIGS. 11-12). The target-specific sequences can substantially overlap at their 5'-ends as shown in FIGS. 5-6 if necessary to improve efficacy and specificity of the primer extensions. The combo primers are used for the first few rounds of conventional PCR, while another set of two PCR primers, which correspond to the additional sequences, is used for real-time qPCR. In some embodiments, only PCR primers are combo primers (FIG. 11A) whereas in other embodiments, both RT and PCR primers are combo primers (FIGS. 12A-B). In certain embodiments of the invention, the additional sequences are Zip-code sequences, e.g., when an RT-PCR assay is used for detection of known small RNA targets, e.g. biomarkers (FIGS. 11A, 12).

In yet another embodiment, combo primers with short (1-5 nt) additional sequences can be used for optimization of primer $T_m$ as well as to prevent overlap-extension amplification (if necessary) (FIG. 11B) Such primers are used in the first few PCR rounds at a lower annealing temperature (based on the target specific sequence), followed by increasing the annealing temperature (based on the entire primer length, including the 5' overhang sequence) for the remaining cycles.

Figure 13B:
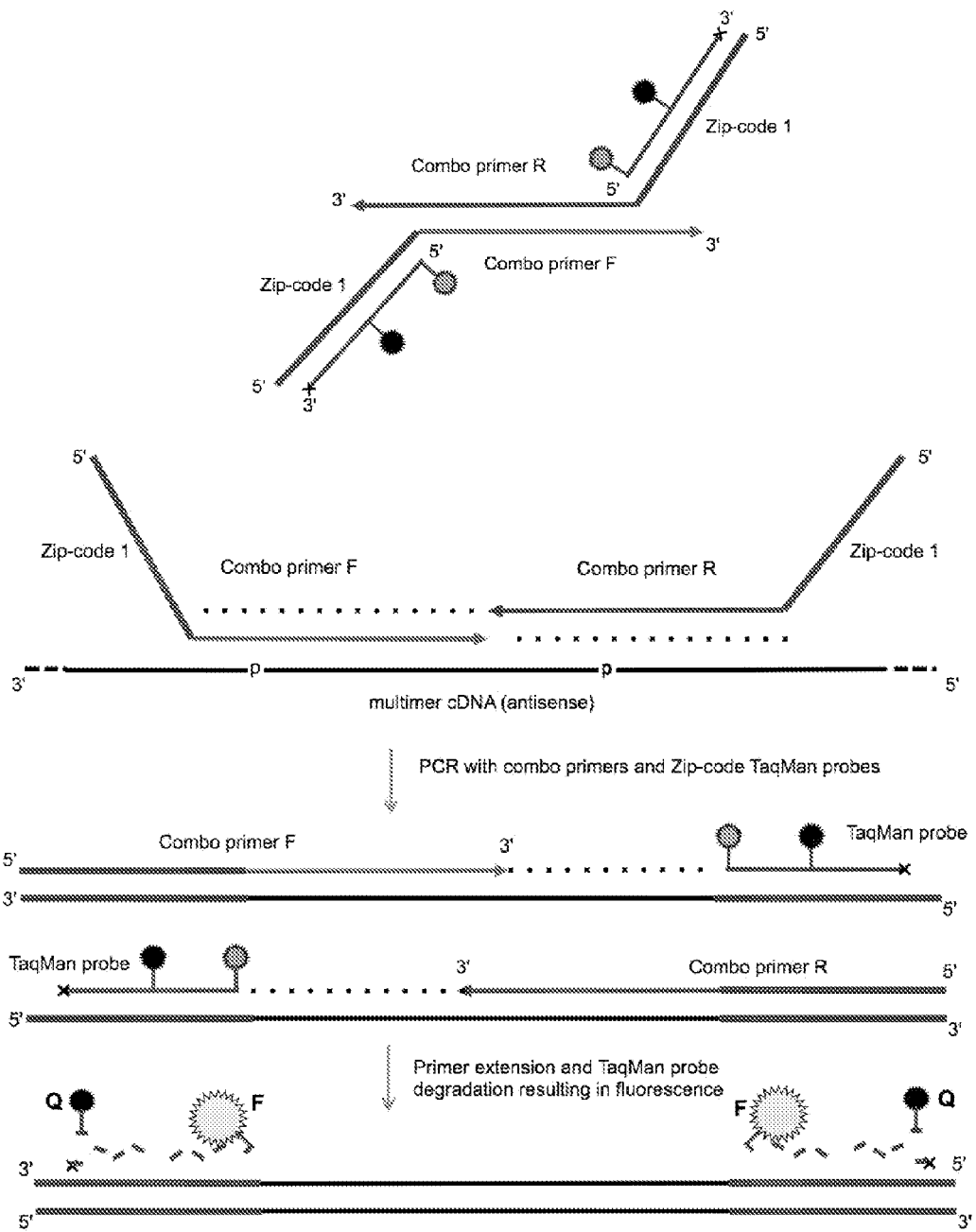
FIG. 13. Schemes allowing multiplex miR-ID assays with modified 5'-overlapping PCR primers. Multiplex assays can be performed using appropriate reporter dyes, which have non-overlapping emission spectra, and quenchers incorporated either directly in the PCR primers or in TaqMan probes complementary to the primers. The reporter dye and quencher incorporated in the primer/probes should prevent the signal in such manner that there are not separation These primer/probes should be detectable only when reporter dye and quencher are physically separated as result of the primer extension and/or probe degradation. Examples of such primer-probe designs are shown below. A: Default 5'-overlapping primer pairs having a reporter dye and a quencher incorporated in the opposite primer strands. B: Overlapping combo primers used along with custom TaqMan probe complementary to the Zip-code sequence designated to specific target small RNA. Both reporter dye and quencher are incorporated in the TaqMan probe. C: Overlapping combo primers used along with second probe strand complementary to the Zip-code sequence designated to specific target small RNA. A reporter dye and quencher are incorporated in the opposite strands. D: Overlapping combo primers that have hairpin additional sequence at their 5'ends. There is no Zip-code sequences or separate probe strands. Both reporter dye and quencher are incorporated in the hairpin structure. The signal detection in A, C and D should be performed at under low temperature conditions providing stability for the duplex structures whereas in B, the TaqMan probes emitting signal upon their degradation have no such requirement.
Figure 13C:
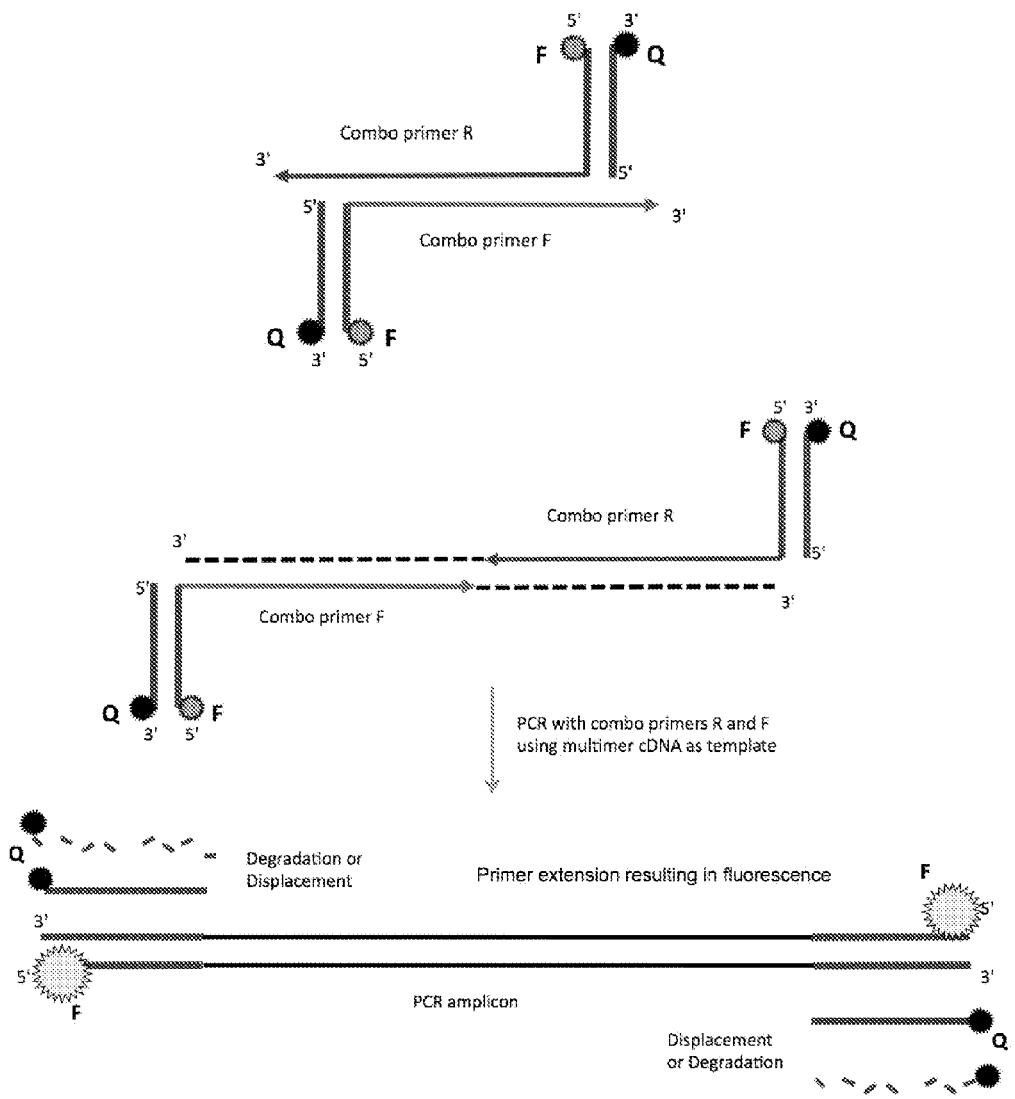
Figure 13D:
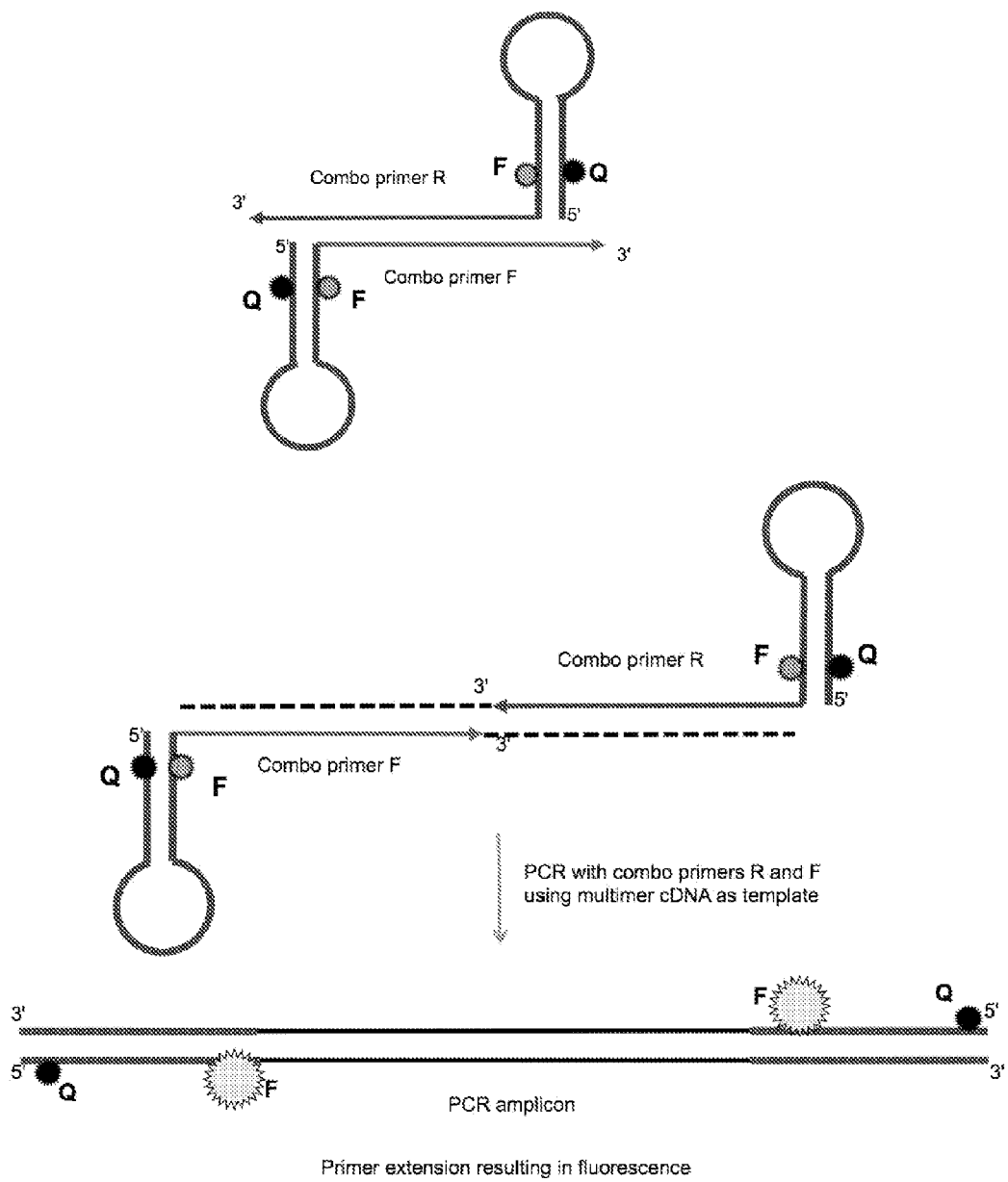

In another embodiment, overlapping combo primers can be used in combination with universal TaqMan probes complementary to the Zip-code sequence designated to specific target small RNA (Example 13, FIGS. 13B and 40). A similar primer-probe design also can be used in multiplex assays. There are other examples of overlapping combo primer-probe designs amenable to multiplex assays, including: (1) primers used along with a second probe strand complementary to the Zip-code sequence designated to specific target small RNA, in which a reporter dye and quencher are incorporated in the opposite strands (FIG. 13C); and (2) primers that have an additional hairpin sequence at their 5'ends, in which both reporter dye and quencher are incorporated in the hairpin structure (FIG. 13D).

However, both known and unknown small RNAs can also be assayed by cloning and sequencing (including next-generation sequencing)—in this case, the adapter sequences are sequencing adapters or linkers (FIG. 11A). In general, the adapter sequences could comprise certain sequences that are not substantially complementary or corresponds to any sequence that can be present in the sample.

A wide range of PCR cycles using combo primers can be employed in practicing this aspect of the invention. As described in Example 6 below and shown in FIG. 32, we found that 7 cycles of PCR pre-amplification with combo primers works well. This step provides 128-fold amplification of the target sequence before PCR with the Zip-code primers. We also demonstrated that this approach allowed perfect discrimination between both unrelated small RNAs (Example 6 and FIG. 32).

In some aspects of these methods, an adapter (or linker) is ligated to the RNA target before the circularization. In certain of these embodiments, the following steps are performed: a) ligating an adapter oligonucleotide to the target RNA in a sample producing an extended target polynucleotide (or target-adapter conjugate); b) circularizing the extended target polynucleotide by ligation of its 5'- and 3'-ends; c) synthesis of MNA comprising multiple repeats of sequences that are complementary to the target RNA and the adapter by RCA; d) assaying for the presence of the MNA, thereby detecting the presence of the target RNA in the sample. In certain embodiments of the invention, the circularization of a target RNA or extended target RNA (target-adapter conjugate) is followed by degradation of linear nucleic acids (e.g., by an exonuclease or mixture of exonucleases).

In certain embodiments, the adapter oligonucleotide comprises the following features: a) size ranging from 10 to 100 nucleotides, including from 20 to 30 nucleotides in length; b) consist of RNA, DNA, or a mix of DNA and RNA residues or their chemical analogs; c) one or more additional sequences, where in certain embodiments the additional sequences are selected from: promoter sites, e.g., for an RNA polymerase; a sequence which is not substantially complementary or corresponds to any sequence that can be present in the sample; a Zip-code sequence; a homopolynucleotide linker; and a sequence encoding one or two linkers used for cloning and sequencing (including next-generation sequencing). The adapter oligonucleotide can be attached at either the 5' or 3' end of the RNA target.

Figure 14C:
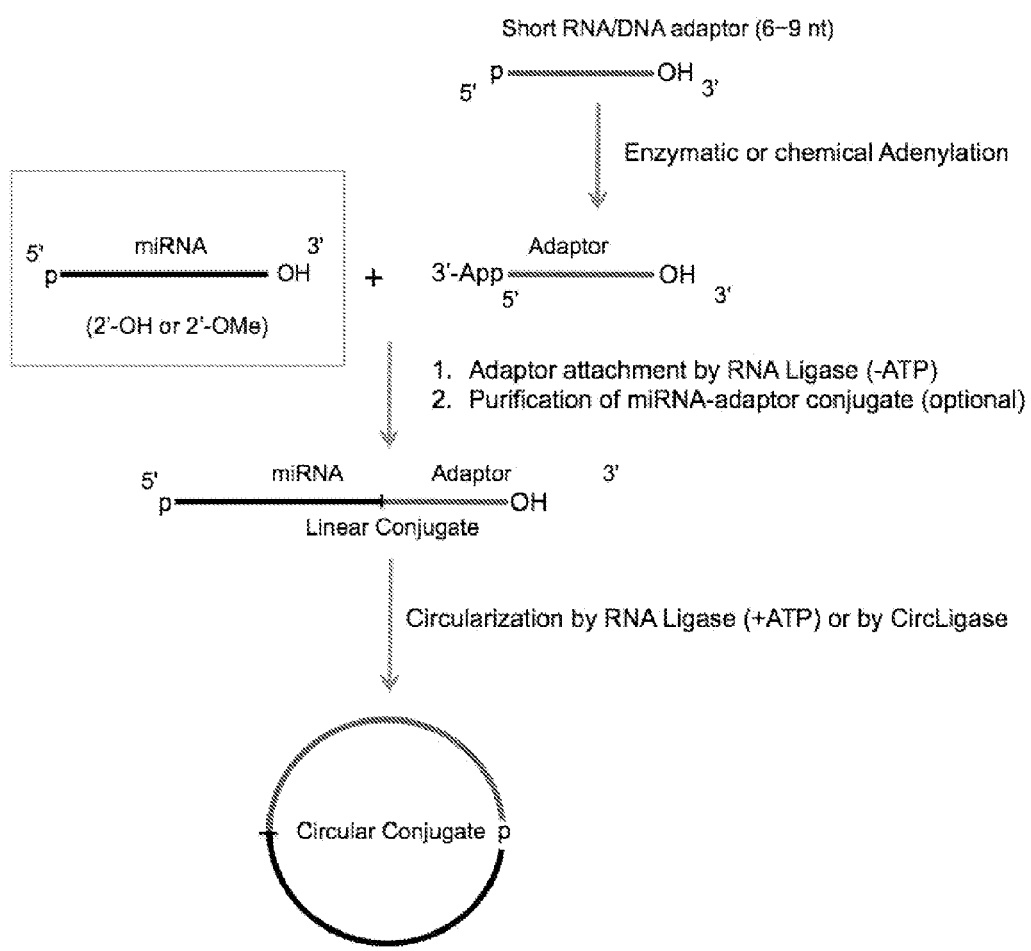

Some current assays for detection and discovery of small RNAs also use the extension of short target sequences by either polyadenylation (Shi & Chiang 2005), or the ligation of adapter/linker oligonucleotides (Lu et al. 2005b), but neither of these assays incorporate a circularization step, which is an essential component of the present invention. The common approach to adapter ligation is using 5'-adenylated adapter oligonucleotides (see structure of the adenylated 5'-end in FIG. 28D) and T4RNA ligase in the absence of ATP (Aravin & Tuschl 2005). Under these conditions, naturally occurring small RNAs that have both 5'-p and 3'-OH (e.g. miRNA) do not undergo self-circularization, which prevents the ligation of the adapter if reaction were carried out in the presence of ATP. Normally, a 5'-adenylated adapter oligonucleotide has its 3' end blocked by a chemical modification that permanently prevents circularization of both the adapter and the target-adapter conjugate. In contrast, our approach requires only a temporary blocking of the adapter 3' end to allow the circularization of the target-adapter conjugate. Accordingly, in some embodiments, an adenylated adapter oligonucleotide carrying 2'-OH and 3'-p at its 3' ends (FIG. 14A) is employed. The 3'-phosphate can be removed by polynucleotide kinase (or phosphatase) to yield 3'-OH (Cameron & Uhlenbeck 1977) while 5'-p, which is necessary for next circularization step, is preserved (FIG. 14A). In another embodiment, a 2'-OMe group at the 3' end of adapter (FIG. 14B) or miRNA (FIG. 16) 3' ends can serve as blocking group even if 3'-OH is unblocked. In yet another embodiments, short (6-9 nt) adapter oligonucleotide (DNA or RNA) have a standard, unmodified 2'-OH/3'-OH groups at its 3' end. The short length of the adapter prevents it from circularization by T4 RNA ligase during the conjugation reaction, but allows the purified conjugate circularization by T4 RNA ligase or CircLigase (FIG. 14C).

Options for circularization of the synthesized target-adapter conjugate carrying 5'-p include the following: 1) using T4 RNA ligase 1 if the conjugate size is <40 nt and the conjugate 3' end has 2'-OH and 3'-OH (FIG. 14A); 2) using CircLigase if the conjugate 3' end has 3'-OH and either 2'-OH or 2'-OMe (FIG. 14B); and 3) splint-assisted ligation (FIG. 15). The splint-less circularization requires no prior knowledge of target RNA sequences and can be applied both for discovery of new and detection of known RNA targets. In contrast, the splint-dependent circularization requires use of an oligonucleotide that contains sequences complementary to both the 5' end sequence of a known target RNA and the 3'-end sequence of the adapter.

As demonstrated in the Examples section below, an adenylated adapter can be efficiently ligated to both 2'-OH or 2'-OMe miRNAs by T4 RNA ligase in the absence of ATP (see Example 15 and FIG. 42). In addition to the use of 2'-OMe adapters discussed above, the 2'-OMe RNA targets also can be used for preparation of the target-adapter conjugates. In certain of these embodiments, a 2'-OMe RNA target is adenylated by T4 RNA ligase in the presence of ATP without self-circularization (and multimerization) despite of presence of free 3'-OH (see FIG. 28A and FIG. 42). The adenylated 2'-OMe RNA is then ligated to the adapter carrying 5'-p and 3'-OH in the absence of ATP (see FIG. 16). This approach is an alternative to methods described previously in which the ligation of a standard adenylated linker to the 3' end of 2'-OMe RNA by T4 RNA ligase, wherein the ligation occurred with reduce efficiency in comparison to 2'-OH RNA (Ebhardt et al. 2005; Vagin et al. 2006; Yang et al. 2006).

In some embodiments, the adapter (or linker) is adenylated by incubation of a corresponding non-adenylated oligonucleotide with RNA ligase I in the presence of ATP, where the oligonucleotide has a 5'-p and includes 3' end groups selected from the following combinations: 2'-OH with 3'-p; or 2'-OMe with 3'-OH as shown in FIG. 14A. In addition to using such adapters in accordance with the present invention, they also can be used for conventional two-adapters-ligation scheme for cloning and sequencing of small RNA targets (FIG. 17) including "next-generation sequencing" methods e.g., Solexa, 454 or SOLiD techniques (Meyers et al. 2006; Lu et al. 2007).

In some embodiments of the invention, the circularized target-adapter conjugate is used as a template for rolling-circle reverse transcription (RT-RCA) to yield multimer cDNA. This is done in two steps: a) binding of circular target RNA with an oligonucleotide RT primer; and b) enzymatic extension of the RT primer by reverse transcriptase. In certain embodiments of the invention, the splint oligonucleotide, which assists in the circularization of the target-adapter conjugate, serves as the RT primer for reverse transcription (FIG. 15). In certain other embodiments, an universal (target-independent) RT primer, which is complementary to a sequence in the adapter, is used (FIG. 18). Because the RT primer is adapter-specific (rather than target specific), multiple circular target RNAs are reverse transcribed simultaneously in multiplex format. However, alignments of RT primers for the reverse transcription of the miRNA-adapter conjugates may vary if necessary (FIG. 18).

In certain embodiments, the primer extension is performed using reverse transcriptase mutants lacking RNAse H activity (e.g. SuperScript II) that can use RNA and RNA-DNA chimeras as templates. The multimer cDNA product produced comprises multiple repeats of tandem target and adapter sequences. In some embodiments of the invention, the adapter comprises one strand of a double-stranded promoter sequence for an RNA polymerase (e.g., a bacteriophage RNA polymerase). In these embodiments, the circularized target-adapter conjugate is used as a template for the synthesis of multimer cRNA (FIG. 19A) using the following two steps: a) binding of an oligodeoxynucleotide comprising the second strand of the RNA polymerase promoter; and b) transcription using the corresponding RNA polymerase that can use either DNA or RNA as templates, such as bacteriophage T3 or T7 RNA RNAP. In certain embodiments, the adapter comprises the sequence (DNA or RNA) of an optimized single-stranded promoter or transcription initiation sequence for a corresponding RNA polymerase (e.g. bacterial RNAP or viral RdRp). Alternatively, viral RNA polymerase mutants such as HCV NS5BΔ21 (Ranjith-Kumar & Kao 2006) could be adopted for promoter-less transcription (FIG. 19B). These circularized target-adapter conjugates find use as templates for synthesis of multimer cRNA rather than cDNA.

In certain embodiments of the invention, multimer cDNAs obtained by RT-RCA of circular target-adapter conjugates are used as templates for transcription by a bacteriophage RNA polymerase (FIG. 20). In these embodiments, the ccRNA may be synthesized in two or three steps: a) binding of an oligodeoxynucleotide comprising one strand of double stranded promoter for the RNA polymerase with the multimer cDNA encoding a second complementary strand of the promoter; b) extension of the oligonucleotide using it as a primer for DNA polymerase (optional step); and c) synthesis of multiple copies of ccRNA, which is complementary to the cDNA, by a bacteriophage RNA polymerase (e.g. T7, T3 or SP6 RNAP). In general, double-stranded DNA templates provide higher yields of transcription products (Gallo et al. 2005). In some embodiments of the invention, multimers of cRNA or ccRNA (e.g., as produced above) serve as a template for reverse transcription to synthesize a single copy of ccDNA by: a) annealing an oligonucleotide RT primer to a ccRNA (or cRNA) that is substantially complementary to a region in the adapter sequence; b) extending the RT primer using a RT enzyme to produce a ccDNA copy of the ccRNA (or cRNA); and c) degrading the ccRNA (or cRNA) strand, e.g., by RNAse H or alkali treatment (optional step).

In some embodiments of the invention, the RT primers described above are not immobilized so that the resultant synthesized cDNAs stay in solution as well as the multimer cRNAs obtained by transcription methods. In certain embodiments of the invention, the multimer nucleic acids synthesized in solution are subjected for affinity capture by hybridization with immobilized anchor oligonucleotide, which is substantially complementary (or corresponds) to the target sequence (FIG. 21). Optionally, the anchor oligonucleotide can be enzymatically extended to provide synthesis of yet another complementary multimer DNA strand, which will be covalently attached to the solid support (FIG. 22A). In other embodiments of the invention, the RT primers described above are immobilized on a solid support and their enzymatic extensions provide direct covalent attachment of synthesized multimer cDNAs to a solid support (FIG. 23). Any convenient solid supports find use in these embodiments, as described above.

In some embodiments of the invention, the capture and attachment of multimer cDNAs is used for purification of the cDNAs and/or their detection. In contrast to the purification task, the detection task includes an arraying (or attachment) of target-specific oligonucleotides to target-designated beads, spots, or compartments on a solid surface. In certain embodiments of the invention, the target-specific oligonucleotides comprise stringency elements (chemical modifications or competitive secondary structures) to provide adequate sequence-specificity of binding to homologous target sequences.

In some embodiments of the invention, the synthesized multimer nucleic acids (MNA) are labeled and subjected for detection without further nucleic acid amplification. In certain embodiments of the invention, the MNA bound to a surface either covalently or non-covalently is subjected to sandwich hybridization with signal oligonucleotide probes, which are complementary (or correspond) to a region in the adapter sequence (FIG. 21B and FIG. 23). The signal oligonucleotide probes may be labeled prior to or after the hybridization step. In certain embodiments, the signal probes, which are complementary to target sequences, also comprise stringency elements. In some embodiments of the invention, the unlabeled signal oligonucleotide probe contain additional universal sequences that are complementary to a secondary, labeled nucleic acid probe, such as branched DNA (bDNA) or DNA dendrimer. In certain embodiments, signal oligonucleotide probes are "muted" probes that induce a signal upon degradation by extension of the anchor oligonucleotide using a DNA polymerase with 5'-exonuclease activity (FIG. 22B). The labeling of MNA and probes can be done using any convenient method, as described above.

In some embodiments of the invention, the synthesized multimer nucleic acids (MNA) comprising repeats of both target and adapter sequences are subjected to detection by real-time qPCR without the needs for TaqMan probes. For this approach, the MNA synthesis is a way of making continuing repeats of target sequences rather than target sequence amplification. The repetitive target-adapter tandem sequences present several advantages as described below.

In some embodiments of the invention, the RT and/or PCR primers are extended primers that comprise target-specific sequences at their 3' ends, which are substantially complementary to or correspond to the target sequences, and adapter-specific sequences at their 5' ends, which are substantially complementary or correspond to all or part of the adapter sequences (FIG. 24). The appropriately selected adapter sequences allow using PCR primers of normal length and allow balance/adjustment of their $T_m$ by extending the target-specific primers into adapter sequences flanking the target in cDNA. More GC-rich target sequences would require less primer extension into the adapter sequence whereas AU-rich target sequences would require longer extensions. A single adapter sequence can be designed to accommodate different extended primers for simultaneous assaying of different target RNAs in the sample.

In some embodiments of the invention, qPCR of multimer cDNA having repeats of target and adapter sequences is performed using target-specific combo primers and universal primers (FIG. 25). Combo primers comprise target-specific sequences at their 3' ends and additional sequences at their 5' ends. The additional sequence is not substantially complementary to nor corresponds to any sequence present in the sample (as described above). The same universal primer, which is not target-specific and complementary to a region in the adapter sequence, can be used as both RT and PCR primer for the assaying of different target RNAs. The first few rounds of PCR amplification are performed with a single combo primer, which is target-specific, and a universal primer, which is specific to the adapter sequence, while the universal primer and another PCR primer, which is complementary to the additional sequence in combo PCR primer, may be used for subsequent real-time qPCR. In certain embodiments, both the adapter and additional sequences are Zip-code sequences.

Figure 26A:
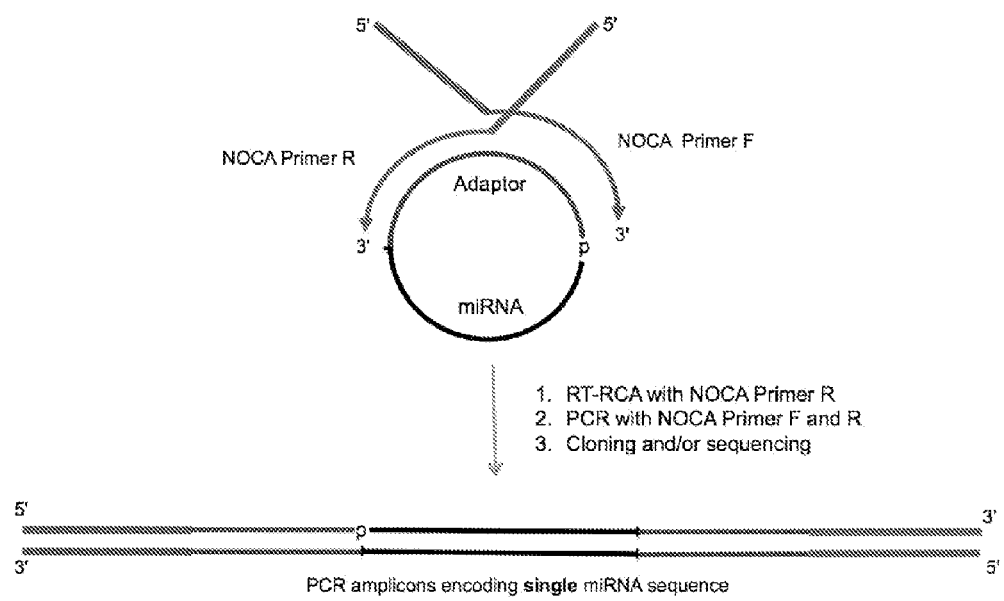

Some aspects of the invention include methods drawn to the discovery of unknown RNAs present in a sample (rather than detection of known RNA targets). These aspects can include the general steps of: a) ligating an adapter (or linker) oligonucleotide to all RNA molecules present in a sample to produce an extended polynucleotide library; b) circularization of each of the extended polynucleotide in the library by ligation of its 5'- and 3'-ends; c) reverse transcription of the circularized extended polynucleotides using a first oligonucleotide primer, whose sequence is complementary to a 5'-end sequence of the adapter, yielding multimer DNA strand (cDNA) comprising multiple repeats of sequences that are complementary to the target RNA and the adapter; d) PCR amplification of the cDNA sequences using the first primer and a second oligonucleotide primer, where the second primer has a sequence corresponding to the 3'-end sequence of the adapter, yielding double-stranded DNA fragments encoding different RNA sequences flanked by the adapter end sequences (sense and antisense); e) sequencing the double-stranded DNA fragments. For this approach, the RT primer may also serve as a PCR primer. Depending on the size of the adapter, at least four types of RT-PCR primers can be used:

(1) Non-overlapping combo primers that are partially complementary to (or correspond to) the adapter sequence only (NOCA primers). NOCO primers comprise adapter-specific sequences and additional upstream (5'-end) sequences, which are unrelated to any sequence present in the sample to be analyzed. They can be Zip-code/Taq sequences (universal or designated to specific target sequences), or adapter/linker sequences used for cloning and sequencing (including next-generation high throughput sequencing). These primers allow the production of monomer PCR amplicons that can be directly used with next-generation-sequencing if the adapter sequence encodes method-specific primers (FIG. 26A).

Figure 26B:
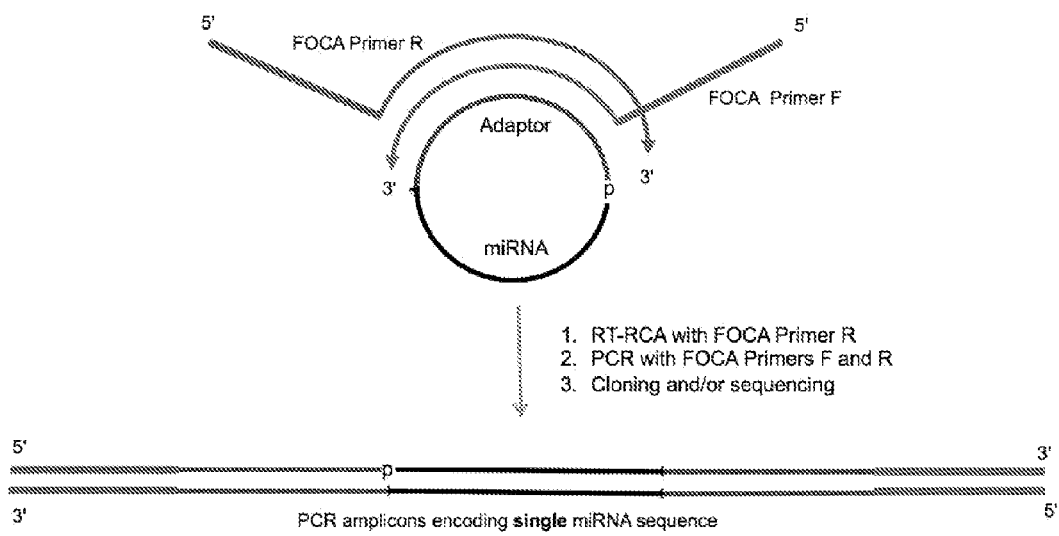

(2) Overlapping combo primers that are partially complementary (or correspond to) the adapter sequence only (FOCA primers). These combo primers are similar to NOCA primers except that they substantially overlap in the middle. FOCA primers can form stronger duplexes with the complementary target sequences than with each other. These primers allow the use of a shorter adapter but still function like NOCA primers (FIG. 26B).

Figure 26C:
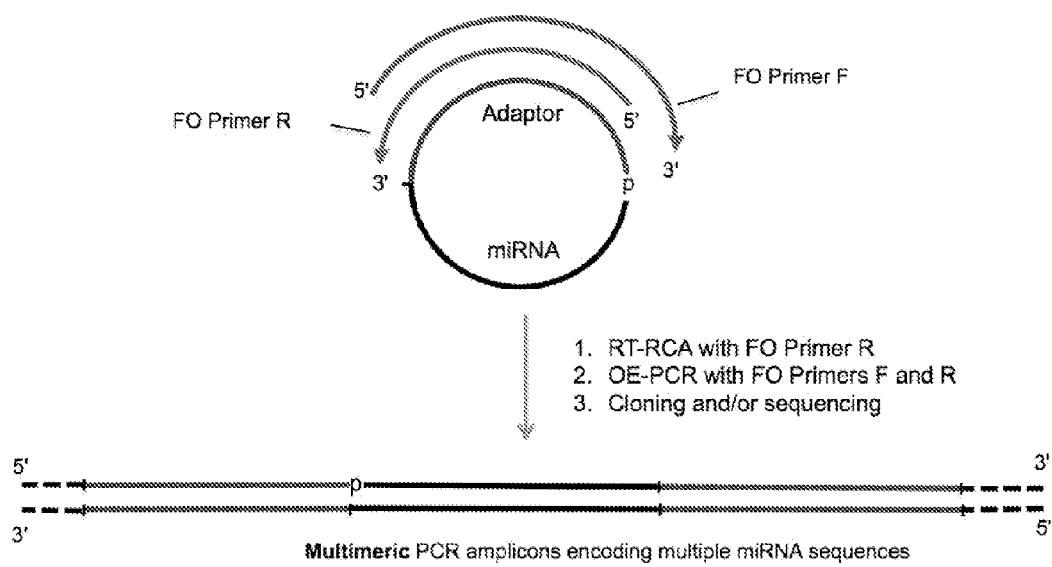

(3) Universal 5'-overlapping primers that are complementary to (or correspond to) adapter sequence only (FO primers; FIG. 26C). These primers allow the production of multimeric PCR amplicons encoding multiple repeats of various miRNA sequences. The adapter sequences in this case are selected to encode appropriate cloning/sequencing linkers and/or restriction sites.

Figure 26D:
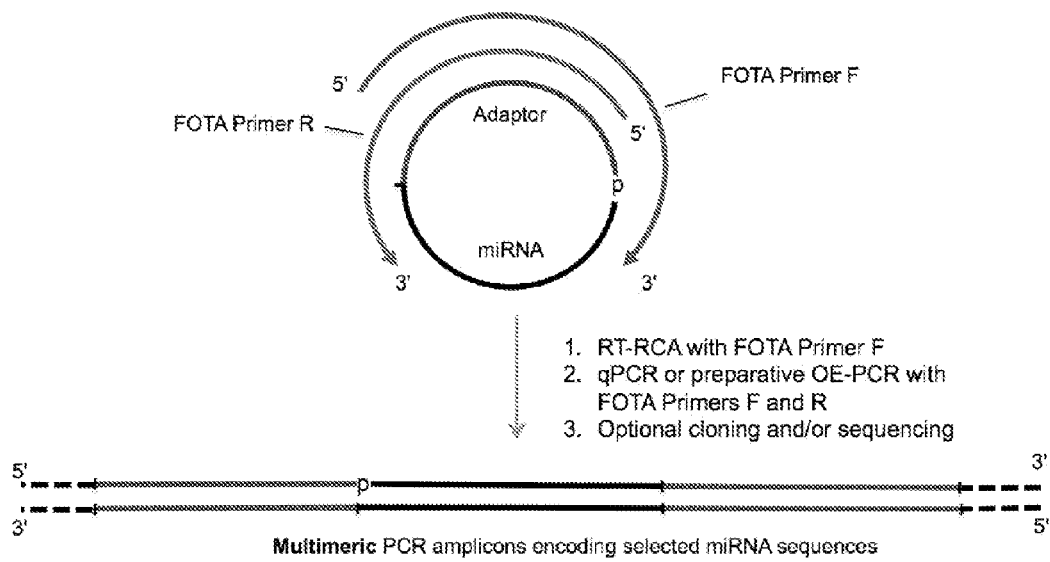

(4) miRNA-specific 5'-overlapping primers that are partially complementary to (or correspond to) both adapter and target miRNA sequences (FOTA primers; FIG. 26D). The target-specific sequences allow the selective amplification of miRNA sequences of interest (e.g. for expression profiling by either HTS sequencing or RT-qPCR). These primers function similar to FO primers except that they generate multimeric PCR amplicons encoding repeats of the selected miRNA sequences.

The non-overlapping RT-PCR primers allow the production of monomer PCR amplicons that can be directly used with the next-generation-sequencing if the adapter sequence encodes method-specific primers. The use of 5'-overlapping primers described here is similar to that described in FIG. 6 above, but in this case, the primers are specific to the adapter rather than to target sequences. The 5'-overlapping primers provide synthesis and amplification of concatamer PCR amplicons by a process known as OE-PCR (see above). The concatamers, the length of which can be controlled by a number of PCR cycles, can be directly used for conventional cloning and sequencing. In comparison to the conventional method comprising ligation of two adapters/linkers to unknown RNA (see FIG. 17), the present invention requires just a single oligonucleotide adapter and fewer steps to amplify, clone and sequence any RNA. Because of the high processivity of so-called next-generation sequencing methods, these methods could be used not only for discovery but also for expression profiling and detection of small target RNAs in a sample. Therefore, schemes shown in FIG. 26 are also applicable for all these tasks. Moreover, in some embodiments of this invention, conventional PCR shown in FIG. 26 is substituted by real-time qPCR, wherein the same universal PCR primers are used for amplification of all target sequences while target-specific probes, either the TaqMan probes or the "muted" probes, are used for detection of specific targets.

Some aspects of this invention are reminiscent of inverse PCR (Hartl & Ochman 1996) and other related methods (Dahl et al. 2005; Friedrich et al. 2005; Polidoros et al. 2006; Potter & Liang 2006) but differ from them in significant aspects. All these methods either directly use circularized DNA or require the conversion of mRNA into DNA before the DNA circularization to PCR amplify and clone sequences flanking a known sequence. Some other aspects of this invention are reminiscent of circularization RT-PCR (cRT-PCR) (Couttet et al. 1997; Kuhn & Binder 2002; Basyuk et al. 2003; Szymkowiak et al. 2003) and reverse-ligation-mediated PCR (RLM-PCR) (Grange 2008), but also differ from them in significant aspects. In RLM-PCR, the ligation event involves either an RNA linker added to the 5' end of cleaved RNA target without circularization of corresponding target-linker conjugate, or RNA circularization without attachment of the linker. The RLM-PCR methods were developed for a mapping of the cleavage points in RNA or simultaneous analysis of sequences at 5' and 3' ends of viral RNAs and genomic mRNAs. Two research groups (Basyuk et al. 2003; Lacombe et al. 2008) describe use of the cRT-PCR for sequencing of ends of certain miRNA precursors. None of these methods were adopted and applied for detection of known RNAs or discovery of unknown RNAs. Also, there are many RCA-based methods for detection of target RNA, but most of them use target-specific, circularizable DNA probes or circularized DNA targets (Lizardi 1998; Nilsson et al. 2006; Zhang et al. 2006). For example, Potter & Liang (2006) describe detection of a target RNA sequence by reverse transcription of mRNAs followed by splint-assisted circularization of corresponding cDNAs which serving as templates for RCA by a DNA polymerase.

Aspects of the subject invention also include kits that find use in performing the methods of the invention. For example, kits may include enzymes or chemical reagents for performing one or more of the steps in the RNA detection methods disclosed herein, including enzymes and/or chemicals for the circularization, synthesis, labeling, purification, amplification, nucleic acid degradation, and/or immobilization steps, etc. Kits may also include any nucleic acid reagents that find use in practicing the disclosed methods, including synthesis primers, anchor oligonucleotides, control RNA samples (either linear or circularized), adapters, promoter-containing oligonucleotides, probes for use in hybridization assays (e.g., for detecting MNA by Northern/Southern blot analyses), PCR primer pairs, etc. Kits according to the present invention may also include anchor oligonucleotides attached to a solid support, e.g., on a bead or in an array format (e.g., a microarray as is employed in the art). Kits may further include detectable labels, e.g., fluorescent labels, radioactive isotope labels, chromogenic labels, or any other convenient label known in the art that find use in detecting MNAs as described herein. Kits may further include any buffers or other reagents employed in any of the steps for RNA detection as described herein as well as instructions for performing RNA detection assays.

EXAMPLES

Example 1

Circularization of 2'-OH miRNAs by T4 RNA Ligase and CircLigase

Figure 27A:
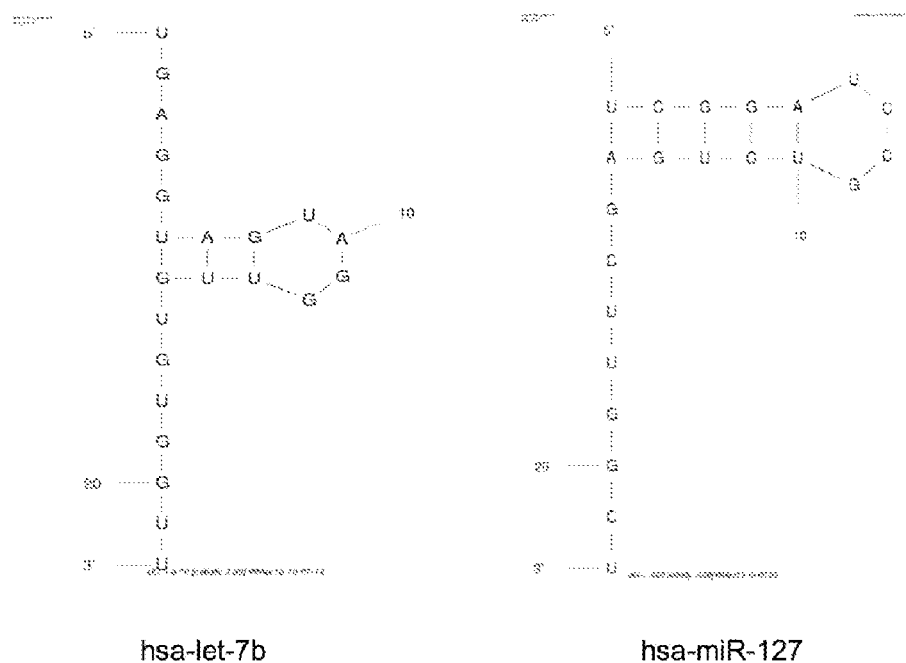
Figure 27B:
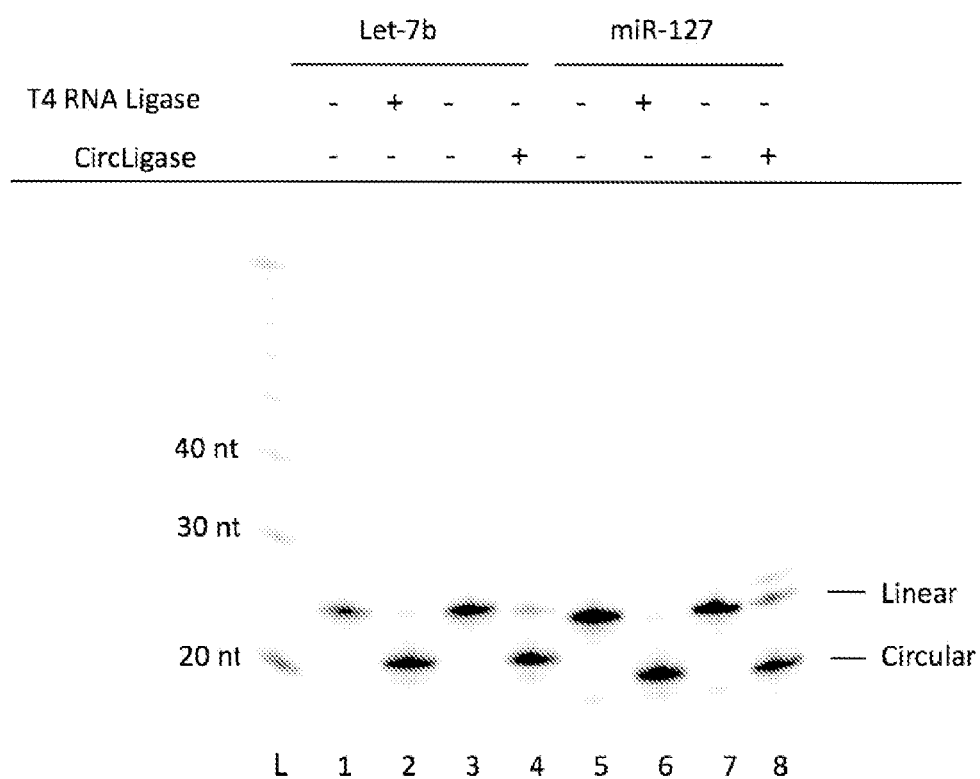

The structure of let-7b and miR-127 are shown in FIG. 27A. The 5' ends of let-7b and miR-127 RNAs were $^{32}$P-phosphorylated by T4 Polynucleotide Kinase (NEB) with [γ$^{32}$P]ATP (Perkin Elmer) according standard protocols. The reaction products were passed through a G-25 spin column (GE Healthcare) to remove the unincorporated [γ$^{32}$P]ATP. 5'-$^{32}$P-labeled linear miRNAs (80 nM) were incubated with or without 0.67 U/μl T4 RNA Ligase 1 (T4RnL1, NEB) for 1 hour at 37° C. in standard ligation buffer (10 mM MgCl$_2$, 10 mM DTT, 1 mM ATP, 50 mM Tris-HCl, pH 7.8); or with or without 5 U/μl CircLigase (Epicentre Biotechnologies) for 1 hour at 60° C. in the supplied buffer (0.05 mM ATP, 5 mM MgCl$_2$, 2.5 mM MnCl$_2$, 1 mM DTT, 10 mM KCl, 50 mM MOPS, pH 7.5). CircLigase is a thermostable enzyme which, according to the manufacturer, can circularize single-stranded DNAs of 30 nt or longer. (The ability of this enzyme to circularize 2'-OH miRNAs carrying a 5'-phosphate and only 22 nt in length was previously unknown.) Products of the ligation reactions were analyzed on a denaturing 15% polyacrylamide gel and the results are shown in FIG. 27B. Lanes 1-4 correspond to let-7b and lanes 5-8 correspond to miR-127 miRNAs. 5' labeled miRNAs were incubated with (lanes 2, 4, 6 and 8) or without (lanes 1, 3, 5 and 7) ligases in the presence of 1 mM ATP for 1 hour. Samples in lanes 2 and 6 were incubated with 1 U/μl T4 RNA ligase 1 at 37° C., and samples in lanes 4 and 8 with 5 U/μl CircLigase at 60° C., each in the appropriate buffer. Lanes marked as L correspond to 5'-$^{32}$P-labeled DNA ladders. The circular miRNA forms migrated slightly faster in the denaturing gel than the linear form. The products were identified as follows: Lanes 1, 3, 5 and 7, unchanged linear form of 2'-OH miRNA; Lanes 2, 4, 6 and 8, circular form of 2'-OH miRNA (bottom band). This example demonstrates that both T4 RNA Ligase 1 and CircLigase can be used for efficient circularization of ordinary miRNAs having a 5'-p and 2'-OH/3'-OH groups at their 3' ends.

Example 2

Adenylation and Circularization of miRNAs Containing Either 2'-OH or 2'-OMe at Their 3'-ends (A) Using T4 RNA Ligase 1: Two synthetic let-7b miRNAs (Table 1) that share the same sequence except that one contains a 2'-OH and the other a 2'-OMe at their 3' ends (see FIG. 28D, right panel) were purchased from IDT (Coralville, Iowa). 5' ends of these RNAs were $^{32}$P-phosphorylated by T4 Polynucleotide Kinase (NEB) as described in Example 1. 5'-$^{32}$P-labeled linear miRNAs (80 nM) were incubated with or without 0.67 U/μl T4 RNA Ligase 1 (NEB) in the presence and absence of 1 mM ATP for 1 hour at 37° C. as described in Example 1. The reaction products were analyzed on a denaturing 15% polyacrylamide gel (FIG. 28A). Lanes 1-3 correspond to the 2'-OH miRNA and lanes 3-6 correspond to the 2'-OMe miRNA. Lanes 1 and 4 have ATP added but no RNA ligase whereas lanes 3 and 6 have RNA ligase added but no ATP. Lanes 2 and 5 had both RNA ligase and ATP. The products were identified as follows: Lane 1: unchanged linear form of 2'-OH miRNA. Lane 2: circular miRNA (bottom band) and adenylated linear 2'-OH miRNA (top band). The circular form of miRNA moves faster in the denaturing gel than its linear form while the adenylated product moves more slowly. The adenylated form of 2'-OH miRNA is an intermediate in the ligation reaction (see FIG. 28D, left panel) that undergoes conversion to the circular form by the RNA ligase. Lane 3: unchanged linear form of 2'-OH miRNA. Lane 4: unchanged linear form of 2'-OMe miRNA. Lane 5: adenylated linear 2'-OMe miRNA. In contrast to lane 2, no circular miRNA was detected in lane 5, indicating that the 2'-OMe group of this miRNA prevents circularization by T4 RNA ligase 1. Lane 6: unchanged linear form of 2'-OMe miRNA. This example demonstrates that: (1) T4 RNA ligase 1 can be used for circularization of 2'-OH miRNAs but not 2'-OMe forms; and (2) 2'-OMe RNAs can be efficiently adenylated at their 5' ends but the 2'-OMe group prevents subsequent circularization of the adenylated RNA despite the presence of a free 3'-OH.

(B) Circularization of synthetic let-7b miRNAs containing either 2'-OH or a 2'-OMe at their 3'-ends by CircLigase: Two synthetic let-7b miRNAs, one containing a 2'-OH and the other a 2'-OMe at their 3'-ends, were $^{32}$P-phosphorylated at their 5' ends and then incubated with or without 5 U/μl CircLigase (Epicentre Biotechnologies) for 1 hour at 60° C. as described in Example 1. Incubation with CircLigase was followed by exonuclease treatment with Exo I (Epicentre) to confirm circularization of the miRNA. Exo I digests single-stranded nucleic acids (both DNA and RNA) in a 3'→5' direction and requires a free 3'-end. A circular RNA with no 3' end thus cannot be degraded by Exo I. The effect of the 2'-OMe group on Exo I activity was previously unknown. The miRNA samples were incubated with or without CircLigase and then incubated with Exo I (2 U/μl) for 30 min at 37° C. The reaction products were analyzed on a denaturing 20% polyacrylamide gel (FIG. 28B). Lanes 1-4 correspond to the 2'-OH miRNA and lanes 5-8 correspond to the 2'-OMe miRNA. Lanes 1-2 and 5-6 have CircLigase added, whereas lanes 3-4 and 7-8 do not. Exo I was added only in lanes 2, 4, 6 and 8. The products were identified as follows: Lane 1: circular form of miRNA without exonuclease treatment. This result demonstrates that CircLigase is very efficient in circularizing linear 2'-OH miRNA. The circular form moves slightly faster in the denaturing gel than the linear form. Lane 2: circular form of miRNA with exonuclease treatment. This result demonstrates that circular miRNA is indeed resistant to Exo I. Lane 3: untreated linear form of 2'-OH miRNA as a control. Lane 4: fully degraded linear form of 2'-OH miRNA after exonuclease treatment. Lane 5: circular form of miRNA without exonuclease treatment. This result demonstrates that, unlike T4 RNA Ligase 1, CircLigase can efficiently circularize linear 2'-OMe miRNA. Lane 6: circular form of miRNA with exonuclease treatment, demonstrating that linear 2'-OMe miRNA was indeed converted into the circular form, which is resistant to Exo I. Lane 7: untreated linear form of 2'-OMe miRNA as a control. Lane 8: partially degraded linear form of 2'-OMe miRNA after exonuclease treatment, showing that 2'-OMe does not prevent the 3'→5' digestion of the RNA, although it does slow the reaction. This example demonstrates that: (1) CircLigase ligase can be used for circularization of both 2'-OH and 2'-OMe miRNAs; and (2) Exo I treatment can be used to degrade both 2'-OH and 2'-OMe RNAs in their linear forms.

(C) Circularization of 2'-OH and 2'-OMe miRNAs containing various 3'-terminal nucleotides by T4 RNA Ligase 1: Synthetic miRNAs (let-7b, let-7g, miR-16 and miR-23a: Table 1) were prepared with 5'-OH and either 2'-OH/3'-OH (lanes 13-15) or 2'-OMe/3'OH (lanes 1-12) groups at their 3' ends. These miRNAs represent two forms of let 7b miRNA, 2'-OH (lanes 13-15) and 2'-OMe (lanes 1-3), and four 2'-OMe miRNAs having different nucleotides at their 3' ends (lanes 1-12). The miRNAs were $^{32}$P-phosphorylated at their 5' ends by T4 Polynucleotide Kinase (NEB) and incubated with 0.67 U/μl T4 RNA Ligase I (NEB) at 37° C. as described in Example 1. Samples were taken after 1 min, 1 h and 3 h. The reaction products were analyzed on a denaturing 20% polyacrylamide gel (FIG. 28C). The products were unchanged linear, circular and adenylated forms of the miRNAs. The circular form of the miRNAs of 21-22 nt moves faster in the denaturing gel than its linear form while the adenylated product migrates more slowly. The 3' end nucleotide of the miRNA is indicated in parentheses below. The products were identified as follows: Lane 1: unchanged linear form of 2'-OMe let-7b (U) miRNA (dominant lower band) and traces of the adenylated form (upper band). Lanes 2 and 3: adenylated form (upper band) of 2'-OMe let-7b (U) miRNA. Lane 4: unchanged linear form of 2'-OMe let-7g (A) miRNA (dominant lower band) and traces of adenylated form (upper band). Lanes 5 and 6: Dominant adenylated form (upper band) of 2'-OMe let-7g (A) miRNA. Lane 7: unchanged linear form of 2'-OMe miR-16 (G) miRNA (dominant lower band) and traces of adenylated form (upper band). Lane 8: Adenylated (upper) and circular (lower) band of 2'-OMe miR-16 (G) miRNA. Lane 9: Dominant Circular form (lower band) and adenylated form (upper form) of 2'-OMe miR-16 (G) miRNA. Lane 10: unchanged linear form of 2'-OMe miR-23a (C) miRNA (dominant lower band) and traces of adenylated form (upper band). Lanes 11 and 12: adenylated (dominant upper band) and circular (lower) band of 2'-OMe miR-23a (C) miRNA. Lane 13: Circular form of 2'-OH let-7b (U) miRNA (dominant lower band) and traces of unchanged linear and adenylated form (upper bands). Lanes 14 and 15: predominantly circular form of 2'-OH let-7b (U) miRNA. This example demonstrates that the inhibitory effect of the 2'-OMe modification on circularization by T4 RNA Ligase 1 depends on the 3' end nucleotide in the order U~A>>C>G (see lanes 2, 5, 8 and 11). However, use of short ligation reactions (≤60 min) with T4 RNA ligase results in 2'-OMe miRNAs with any 3'-end nucleotide maintaining their linear form while the 2'-OH versions are efficiently circularized. CircLigase provides efficient circularization of both forms of miRNAs.

Example 3

Circular miR-127 miRNA can Serve as a Template for Multimeric cDNA Synthesis by Rolling Circle Reverse Transcription (RT-RCA) Using Primers of Different Lengths (A) A synthetic let-7b miRNA containing a 2'-OH at its 3'-end and a 5'-phosphate was circularized by T4 RNA ligase 1 as described in Example 1. The circularized miRNA was used as template for reverse transcription using as RT primers synthetic DNA oligonucleotides (IDT) of three different lengths:

```
                                              (SEQ ID NO: 25)
5'-ACCACACAACCTAC-3'
(Table 1: 7bRT14, complementary to nt 8-21 of
let-7b);

(SEQ ID NO: 24)
5'-CACACAACCTAC-3'
(Table 1: 7bRT12, complementary to nt 8-19 of
let-7b);

(SEQ ID NO: 23)
5'-CACAACCTAC-3'
(Table 1: 7bRT10, complementary to nt 8-17 of
let-7b).
```

The 5' ends of these primers and an appropriate DNA ladder (Invitrogen) were $^{32}$P-phosphorylated by T4 Polynucleotide Kinase (NEB) with [γ$^{32}$P]ATP (Perkin Elmer) according standard protocols. The reaction products were passed through a G-25 spin column (GE Healthcare) to remove the unincorporated radiolabeled ATP. 5'-$^{32}$P-labeled primers (80 nM) were then mixed with the circular miRNA (80 nM) and incubated in the absence or presence of 4 U/μl reverse transcriptase SuperScript II (SSII; Invitrogen) at 42° C. for 1 hour in the supplied buffer (75 mM KCl, 3 mM MgCl$_2$, 10 mM DTT, 50 mM Tris-HCl, pH 8.3). The reaction products were analyzed on a denaturing 15% polyacrylamide gel (FIG. 29A) along with the 5'-$^{32}$P-labeled DNA ladder. Lanes 1-2 correspond to the 14-nt primer, lanes 3-4 to the 12-nt primer, and lanes 5-6 to the 10-nt primer. Lanes 2, 4 and 6 have SSII added whereas lanes 1, 3 and 5 do not. Lanes marked as L correspond to DNA ladders. The products were identified as follows: Lane 1: non-extended 14-nt primer. Lane 2: extended 14-nt primer. Lane 3: non-extended 12-nt primer. Lane 4: extended 12-nt primer. Lane 5: non-extended 10-nt primer. Lane 6: extended 10-nt primer.

(B) A synthetic miR-127 having a 5'-p and 2'-OH/3'-OH at its 3'-end was circularized by Circ Ligase II as described in Example 1. The circularized miRNA was then used as a template for reverse transcription with miRNA-specific RT primers of different lengths and sequence (FIG. 29B): CAAGCTC<u>AGACGGATC</u>CGA (SEQ ID NO:33) (19 nt) and <u>AGACGGATC</u> SEQ ID NO:32) (10 nt). The common sequence between the two primers is underlined. The RT primers (1 μM) were incubated with (lanes 2-3) or without 100 nM circular miR-127 miRNA (lane 4) in the presence of 4 U/μl SuperScript II reverse transcriptase (SSII; Invitrogen), 1 U/μl RNAseOUT ribonuclease inhibitor, 400 μM dNTPs and [α$^{32}$P]dATP at 42° C. for 2 hours as described above. The RT-RCA extension products were analyzed on a denaturing 12% polyacrylamide gel (FIG. 29B). The products were identified as follows. Lane L: 5'-$^{32}$P-labeled DNA ladder. Lane 1: Linear 5'-$^{32}$P-labeled miR-127. Lanes 2 and 3: Extended 19 and 10 nt primer. Lane 4: No circular miR-127 was present. This example demonstrates that: (1) DNA primers bound to the circularized miRNA can generate multiple extension products corresponding to monomer and multimer miRNA lengths; and (2) efficiency of RT-RCA is not affected by the length of the RT primer as long as it is able to initiate the extension reaction. It was expected that small circular RNAs would restrict number of base pairs that can simultaneously be formed with the RT primer, and only duplexes in which the primer 340 -end is base-paired with the target could initiate reverse transcription. However, we found that even 19-nt RT primers, which are about the size of the miRNA, could provide efficient RT-RCA.

Example 4

RT-PCR Amplification of Circular miRNA by 5'-overlapping Primers

Synthetic let-7b miRNA containing a 2'-OH at its 3'-end and a 5'-phosphate was circularized by T4 RNA ligase 1 as described in Example 1. Both linear (LT) and circular (CT) forms of the miRNA (80 nM) were used as templates for reverse transcription (RT) with 7bRev1RT (Table 1) as described in Example 3. Samples containing no miRNA targets were used as negative controls. PCR was then carried out to amplify the cDNA generated by RT using the primers 7bFwd1 and 7bRev1RT (Table 1). The PCR primers had 15 nt of overlap at their 5' ends, leaving only 3-nt overhangs at their 3' ends. Alignments of these primers with the linear and circular miRNA targets were as shown in FIG. 6C, in which case Primer 7bRev1RT cannot reverse transcribe a linear miRNA target. In the PCR reaction, products of the RT reaction were mixed with 400 nM primers and 0.1 U/µl Hot FirePol DNA Polymerase (Solis BioDyne) in the supplied buffer. The PCR reaction mixtures were subjected to initial denaturation at 94° C. for 15 min (to activate the enzyme), followed by either 20 or 25 cycles of PCR with each cycle 94° C. for 45 sec/58° C. for 45 sec/70° C. for 30 seconds. The PCR products were analyzed on a 3% agarose gel with ethidium bromide staining (FIG. 30). Lane L is a DNA ladder. Lanes 1-3 correspond to 20 cycles and lanes 4-6 to 25 cycles of PCR. Lanes 1 and 4 have the circular form (CT) and lanes 2 and 5 the linear form (LT) of the target miRNA. Lanes 3 and 6 had only primers and no miRNA-specific cDNA. UP are unused PCR primers. The products were identified as follows: Lanes 1 and 4: multimer PCR amplicons. With more PCR cycles, longer multimers were generated, presumably due to the process of overlap-extension PCR (OE-PCR) as illustrated in FIG. 8. Lanes 2, 3 and 6: no products. Lane 5: Small amounts of a 38 bp amplicon, which is longer than two primer lengths (36 nt) combined. This example demonstrates that: (1) 5'-overlapping dimer-primers that have short overhangs at their 3' ends can provide efficient RT-PCR amplification of multimeric but not monomeric templates; (2) RT-PCR of circular miRNA targets generates multimeric products as a result of three processes: RT-RCA leading to multimeric cDNA, (FIG. 2A), 5'-overlapping primer-assisted PCR of this cDNA (FIG. 6B), and OE-PCR (FIG. 8).

Example 5

Testing Dynamic Range and Sensitivity of Detection of Circular miRNA with RT and qPCR Using 5' Overlapping Primers (miR-ID Assay)

Figure 31A:
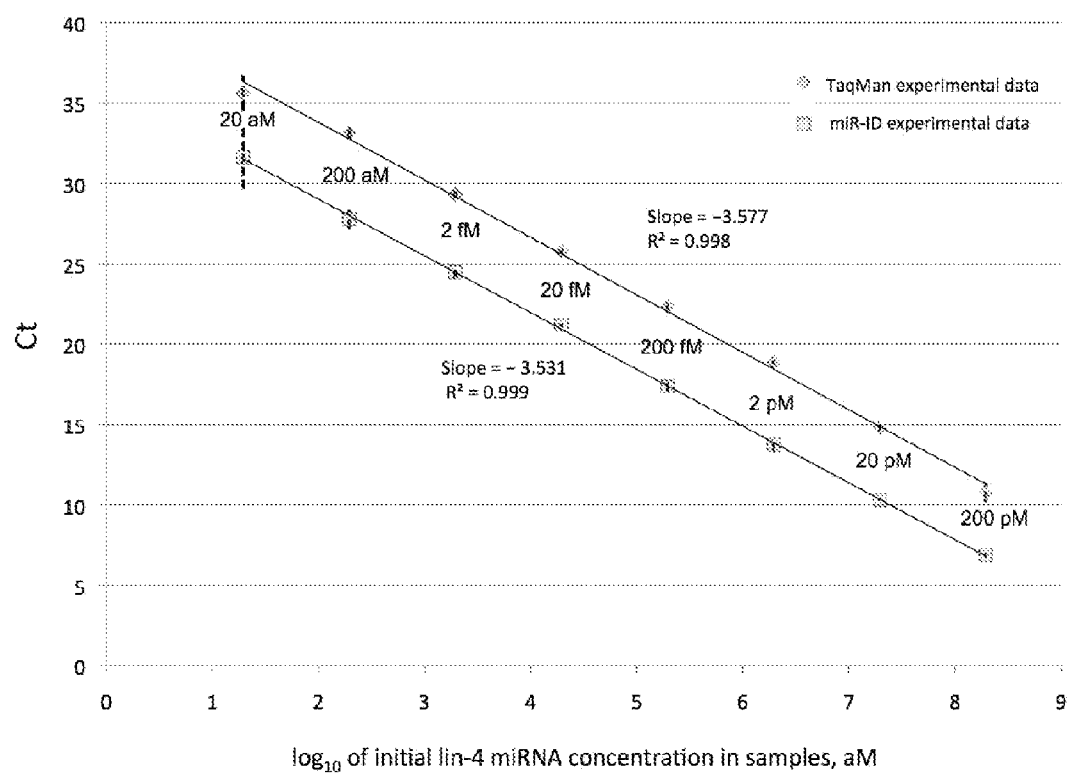

(A) Using T4 RNA Ligase 1 in the circularization step: Various concentrations (0.2 nM, 0.02 nM, 2 pM, 0.2 pM, 0.02 pM, 2 fM, 0.2 fM and 0.02 fM) of synthetic lin-4, which had 5'-p and 2'-OH/3'-OH at the 3' end, were subjected to circularization (in duplicate) by 0.67 U/µl T4 RNA ligase 1 (NEB) as described in Example 1. A 50 µl reverse transcription reaction was set up as described in Example 3 containing the lin4RT primer (Table 1) at a final concentration of 100 nM. In the next step, qPCR was carried out to amplify the cDNA generated by RT using lin-4 specific 5'-overlapping primer pairs of 19-nt each (Table 1), which had 16-nt overlap at their 5' ends and 3-nt overhangs at their 3' ends. A 20 µl reaction was set up containing 150 nM 5'-overlapping PCR primers, 1× Brilliant II SYBR Green QPCR master mix (Stratagene, kit 600828), 375 nM Reference dye (Stratagene, kit 600828). The qPCR reaction cycle included a 2 min incubation at 50° C., 10 min incubation at 95° C., followed by 45 cycles of (95° C. for 45 sec/56° C. for 45 sec/66° C. for 30 sec/67° C. for 30 sec). There was +0.1° C. increment setup at the 66° C. step and a +0.2° C. increment setup at the 67° C. step. Data was collected at the final extension step (67° C. with an incremental increase of +0.2° C.) in each cycle. The qPCR was carried out on a 7500-fast ABI system. All qPCR reactions were done in triplicate. Ct values were exported and analyzed using 2008 Microsoft Excel software to plot the standard curve (FIG. 31A). All obtained $C_t$ values were in the range of linearity with the log of the miRNA input. The negative control produced no amplification (data not shown). Uniform thermal dissociation curves for each tested miRNA concentrations (data not shown) indicated the presence of only a single amplification product and absence of non-specific amplification products.

We directly compared the standard curves obtained by miR-ID with those for TaqMan microRNA assays. The same (as for miR-ID) dilution series of miRNA lin-4 were used in TaqMan microRNA RT-PCR assay (ABI/Life Technologies, part 4366596) performed according standard protocol. Briefly, a 15 µA reaction including 3 µl of the 5×lin-4 RT primer (assay ID:000258) was set up and incubated consecutively at 16° C. for 30 min, 42° C. for 30 min and 85° C. for 5 min. A 20 µl qPCR reaction, which included 1.35 µl of the RT reaction products and 1 µl of 20× mix of universal PCR primer with lin-4-specific PCR primer and TaqMan probe (assay ID: 000258) were run on the ABI 7500-fast system following the recommended cycling conditions: 50° C. for 2 min/95° C. for 10 min/40 cycles of (95° C. for 15 sec/60° C. for 1 min). All qPCR reactions were done in triplicate. Both methods provided the same detection limit (~10 miRNA copies), but miR-ID was found to be significantly more sensitive than the TaqMan assay across the entire dynamic range of 7 orders of magnitude, as shown by the lower $C_t$ values at each concentration (ΔCt=5 between the miR-ID and TaqMan standard curves, corresponding to a 32-fold ($2^5$) stronger signal) (FIG. 31A). The superior sensitivity of miR-ID is due to the additional signal amplification from RCA and overlap extension PCR as well as lower background noise resulting from use of the 5'-overlapping primers.

Figure 31B:
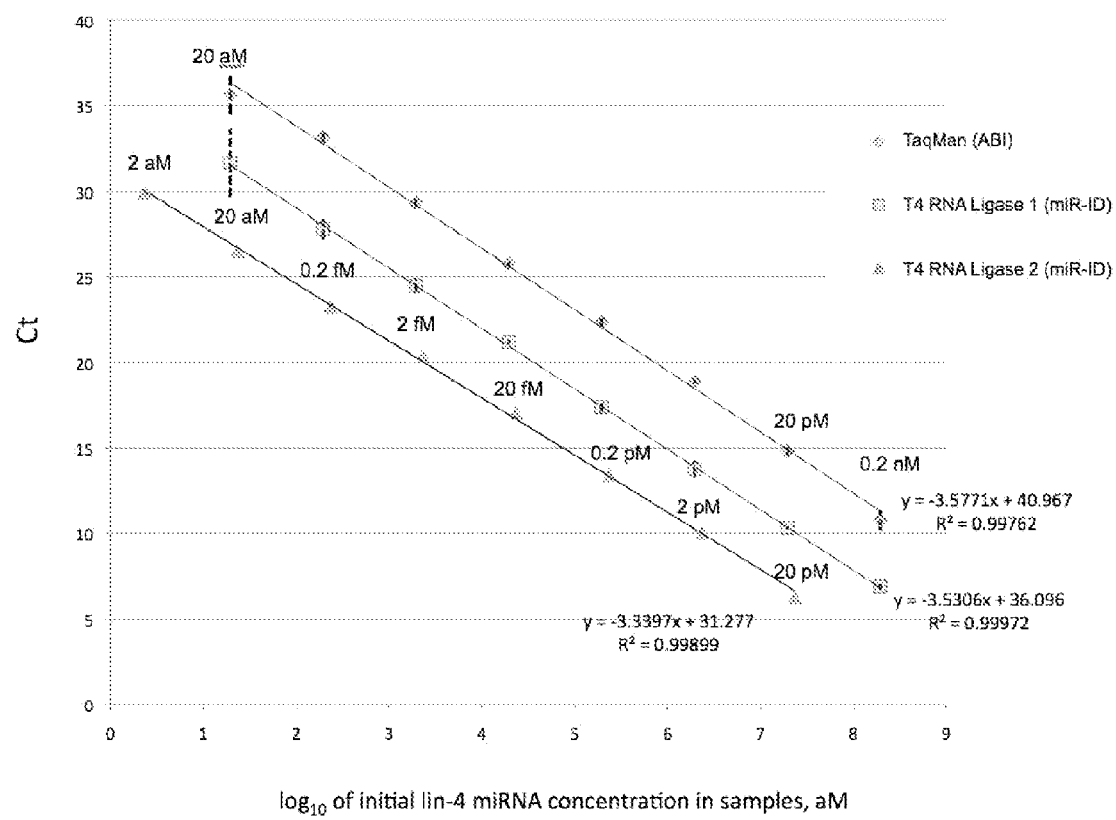

(B) Using T4 RNA Ligase 2 splint RT primer mediated circularization, reverse transcription and qPCR. Various concentrations (0.02 nM, 2 pM, 0.2 pM, 0.02 pM, 2 fM, 0.2 fM, 0.02 fM and 2 aM) of synthetic lin-4, which had 5'-p and 2'-OH/3'-OH at the 3' end, were subjected to simultaneous circularization and reverse transcription using a lin4-splint RT primer (Table 1) which spanned across the 5' and 3' junction of the miRNA. A 50 µl circularization coupled reverse transcription reaction was set up containing the lin4-splint RT primer at a final concentration of 100 nM, incubated with 4 U/µl reverse transcriptase SuperScript II (SSII; Invitrogen) and 0.3 U/µl T4 RNA Ligase 2 (T4RNI2: New England Biolabs) for 2 hours at 40° C. in supplied RT buffer (75 mM KCl, 3 mM $MgCl_2$, 10 mM DTT, 50 mM Tris-HCl, pH 8.3), along with ATP and dNTPS at final concentrations of 200 µM and 400 µM respectively. This was followed by heat-inactivation of SSII at 75° C. for 15 min. In the next step, qPCR was carried out to amplify the cDNA generated using lin-4 specific 5'-overlapping primer pairs of 19-nt each (Table 1), exactly as described above. Ct values were exported and analyzed using 2008 Microsoft Excel software to plot the standard curve (FIG. 31B). All obtained Ct values were in the range of linearity with the log of the miRNA input. The negative control produced no amplification (data not shown). Uniform thermal dissociation curves for each tested miRNA concentrations (data not shown) indicated the presence of only a single amplification product and absence of non-specific amplification products.

We directly compared the standard curves obtained by these alternative variants of miR-ID assay (see FIG. 31B). Our results indicate that the splint-assisted ligation by T4RNA ligase 2 in the first step, and its combination with simultaneous RT-RCA using the splint oligonucleotide as RT primer provide even higher (about 8 times) sensitivity than the first variant of miR-ID using T4RNA ligase 1. Both miR-ID assays provide much higher sensitivity than the TaqMan assay.

Example 6

Detection of Specific Circular miRNA Target by RT-PCR Using Combo Primers, which Comprise Target-specific and Zip-code Sequences, and Zip-code Primers Synthetic let-7b miRNAs and RNA19 (Table 1), both containing a 2'-OH at its 3'-end and a 5'-phosphate, were circularized by T4 RNA ligase 1 as described in Example 1. RNA19 is an unrelated (to let-7b miRNA) 19 nt RNA and was used as a negative control. Both circular RNAs along with a negative control, which has no RNA, were used in reverse transcription (RT) reaction with combo Primer R (let7bComboR: Table 1). The circular RNA templates (80 nM) were mixed with the let7bComboR primer (80 nM) and reverse transcribed by SuperScript II as described in Example 3. In next step, PCR was carried out to amplify the cDNA generated by RT using the same let7bComboR in combination with let7bComboF (Table 1). Both forward (F) and reverse (R) combo primers comprised two different sets of 11 nt target-specific sequences at their 3' ends and 24 nt Zip-code sequences at their 5' ends adapted from Gerry et al. (1999). Target-specific sequence of Primer R is complementary to 1-11 nt whereas target-specific sequence of Primer F corresponds to 12-22 nt in let-7b miRNA. Alignments of these primers with the circular miRNA target and the multimer cDNA product are shown in FIG. 12A and FIG. 12B, respectively.

In the PCR reaction, 0.1× samples of RT reaction products were mixed with 500 nM combo primers and 0.05 U/µl Taq DNA polymerase (Promega) in the supplied buffer. The PCR reaction mixtures were subjected to initial denaturation at 94° C. for 2 min, followed by 5, 7 or 10 cycles of PCR: 94° C. for 30 sec/70° C. for 2 min. The PCR products were then passed through a PCR-purification micro column (Zymo Research) to remove excess of combo primers and eluted in 10 µA volumes. The products of the first PCR were then subjected to a second PCR reaction—now using two Zip-code primers (ZC1 and ZC2: Table 1), which corresponded to the zip-code portion of Combo Primer R and F respectively. In the second PCR reaction, 5 µl samples of the first PCR reaction were mixed with 500 nM Zip-code primers and 0.05 U/µl Taq DNA polymerase (Promega) in the supplied buffer. The PCR reaction mixtures were subjected to initial denaturation at 94° C. for 2 min, followed by 30 cycles: 94° C. for 30 sec/63° C. for 30 sec/72° C. for 30 seconds. The PCR products were analyzed in 3% agarose gel after ethidium bromide staining (FIG. 32). Lane L is DNA ladder (Fermentas). Lanes 1-3 corresponds to 5 cycles, lanes 4-6—to 7 cycles, and lanes 7-9—to 10 cycles of the first PCR. Lanes 1, 4 and 7 have circular let-7b miRNA whereas lanes 2, 5 and 8—unrelated RNA19 control. Lanes 3, 6 and 9 are negative controls that had no RNA. The products were identified as follows: Lanes 1, 4 and 7: single PCR product corresponding to expected 70 bp replicon. Lanes 2-3 and 5-6: no products. Lanes 8 and 9: low amounts of "parasitic" background products that could be detected in the negative control samples only after 10 cycles or the first PCR with combo primers. This example demonstrates that: (1) a combination of RT-PCR using combo primers and second PCR using zip-code primers provided specific detection of target miRNA; (2) 7 cycles of PCR pre-amplification with combo primers is optimal. This step provides 128-times amplification of target sequence before PCR with the Zip-code primers.

Example 7

Demonstration of miR-ID Assay Specificity by Discrimination of Closely Related let-7 miRNA Isoforms Synthetic miRNAs let-7a, let-7b, let-7c, let-7d and let-7e (Table 1) containing 2'-OH at its 3'-end and 5'-phosphate, were individually circularized by T4 RNA ligase 1 as described in Example 1. These homologous miRNAs have 1-2 nucleotide differences between each other (FIG. 33A). The circularized let-7 miRNA isoforms (one-tenth volume of circularization reactions) were used as template for the 50 µl reverse transcription reaction, which were individually performed for each miRNA, using universal 7acdRT primer (for let-7a, c and d) or specific 7eRT and 7bRT primer (for let-7b and 7e) (Table 1) at a final concentration of 100 nM as described in Example 3. In next step, qPCR was carried out to amplify the cDNA generated by RT using isoform-specific 5'-overlapping primer pairs of 18-nt each (Table 1), which had 15-nt overlap at their 5' ends and 3-nt overhangs at their 3' ends. Each isoform-specific RT reaction was subjected to real-time qPCR (in duplicate) in a cross-reactive manner. For example, one-tenth volume of the RT product of let-7a was used as template for qPCR with 5'-overlapping primers specific for let-7a, let-7b, let-7c, let-7d and let-7e in five separate reactions. All qPCR reactions were done in duplicate and as described in Example 5. Ct values were exported and analyzed using 2008 Microsoft Excel software. The maximum signal in each assay was normalized to 100, and the remaining values were calculated relative to the maximum signal. Data was plotted on a linear scale (FIG. 33B). Corresponding values (others than 0.0) for Qiagen's miScript/SYBR Green (*), ABI's TaqMan () (Chen et al. 2005) and LNA/SYBR Green (*) (Raymond et al. 2005) RT-PCR assays of the same miRNAs are shown in parentheses. In contrast to the competing platforms, no significant cross-reactions between different sets of miRNA isoforms and RT-PCR primers were detected for miR-ID. This example demonstrates that: (1) miR-ID can discriminate miRNA species that differ by as little as 1 nt; (2) the discrimination factors between the same let-7 isoforms for miR-ID were substantially better than those reported for three of the most commonly used RT-PCR methods demonstrating superior sequence-specificity of miR-ID assay.

Example 8

Discrimination between Mature miRNA and Pre-miRNA in miR-ID Assays

Sequences and structure of mature let-7b miRNA and its precursor (pre-miRNA) encoding the highlighted mature miRNA sequence are shown in FIG. 34A. pre-let-7b was synthesized by annealing two synthetic RNA oligonucleotides (pre7b1 and pre7b2: Table 1) and ligating them with 0.67 U/µl T4 RNA Ligase 1 for 16 h at 16° C. in the supplied buffer (10 mM $MgCl_2$, 1 mM ATP, 10 mM DTT, 50 mM Tris-HCl, pH 7.8). The ligation products were analyzed on a denaturing 15% polyacrylamide gel and full-length pre-let-7b was gel-purified. 1 nM of mature let-7b and gel-purified pre-let-7b, containing 5'-p and 2'-OH/3'-OH at their 3' ends were circularized individually by T4 RNA Ligase 1 as described in Example 1. In the RT step, one-tenth volume of circularized let-7b and pre-let-7b samples was mixed with 100 nM let-7bRT primer (Table 1) and this primer was extended by SuperScript II reverse transcriptase for 2 h at 42° C. as described in Example 3. In the real-time qPCR step, one-tenth volume of each RT reaction was assayed using 150 nM 5'-overlapping PCR primers: let7bmatF and let7bmatR (Table 1). These primers had a 15 nt overlap at their 5' ends and 3-nt overhangs at their 3' ends. The qPCR reactions were carried out in duplicate and as described in Example 5. A $\Delta Ct\sim 12$ (FIG. 34B) between the mature miRNA and pre-miRNA assayed at the same concentration using the miRNA-specific primers implies at least 4000-times ($2^{12}=4096$) discrimination between these two RNA forms. This example demonstrates that miR-ID can accurately discriminate pre-miRNAs, which may interfere with accurate detection of the mature miRNA.

Example 9

Sensitivity and Detection Limit of an Individual miRNA in miR-ID Assays are not Affected by Presence of Total RNA Various concentrations (0.2 nM, 0.02 nM, 2 pM, 0.2 pM, 0.02 pM, 2 fM and 0.2 fM) of synthetic miR-127 having a 5'-p and 2'-OH/3'-OH at its 3' end were circularized by T4 RNA ligase 1 as described in Example 1 either in absence or presence of 20 ng of total RNA extracted from Jurkat cells. These cells do not express endogenous miR-127 (Yu et al. 2006). In the RT step, one-tenth volume of each circularized miRNA sample was mixed with 100 nM 127RT19 primer (Table 1), and this primer was extended by SuperScript II reverse transcriptase for 2 h at 42° C. as described in Example 3. In the real-time qPCR step, one-tenth volume of each RT reaction was assayed using 150 nM 5'-overlapping PCR primers (127Fwd and 127RT19: Table 1). These primers had 16 nt of overlap at their 5' ends and 3-nt overhangs at their 3' ends. The total dilution of the miR-127 inputs from the initial concentrations to qPCR was 40-fold, and final (post dilution) concentrations in the PCR step are shown. The qPCR reactions were carried out in duplicate and as described in Example 5, except that the annealing temperature was 63° C. Ct values were exported and analyzed using Microsoft Excel software to plot the standard curve (FIG. 35). All obtained Ct values were in the range of linearity with the log of the miRNA input.

The presence of a fixed amount of total RNA (20 ng) extracted from Jurkat cells (human acute T cell leukemia cell line) had no effect on the standard curves, as shown by complete overlapping of the standard curves in the presence (blue diamond) or absence (red square) of the unrelated Jurkat total RNA. The negative control produced no amplification (data not shown). Uniform dissociation (melting) curves for all tested miRNA concentration indicate an absence of non-specific amplification products (data not shown). This example demonstrates that the sensitivity (signal-to-noise ratio) of miROID is not affected by the presence of cellular RNAs (including miRNAs and other small RNAs).

Example 10

Detection of Endogenous miRNAs in Total Cellular RNA and Cell Lysate in miR-ID Assays (A) Using total RNA from Jurkat cells. Total RNA from Jurkat cells was isolated using Trizol kit following recommended protocol (Invitrogen/Life Technologies). Various amounts (20 ng, 2 ng, 0.2 ng and 20 pg) of total RNA from Jurkat cells were incubated with 5 U/µl CircLigase II (Epicentre) at 60° C. for 1 h in the appropriate buffer as described in Example 1. In the multiplex RT step, one-fourth volumes of the circularization reaction samples were mixed with 100 nM RT primers miR16-RT, let-7bRT and 127RT10 primer (Table 1). The RT primers were simultaneously extended by SuperScript II reverse transcriptase for 2 h at 42° C. as described in Example 3. In the qPCR step, one-tenth volume of each RT reactions was assayed by real-time qPCR using 150 nM 5'-overlapping PCR primers: mir-16 specific primers; miR-16Fwd and miR-16Rev; let-7b-specific primers, let7bmatF and let-7bmatR; and the miR-127-specific PCR primers, 127Fwd and 127RT19 (Table 1). All these PCR primers had 15-16 nt of overlap at their 5' ends and 3-nt overhangs at their 3' ends. The qPCR reactions were carried out in duplicate and as described in Example 5 except that the annealing temperature was 58° C. Ct values were exported and analyzed using 2008 Microsoft Excel software to plot the standard curve (FIG. 36A). All obtained $C_t$ values were in the range of linearity with the log of the miRNA input. Results indicate robust detection of endogenous miRNAs let-7b and miR-16 even in 20 pg of total RNA comparable to an average amount of RNA from a single cell (Yu et al. 2006). At the same time miR-127, which is not expressed in these cells (Yu et al. 2006), provided the background level (Ct~40) at all total RNA concentration tested. Uniform dissociation (melting) curves for all tested miRNA concentration indicate an absence of non-specific amplification products for both let-7b and miR-16 (data not shown).

(B) Using cell lysate preparation from Jurkat cells. Total RNA was isolated as described above and Jurkat cell lysates were prepared using the Nucleic Acid purification lysis solution (ABI/Life Technologies) according to the recommended protocol. Various amounts (2 ng, 0.2 ng and 20 pg) of total RNA and corresponding equivalent amounts of cell lysate were subjected to circularization by CircLigase II as described in Example 1. In the RT step, one-fourth volumes of the circularization reaction samples were mixed with 100 nM RT primer let-7bRT (Table 1), which was extended by SuperScript II reverse transcriptase for 2 h at 42° C. as described in Example 3. In the qPCR step, one-tenth volume of each RT reactions was assayed by real-time qPCR using 150 nM 5'-overlapping PCR primers let7bmatF and let-7bmatR (Table 1) as described in Example 5. All qPCR reactions were done in duplicate. Ct values were exported and analyzed using 2008 Microsoft Excel software to plot the standard curve. The obtained Ct values were plotted against the initial, total RNA/lysate inputs in the circularization reaction. All obtained $C_t$ values were in the range of linearity with the log of the miRNA input. Results indicate robust detection of endogenous miRNAs let-7b even in 20 pg of total RNA comparable to an average amount of RNA from a single cell. The detection of the same miRNA in purified fraction of total RNA extracted from the same cells provides only marginally better sensitivity (ΔCt~2) compared to the crude cell lysate (FIG. 36B).

This example demonstrates that miR-ID can work efficiently and specifically even in the presence of cellular RNA and DNA molecules implying no needs for a purification step isolating small RNA fraction containing miRNA.

Example 11

Linear Fold-change Values of Mouse miRNAs in Total RNA Extracted from Various Tissues Determined by miR-ID 100 ng of mouse total RNA from brain, heart, liver, thymus, lung, embryo and ovary (Applied Biosystems: AM7800) were subjected to T4 RNA Ligase 1 mediated circularization (in duplicate) as described in Example 1. The circularization reaction was done in duplicate, followed by a Reverse Transcription reaction as described in Example 3, simultaneously using let-7aRT, miR-16RT, miR-20RT, miR-21 RT, miR-22RT and sno234RT (Table 1) in a final concentration of 100 nM each. Sno234 (small nucleolus RNA) was utilized as the endogenous reference for normalization of RNA input and efficiency of RT-PCR reactions. In qPCR step, one-tenth volume of each RT reactions was assayed by real-time qPCR using 150 nM 5'-overlapping PCR primers: Let-7a specific primers, let-7aFwd and let-7aRev; miR-16 specific primers, miR-16Fwd miR-16Rev; miR-20 specific primers, miR-20Fwd miR-20Rev; miR-21 specific primers, miR-21 Fwd miR-21 Rev; miR-22 specific primers, miR-22Fwd miR-22Rev; and sno234 specific primers, sno234Fwd and sno234Rev (Table 1). All these PCR primers had 15-16 nt of overlap at their 5' ends and 3-nt overhangs at their 3' ends. The qPCR reactions were carried out in duplicate and as described in Example 5. Ct values were exported and analyzed using 2008 Microsoft Excel software. Each value is an average of 4 qPCR measurements. Average (R=0.86) linear fold expression values for miRNAs let-7a, miR-16, miR-20, miR-21 and miR-22 relative to the liver expression (chosen as the calibrator tissue, in which expression value was normalized to 1) is shown (FIG. 37). Overall, the found relative miRNA expression levels were in good correlation (R=0.78) with the expression profiles previously obtained by TaqMan micro RNA assay (Chen et al. 2005), despite difference in choice of endogenous reference gene. In this example, we used sno234 RNA as the endogenous reference for normalization of RNA input and efficiency of RT-PCR reactions rather than GAPDH mRNA used by Chen and co-workers.

Example 12

Discrimination Between 2'-OH and 2'-OMe miRNA Forms in miR-ID Assays Using T4RNA Ligase 1 and CircLigase in the Circularization Step (A) miRNA circularization by T4 RNA ligase 1 and CircLigase II provide similar standard curves. Various concentrations (0.2 nM, 0.02 nM, 2 pM, 0.2 pM, 0.02 pM, 2 fM and 0.2 fM) of synthetic let-7b having a 5'-p and 2'-OH/3'-OH at its 3' end were subjected to circularization by T4 RNA ligase 1 or CircLigase II in separate reactions as described in Example 1. In the RT step, one-tenth volume of each circularized miRNA sample was mixed with 100 nM let7bRT primer (Table 1), and extended by SuperScript II reverse transcriptase for 2 h at 42° C. as described in Example 3. In the real-time qPCR step, one-tenth volume of each RT reaction was assayed using 150 nM 5'-overlapping PCR primers: let-7bFwd and let-7bRev (Table 1). The total dilution of the let-7b inputs from Step 1 to step 3 was 100-fold and the final (post-dilution) concentrations are shown. The qPCR reactions were done in duplicate and carried out as described in example 5. Ct values were exported and analyzed using Microsoft Excel software to plot the standard curve (FIG. 38A). All obtained $C_t$ values were in the range of linearity with the log of the miRNA input. The negative control produced no amplification (data not shown). Uniform dissociation (melting) curves for all tested miRNA concentration indicate an absence of non-specific amplification products (data not shown). This example demonstrates that these two RNA ligases, which have very similar circularization efficiency (see FIG. 27B), also provide similar standard curves for normal human miRNAs carrying 2'-OH group at its 3' end (2'-OH miRNAs).

(B) Identification and detection of miRNAs having 2'-OMe modification at their 3' ends (2'-OMe miRNAs). Synthetic miRNAs (let-7g, let-7b and miR-16; Table 1), having a 5'-p and a 2'-OMe/3'-OH at the 3' end were subjected to circularization by T4 RNA ligase 1 or CircLigase II as described in Example 1. In the RT step, one-fourth volume of each circularized miRNA sample was mixed with 100 nM specific RT primers; let-7b/7g RT and miR-16RT (Table 1) and simultaneously extended by SuperScript II reverse transcriptase for 2 h at 42° C. as described in Example 3. In the real-time qPCR step, one-tenth volume of each RT reaction was assayed using let-7b, let-7g and miR-16 specific 150 nM 5'-overlapping PCR primers (Table 1). The qPCR reactions were carried out in duplicate and as described in Example 5. Ct values were exported and analyzed using Microsoft Excel software. Relative signal intensity was calculated by normalizing the Ct obtained by using T4 RNA Ligase 1, relative to the Ct obtained by using CircLigase II for each miRNA. To confirm the sensitivity of T4 RNA Ligase 1 and ability of CircLigase to circularize small RNAs containing a 2'-OMe/3'-OH at the 3' end in a biological system, 100 ng of total RNA from *A. thaliana* leaf tissue was subjected to circularization, reverse transcription and qPCR (as described for the synthetic miRNAs above) using both T4 RNA Ligase 1 and Circ Ligase II enzymes to quantify ath-miR-171 (Table 1 for miR-171 specific RT and qPCR primers); known to be highly expressed in *Arabidopsis* (Xie et al. 2005). Relative signal intensity recorded for miR-171 using both T4 RNA Ligase 1 and CircLigase (at the circularization step) is also shown (FIG. 38B).

The 2'-OMe miRNAs, which were tested in this example had different 3'-end nucleotides as indicated in FIG. 38B (bottom panel). The results demonstrate that that miR-ID can detect small RNAs carrying both 2'-OH and 2'-OMe groups at their 3' ends RNAs as well as distinguish them from each other using similar ability of CircLigase and T4RNA Ligase 1 to circularize the 2'-OH miRNAs but significantly different abilities of these enzymes to circularize the 2'-OMe miRNAs. The discrimination between these miRNA forms seems do not significantly affected by the different 3' end nucleotides.

(C) Determination of percentage methylation of synthetic miRNAs using T4 RNA Ligase 1 and CircLigase II in miR-ID assays. Synthetic let-7b miRNAs, which had 5'-p and either 2'-OH/3'-OH or 2'-OMe/3'-OH at the 3' end, were mixed in different pre-defined proportions of the 2'-OMe modification (0%, 25%, 50%, 75% and 100%) keeping the total concentration constant at 20 pM. Identical samples of these mixtures were circularized using either T4 RNA Ligase 1 or CircLigase II in duplicate as described in Example 1. Five µl from each of these two circularization reactions was used individually as template for reverse transcription with let-7bRT primer (Table 1) as described in Example 3. The 2-µl aliquots from each of these reverse transcription reactions were used as template for qPCR reactions using let-7b specific 5'-overlapping primers (let-7bFwd and let-7bRev: Table 1) and all qPCR reactions were carried out in duplicate as described in Example 5. Ct values were exported and analyzed using Microsoft Excel software. A melting curve was plotted to validate presence of a single dominant amplification product. The Ct values obtained for the samples containing 100% of the 2'-OH let-7b form, which were treated with either T4 RNA ligase (Ct=12.4) or CircLigase (Ct=13.2) in the assay step 1, were compared and used to calculate a normalization coefficient (0.94). This coefficient, which implies slightly higher efficiency of T4 RNA ligase assay, was applied to normalize the data for other mixtures of the 2'-OH and 2'-OMe forms. The obtained data were plotted as shown (FIG. 38C), demonstrating the sensitivity of T4 RNA Ligase I in detection of defined amounts of 2'-OMe miRNA form in the mixture with the 2'-OH form. This example demonstrates miR-ID ability not only detect both 2'-OH and 2'-OMe miRNA forms but also to determine their ratio in samples.

Example 13

Testing Dynamic Range and Sensitivity of Detection of Modified MiR-Id Assay Using Overlapping Combo Primers and Taqman Probes (MiR-Id-Taqman Assay)

In this example, we used overlapping combo primers rather than the 5'-overlapping primers used in the default miR-ID assay (Example 5). These combo primers are specific to target miRNA repetitive sequences at their 3' ends and have Tag sequence (i.e. Zip-code) uniquely designated (but not related) to the target (FIG. 11A). We designed custom TaqMan probe complementary to the Tag sequence and used it for the assay presented in FIG. 13B. Various concentrations (1.3 nM, 0.13 nM, 13 pM, 1.3 pM, 0.13 pM, 13 fM and 1.3 fM) of synthetic lin-4, which had 5'-p and 2'-OH/3'-OH at the 3' end, were subjected to circularization (in duplicate) by 0.67 U/µl T4 RNA ligase 1 (NEB) as described in Example 1. A 50 µl reverse transcription reaction was set up as described in Example 3 containing the lin4RT primer (Table 1) at a final concentration of 100 nM. In the next step, qPCR was carried out to amplify the cDNA generated by RT using lin-4 specific 5'-overlapping primer pairs of 43-nt each (lin4ZipCodeF and lin4ZipCodeR: Table 1), which had a common 24 nt 5' tail sequence, followed by a 19-nt sequence specific to lin-4. The 24 nt 5' tail sequence was complementary to the 24 nt lin-4 TaqMan probe (Table 1), which was one of the zip-code sequences as described by Gerry et al. (1999). 2 µl aliquots of the RT reactions were analyzed by real-time qPCR with 150 nM lin-4ZipCodeF and R primers as described in Example 5 with the following modified cycling conditions. The qPCR reaction included initial denaturation at 95° C. for 10 min, 2 cycles of (95° C. for 45 sec/56° C. for 45 sec/67° C. for 1 min) followed by 45 cycles of (95° C. for 15 sec/67° C. for 1 min). All qPCR reactions were done in duplicate and the fluorescence recording was done at the 67° C. for 1 min step. Ct values were exported and analyzed using Microsoft Excel software to plot the standard curve (FIG. 40). All obtained Ct values were in the range of linearity with the log of the miRNA input. The negative control produced no amplification (data not shown).

We directly compared the standard curves obtained by miR-ID-TaqMan with those for TaqMan microRNA assays. The same (as for miR-ID) dilution series of miRNA lin-4 were used in TaqMan microRNA RT-PCR assay performed as described in Example 5. We also plotted the TaqMan standard curve for lin-4, which was previously published (Chen et al. 2005) to demonstrate our ability to reproduce their results. Based on ΔCt=5 between the miR-ID-Taq and ABI's TaqMan standard curves (both the experimental and published curves were very close), the former assay was found about 30-times less sensitive than the latter assay that would be explained by the use of non-optimized Taq sequence and TaqMan probes. In contrast, proprietary (ABI) TaqMan probes undergone extensive optimization before making them commercially available. We developed the miR-ID-TaqMan as prototype for multiplex RT-PCR assay, in which multiple target miRNAs would be assayed simultaneously in the same samples using target-specific combo primers and primer-specific TaqMan probes carrying different fluorophores designated to different targets. This example made demonstrates a feasibility of such multiplex assay based on miR-ID-TaqMan approach.

Example 14

Testing Sensitivity and Dynamic Range of Detection of Modified MiR-Id Assay Using Isothermal Strand-displacement Technique Instead of PCR for Signal Amplification (miRSA assay)

In this example we used new method, which shares the same circularization (FIG. 1A) and RT-RCA steps (FIG. 2A) with miR-ID, but differs in step 3. In this last step, miRSA use isothermal, hyperbranched strand-displacement (HSDA) reaction (FIG. 7) rather that PCR (FIG. 6A) while both methods employ similar 5'-overlapping primer pairs. The design of these primers for the same miRNA targets slightly varied accommodating the annealing/extension temperature differences in these assays.

(A) Semi-quantitative validation of miRSA assay using synthetic lin-4. Various concentrations (20 pM, 20 fM, and 20 aM) of synthetic cel-lin-4, which had 5'-p and 3'-OH ends, were subjected to circularization as described in Example 1. A 50 µl reverse transcription reaction containing 5 µl of the circularized lin-4 RNA and lin4RT primer (Table 1) at a final concentration of 100 nM was set up as described in Example 3. 5 µl of each RT reaction was assayed by HSDA using primers lin4HSDAFwd and lin4HSDARev (Table 1), which had 18 bp of 5'-overlap and 3-nt 3'-overhang. A 50-µl reaction was set up containing the 5'-overlapping PCR primers at a final concentration of 1 µM, 400 µM dNTPS, 0.16 U/µl Bst DNA polymerase (NEB) in the recommended buffer (20 mM Tris-HCl, 10 mM $(NH_4)_2SO_4$, 10 mM KCl, 2 mM $MgSO_4$, 0.1% Triton X-100, pH 8.8) and incubated for 20 min at 60° C. The HSDA branched multimer DNA products were separated on a 3% agarose gel and stained with ethidium bromide (FIG. 41A). The products were identified as follows. Lane L: 100 bp DNA ladder. Lane 1 is the negative control with no circular lin-4 added. Lanes 2, 3 and 4: HSDA products with 20 aM, 20 fM and 20 pM amounts of synthetic lin-4 in the circularization reaction. This example demonstrates very fast signal amplification by HSDA and suggests very high sensitivity of this approach.

Figure 41B:
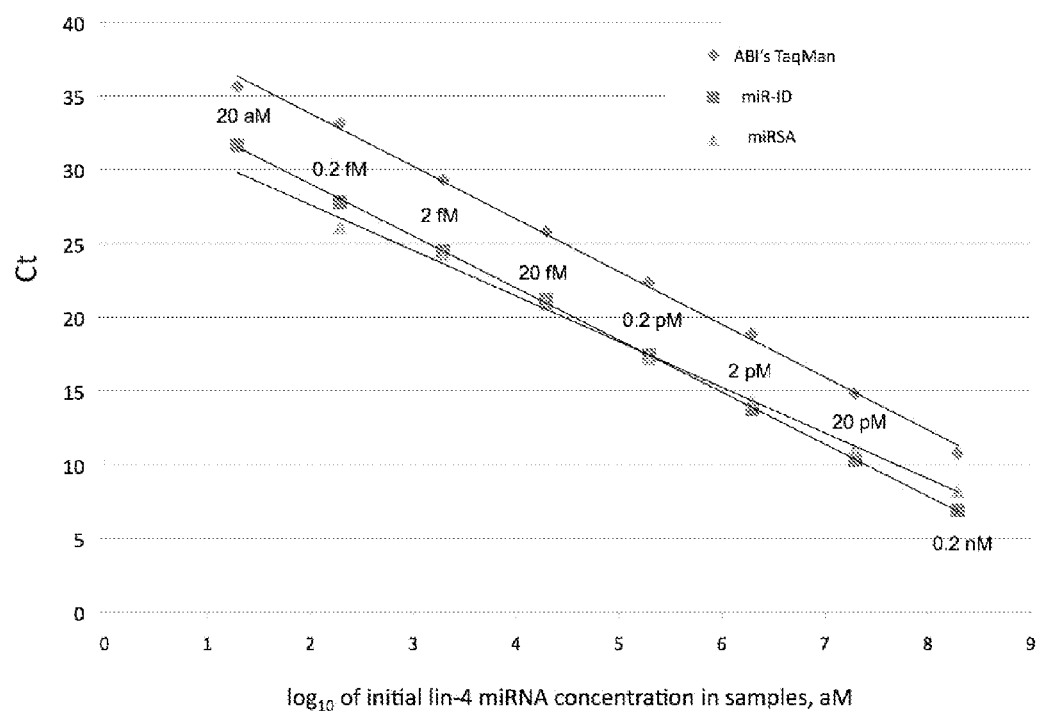

(B) Determining sensitivity, dynamic range and detection limit of miRSA assay using real-time, quantitative signal detection. For this purpose, a single-dye (EVA Green) based detection system was set up. Various concentrations (0.2 nM, 0.02 nM, 2 pM, 0.2 pM, 0.02 pM, 2 fM, 0.2 fM and 0.02 fM) of synthetic lin-4, which had 5'-p and 2'-OH/3'-OH at the 3' end, were subjected to circularization by 0.67 U/µl T4 RNA ligase 1 (NEB) as described in Example 1. A 50 µl reverse transcription reaction was set up as described in Example 3 containing the lin4RT primer (Table 1) at a final concentration of 100 nM. 5 µl of each RT reaction was assayed by HSDA using primers lin4HSDAFwd and lin4HSDARev (Table 1) as described above, but using Eva Green for real-time quantification and detection. A 20 µl reaction was set up (in duplicate) containing the 5' overlapping primers at a final concentration of 500 nM, 400 µM dNTPS, 0.4 U/µl Bst DNA polymerase (NEB) in the recommended buffer as described above along with 1× Eva Green dye (Biotium). The reaction tubes were incubated at 60° C. in a qPCR machine which was programmed to take a fluorescent reading every 80 sec for 40 min. Ct values were exported and analyzed using Microsoft Excel software to plot the standard curve (FIG. 41B). All obtained Ct values were in the range of linearity with the log of the miRNA input. The negative control produced no amplification (data not shown).

We directly compared the standard curves obtained by these alternative variants of miR-ID assay (see FIG. 41B). Our results indicate that both miR-ID and miRSA provides very similar sensitivities, which are about 30 times better than that for ABI's TaqMan assay (see FIG. 41B). However, the HSDA step requires only 60 min (and reaction time can be further reduced without losing sensitivity) whereas the miR-ID qPCR step requires significantly longer time.

Figure 41C:
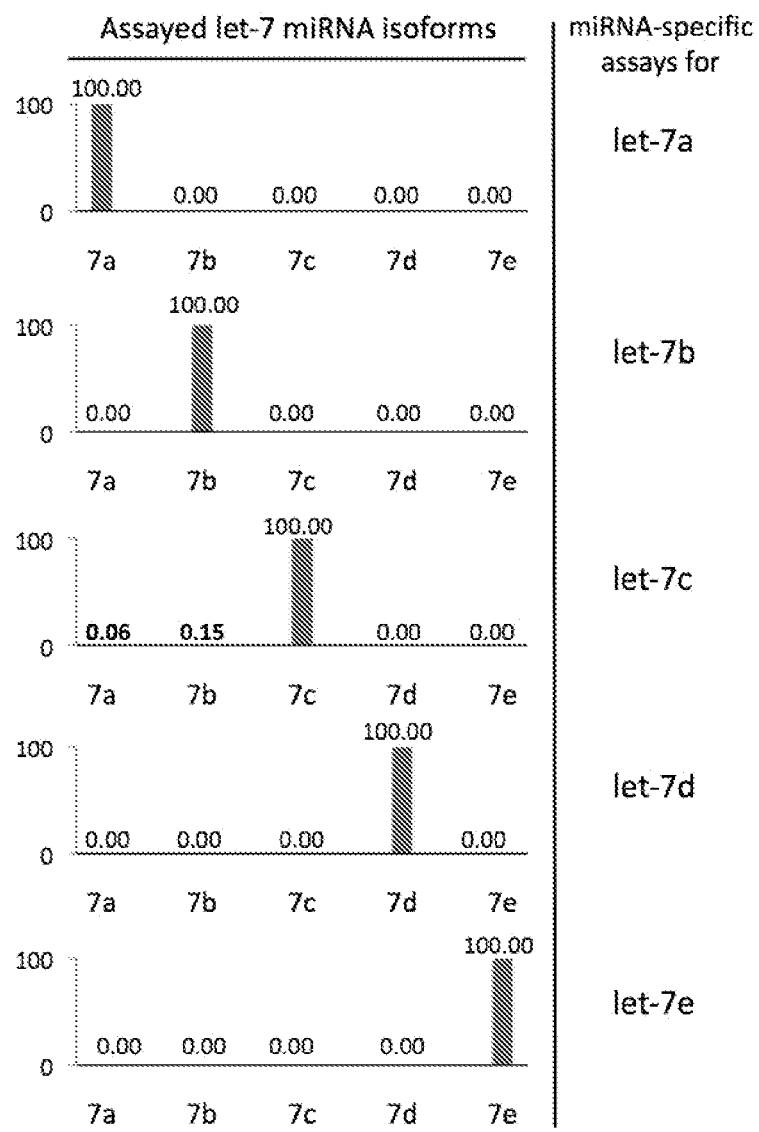

(C) Demonstration of miRSA assay specificity by discrimination of closely related let-7 miRNA isoforms. Synthetic miRNAs let-7a, let-7b, let-7c, let-7d and let-7e (Table 1) containing 2'-OH at its 3'-end and 5'-phosphate, were individually circularized by T4 RNA ligase 1 as described in Example 1. These homologous miRNAs have only 1 or 2 nucleotide differences between each other (FIG. 33A). The circularized let-7 miRNA isoforms (one-tenth volume of circularization reactions) were used as template for the 50 µl reverse transcription reaction, which were individually performed for each miRNA, using universal 7acdRT primer (for let-7a, c and d) or specific 7eRT and 7bRT primer (for let-7b and 7e) (Table 1) at a final concentration of 100 nM as described in Example 3. In next step, 5 µl of each RT reaction was assayed by HSDA as described in Panel B. Each isoform-specific RT reaction was subjected to the HSDA reaction (in duplicate) in a cross-reactive manner. For example, 5 µl of the RT product of let-7a was used as template for HSDA with 5'-overlapping HSDA primers specific for let-7a, let-7b, let-7c, let-7d and let-7e (primer sequences in Table 1) in five separate reactions. Ct values were exported and analyzed using Microsoft Excel software. The maximum signal in each assay was normalized to 100, and the remaining values were calculated relative to the maximum signal. Data was plotted on a linear scale (FIG. 41C). There were no non-specific amplifications recorded. Analysis of the discrimination factors between the let-7 isoforms assayed in cross-reaction manners demonstrates that miRSA (FIG. 41C) provides superior sequence-specificity as compared to miR-ID (FIG. 33B).

These examples demonstrate that miRSA has great potential as alternative approach for miRNA detection. The lower cost (no needs for thermocycling equipment) and fast signal amplification makes of this assay particularly appropriate for point-of-care diagnostic applications.

Example 15

Attachment of Adenylated Adapter to 2'-OH and 2'-OMe miRNAs by T4RNA ligase 1

Two synthetic let-7b miRNAs, one containing 2'-OH and another 2'-OMe at their 3'-ends, were $^{32}$P-phosphorylated at their 5' ends as described in Examples 1-2. 5'-$^{32}$P-labeled linear miRNAs (140 nM) were mixed with 5 µM non-radioactive adenylated oligonucleotide: rAppCTGTAGGCAC-CATCAAT/3ddC/ (SEQ ID NO:89) (which is commercially available from IDT and was used here as a model for the adenylated adapters used in our miR-AC schemes—see FIGS. 14, 16 and 17), and incubated with 0.67 Uµl T4 RNA Ligase 1 (NEB) in the presence or absence of 1 mM ATP in standard ligation buffer at 37° C. (see Example 2). Aliquots were taken after 1 min, 1 hour and 19 hours, and reaction products were analyzed in denaturing 15% polyacrylamide gel along with DNA ladders marked as L (FIG. 42). Lanes 1-4 corresponds to 1min, lanes 5-8- to 1 h, and lanes 9-12 - to 19 h points. Lanes 1-2, 5-6, and 9-10 had ATP whereas lanes 3-4, 7-8, and 11-12 had not. Lanes 1, 3, 5, 7, 9 and 11 corresponds to the 2'-OH miRNA whereas lanes 2, 4, 6, 8, 10 and 12 - to the 2'-OMe miRNA. The products were identified as follows: Lane 1: unchanged linear 2'-OH miRNA. Lane 2: unchanged linear 2'-Ome miRNA. Lane 3: mixture of linear 2'-OH miRNA partially (>50% after 1 min reaction) ligated with the cloning linker. The miRNA-DNA linker product was up shifted in the gel. Lane 4: linear 2'-OMe miRNA partially (<5% after 1 min reaction) ligated with the cloning linker. Lane 5: circularized 2'-OH miRNA. Circular miRNA (CT) moves little faster in the gel than its linear form (LT). Lane 6: linear 2'-OMe miRNA partially (>50% after 1 h reaction) adenylated. The adenylated form moves little slower in the gel than the unmodified linear miRNA. Lane 7: linear 2'-OH miRNA fully ligated with the cloning linker after 1 h reaction. Lane 8: linear 2'-OMe miRNA fully ligated with the cloning linker after 1 h reaction. Lane 9: circularized 2'-OH miRNA. Lane 10: linear 2'-OMe miRNA partially (>90after 1 h reaction) adenylated. Lane 11: linear 2'-OH miRNA fully ligated with the cloning linker after 19 h reaction. Lane 12: linear 2'-OMe miRNA fully ligated with the cloning linker after 19 h reaction. The adenylated DNA linker, which has a blocking group at its 3' end to prevent self-ligation, was ligated to miRNAs quickly regardless of whether it had 2'-OH or 2'-OMe ends. In the absence of ATP, the 2'-OH end provides faster adapter ligation to miRNA than the 2'-OMe end (compare lanes 3 and 4), but both ligation reactions were fully completed after 1 h (lanes 7 and 8). No circularization of the 2'-OH miRNAs occurred in the absence of ATP whereas, in the presence of ATP, no ligation of the 2'-OH miRNA with the adapter occurred. Instead, this miRNA underwent complete circularization after 1 h (lane 5). The 2'-OMe miRNA could not be circularized by T4 RNA ligase 1. Instead this miRNA was partially converted into its adenylated form (after 1 h) and fully (after 19 h) (lanes 6 and 10, respectively; see also Example 2 and FIG. 28A).

This example demonstrates that: (1) an adenylated adapter/linker can be efficiently ligated to 2'-OMe miRNAs (as well as to 2'-OH miRNAs that was shown previously by others) by T4 RNA ligase in the absence of ATP; and (2) 2'-OMe RNA can be easily adenylated by T4 RNA ligase in the presence of ATP without self-circularization. The last point also implies that the adenylated 2'-OMe RNA then can be ligated to the adapter carrying 5'-p and 3'-OH in the absence of ATP (FIG. 16) or used as 3' end blocking group in RNA/DNA adapters as shown in FIG. 14B and FIG. 17.

TABLE 1

Sequences of miRNAs and primers used in the above Examples

| Name | Sequence (5'→3') |
|---|---|
| cel-lin-4 | UCCCUGAGACCUCAAGUGUGA (SEQ ID NO: 1) |
| hsa-let-7a | UGAGGUAGUAGGUUGUAUAGUU (SEQ ID NO: 2) |
| hsa-let-7b | UGAGGUAGUAGGUUGUGUGGUU (SEQ ID NO: 3) |
| hsa-let-7c | UGAGGUAGUAGGUUGUAUGGUU (SEQ ID NO: 4) |
| hsa-let-7d | AGAGGUAGUAGGUUGCAUAGU (SEQ ID NO: 5) |
| hsa-let-7e | UGAGGUAGGAGGUUGUAUAGU (SEQ ID NO: 6) |
| hsa-let-7g | UGCGGUAGUAGUUUGUACAGUA (SEQ ID NO: 7) |
| mmu-miR-16 | UAGCAGCACGUAAAUAUUGGCG (SEQ ID NO: 8) |
| mmu-miR-20 | UAAAGUGCUUAUAGUGCAGGUAG (SEQ ID NO: 9) |
| mmu-miR-21 | UAGCUUAUCAGACUGAUGUUGA (SEQ ID NO: 10) |
| mmu-miR-22 | AAGCUGCCAGUUGAAGAACUGU (SEQ ID NO: 11) |
| hsa-miR-23a | AUCACAUUGCCAGGGAUUUCC (SEQ ID NO: 12) |
| hsa-miR-127 | UCGGAUCCGUCUGAGCUUGGCU (SEQ ID NO: 13) |
| ath-miR-171a | UGAUUGAGCCGCGCCAAUAUC (SEQ ID NO: 14) |
| hsa-miR-221 | AGCUACAUUGUCUGCUGGGUUUC (SEQ ID NO: 15) |
| RNA 19 | UGAGGUUUAGGAUUCGUGC (SEQ ID NO: 16) |
| pre7b1 | UGAGGUAGUAGGUUGUGUGGUUUCAGGGCAGUGAUGU (SEQ ID NO: 17) |
| pre7b2 | UGCCCCUCGGAAGAUAACUAUACAACCUACUGCCUUCC (SEQ ID NO: 18) |

Reverse Transcription Primers and splint oligonucleotides

| Name | Sequence (5'→3') |
|---|---|
| lin-4RT | GTCTCAGGGA (SEQ ID NO: 19) |
| lin-4RTSplint | TCTCAGGGATCA (SEQ ID NO: 20) |
| let-7a/c/d/g RT | CTACTACCTC (SEQ ID NO: 21) |
| let-7bRT | CTCAAACCAC (SEQ ID NO: 22) |
| 7bRT10 | CACAACCTAC (SEQ ID NO: 23) |
| 7bRT12 | CACACAACCTAC (SEQ ID NO: 24) |
| 7bRT14 | ACCACACAACCTAC (SEQ ID NO: 25) |
| let-7eRT | CTCCTACCTC (SEQ ID NO: 26) |
| miR-16RT | CGTGCTGCTA (SEQ ID NO: 27) |
| miR-20RT | CACTATAAGCACT (SEQ ID NO: 28) |
| miR-21RT | AGTCTGATAAGCT (SEQ ID NO: 29) |
| miR-22RT | CTGGCAGCTT (SEQ ID NO: 30) |
| miR-23aRT | GGCAATGTGAT (SEQ ID NO: 31) |
| miR-127RT10 | AGACGGATC (SEQ ID NO: 32) |
| miR-127RT19 | CAAGCTCAGACGGATCCGA (SEQ ID NO: 33) |
| miR-171aRT | GGCTCAATCA (SEQ ID NO: 34) |
| sno-234RT | CAGTTCCAAAAG (SEQ ID NO: 35) |

TABLE 1-continued

Sequences of miRNAs and primers used in the above Examples

| Name | Sequence (5'→3') |
|---|---|
| qPCR DNA Primers | |
| lin-4Fwd | CTCAAGTGTGATCCCTGAG (SEQ ID NO: 36) |
| lin-4Rev | AGGGATCACACTTGAGGTC (SEQ ID NO: 37) |
| lin-4ZipCodeF | GCTGCGATCGATGGTCAGGTCCTGAGTGTGATCCCTGAGACCT (SEQ ID NO: 38) |
| lin-4ZipCodeR | GCTGCGATCGATGGTCAGGTGCTGTCTCAGGGATCACACTTGA (SEQ ID NO: 39) |
| lin4-TaqManProbe | CAGGACCTGACCATCGATCGCAGC (SEQ ID NO: 40) |
| let-7aFwd | GAGGTAGTAGGTTGTATA (SEQ ID NO: 41) |
| let-7aRev | ACAACCTACTACCTCAAA (SEQ ID NO: 42) |
| let-7bFwd1 | GGTAGTAGGTTGTGTGGT (SEQ ID NO: 43) |
| let-7bRev1RT | ACACAACCTACTACCTCA (SEQ ID NO: 44) |
| Let7bComboR | GACCACCTTGCGATCGGGTACAGCCTACTACCTCA (SEQ ID NO: 45) |
| Let7bComboF | TGCGGGTACAGCACCTACCTTGCGGTTGTGTGGTT (SEQ ID NO: 46) |
| let-7bFwd2 | GTTTGAGGTAGTAGGTTGTG (SEQ ID NO: 47) |
| let-7bRev2 | AACCTACTACCTCAAACCAC (SEQ ID NO: 48) |
| Let7bmatF | GAGGTAGTAGGTTGTGTG (SEQ ID NO: 49) |
| Let7bmatR | ACAACCTACTACCTCAAA (SEQ ID NO: 50) |
| let-7cFwd | GAGGTAGTAGGTTGTATG (SEQ ID NO: 51) |
| let-7cRev | ACAACCTACTACCTCAAA (SEQ ID NO: 52) |
| let-7dFwd | GTAGAGGTAGTAGGTTGC (SEQ ID NO: 53) |
| let-7dRev | ACCTACTACCTCTACTAT (SEQ ID NO: 54) |
| let-7eFwd | TTGTATAGTTGAGGTAGG (SEQ ID NO: 55) |
| let-7eRev | ACCTCAACTATACAACCT (SEQ ID NO: 56) |
| let-7gFwd | GAGGTAGTAGTTTGTACAGTA (SEQ ID NO: 57) |
| let-7gRev | TGTACAAACTACTACCTCATA (SEQ ID NO: 58) |
| miR-16Fwd | AGCACGTAAATATTGGCG (SEQ ID NO: 59) |
| miR-16Rev | CCAATATTTACGTGCTGC (SEQ ID NO: 60) |
| miR-20Fwd | GCAGGTAGTAAAGTGCTTAT (SEQ ID NO: 61) |
| miR-20Rev | AGCACTTTACTACCTGCACT (SEQ ID NO: 62) |
| miR-21Fwd | GATGTTGATAGCTTATCAGAC (SEQ ID NO: 63) |
| miR-21Rev | TGATAAGCTATCAACATCAGT (SEQ ID NO: 64) |
| miR-22Fwd | CTGCCTGTTGAAGAACT (SEQ ID NO: 65) |
| miR-22Rev | TTCTTCAACTGGCAGCT (SEQ ID NO: 66) |
| miR-23aFwd | TCACATTGCCAGGGAT (SEQ ID NO: 67) |
| miR-23aRev | CCTGGCAATGTGATGG (SEQ ID NO: 68) |
| miR-127Fwd | GATCCGTCTGAGCTTGGCT (SEQ ID NO: 69) |
| miR-127RT19 | CAAGCTCAGACGGATCCGA (SEQ ID NO: 70) |

TABLE 1-continued

Sequences of miRNAs and primers used in the above Examples

| Name | Sequence (5'→3') |
|---|---|
| miR-171aFwd | CCGCGCCAATATCTGA (SEQ ID NO: 71) |
| miR-171aRev | GATATTGGCGCGGCTC (SEQ ID NO: 72) |
| sno-234Fwd | AAAAATTCGTCACTACCACTG (SEQ ID NO: 73) |
| sno-234Rev | TGGTAGTGACGAATTTTGTT (SEQ ID NO: 74) |

Zip Code DNA Primers

| ZC1 | GACCACCTTGCGATCGGGTACAGC (SEQ ID NO: 75) |
|---|---|
| ZC2 | TGCGGGTACAGCACCTACCTTGCG (SEQ ID NO: 76) |

HSDA DNA primers

| lin4HSDAFwd | CTCAAGTGTGATCCCTGAGAC (SEQ ID NO: 77) |
|---|---|
| lin4HSDARev | TCAGGGATCACACTTGAGGTC (SEQ ID NO: 78) |
| Let7aHSDAFwd | TTTGAGGTAGTAGGTTGTATA (SEQ ID NO: 79) |
| Let7aHSDARev | ACAACCTACTACCTCAAACTA (SEQ ID NO: 80) |
| Let7bHSDAFwd | TTTGAGGTAGTAGGTTGTGTG (SEQ ID NO: 81) |
| Let7bHSDARev | ACAACCTACTACCTCAAACCAC (SEQ ID NO: 82) |
| Let7cHSDAFwd | TTTGAGGTAGTAGGTTGTATG (SEQ ID NO: 83) |
| Let7cHSDARev | ACAACCTACTACCTCAAACCAT (SEQ ID NO: 84) |
| Let7dHSDAFwd | ATAGTAGAGGTAGTAGGTTGC (SEQ ID NO: 85) |
| Let7dHSDARev | ACCTACTACCTCTACTATGCA (SEQ ID NO: 86) |
| Let7eHSDAFwd | AGGTTGTATAGTTGAGGTAGG (SEQ ID NO: 87) |
| Let7eHSDARev | ACCTCAACTATACAACCTCCT (SEQ ID NO: 88) |

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

REFERENCES

Ahmed, F. E. 2007. *Expert Rev. Mol. Diagn.* 7: 569-603.
Allawi, H. T. et al. 2004. *RNA* 10: 1153-61.
Aravin, A., Tuschl, T. 2005. *FEBS Lett.* 579: 5830-40.
Aravin, A. A. et al. 2007. *Science* 318: 761-4.
Arnaud-Barbe et al. 1998. *Nucleic Acids Res.* 26: 3550-4.
Babak, T. et al. 2004. *RNA* 10: 1813-9.
Barad, O. et al. *Genome Res.* 14: 2486-94.
Bartel, D. P. 2004. *Cell* 116: 281-97.
Basyuk, E. et al. 2003. *Nucleic Acids Res.* 31: 6593-7.
Berezikov, E. 2006. *Genome Res.* 16: 1289-98.
Beuvink, I. et al. 2007. *Nucleic Acids Res.* 35: e52.
Blondal, T. et al. 2003. *Nucleic Acids Res.* 31: 7247-54.
Bonnet, G. et al. 1999. *Proc. Natl. Acad. Sci. USA* 96: 6171-6176.
Bortolin, S., Zastawny, R. L. 2007. U.S. Pat. No. 7,230,092.
Braasch, D. A. et al. 2002. *Nucleic Acids Res.* 30: 5160-7.
Brandis, J. et al. 2006. United States Patent Application US2006/0003337 A1.
Broude, N. E. et al. 2001. *Proc. Natl. Acad. Sci. USA* 98: 206-11.
Brownie, J. et al. 1997. *Nucleic Acids Res.* 25: 3235-41.
Brukner, I. et al. 2007. *Nat. Protoc.* 2: 2807-14.

Bushati, N., Cohen, S. M. 2007. *Annu. Rev. Cell Dev. Biol.* 23: 175-205.
Calin, G. A. et al. 2004. *Proc. Natl. Acad. Sci. USA* 101: 11755-60.
Cameron, V., Uhlenbeck, O. C. 1977. Biochemistry 16: 5120-6.
Cao, W. 2004. *Trends Biotechnol.* 22: 38-44.
Chamnongpol, S., Souret, F. 2008. *Biotechniques* 44: 129-31.
Chen, C. et al. 2005. *Nucleic Acids Res.* 33: e179.
Couttet, P. et al. 1997. *Proc. Natl. Acad. Sci. USA* 94: 5628-33.
Cullen, B. R. 2006. *Nat. Genet.* 38 Suppl.: S25-30.
Cummins, J. M. et al. 2006. *Proc. Natl. Acad. Sci. USA* 103: 3687-3692.
Cummins, J. M., Velculescu, V. E. 2006. *Oncogene* 25: 6220-7.
Davis, S. et al. 2006. *Nucleic Acids Res.* 34: 2294-304.
Dahl, F. et al. 2005. *Nucleic Acids Res.* 33: e71.
Delihas, N. 1995. *Mol. Microbiol.* 15: 411-4.
Demidov, V. V., Frank-Kamenetskii, M. D. 2004. *Trends Biochem. Sci.* 29: 62-71.
Dowson, E. P, Womble, K. E. 2007. International patent application (PCT) WO27024653 A2.
Dykxhoorn, D. M. 2007. *DNA Cell Biol.* 26: 239-49.
Ebhardt, H. A. et al. 2005. *Proc. Natl. Acad. Sci. USA* 102: 13398-403.
Enos, J. M. et al. 2007. *BioTechniques* 42: 378-81.
Esquela-Kerscher A., Slack, F. J. 2004. *Nat. Methods* 1: 106-7.
Esquela-Kerscher, A. Slack, F. J. 2006. *Nat. Rev. Cancer* 6: 259-69.
Fan, J. B. et al. 2000. *Genome Res.* 10: 853-60.
Fluiter, K. et al. 2005. *Oligonucleotides* 15: 246-54.
Frieden, M. et al. 1999. *Angew. Chem. Int. Ed. Engl.* 38: 3654-7.
Friedrich, M. et al. 2005. *DNA Seq.* 16: 53-7.
Gallo, S. et al. 2005. *Chimia* 50: 812-16.
Gerry, N. P. et al. 1999. *J. Mol. Biol.* 292: 251-62.
Getts, R. C. et al. 2006. United States Patent Application US2006/0094025 A1.
Gottwein, E. et al. 2007. *Nature* 450: 1096-9.
Grange T. 2008. *Methods Enzymol.* 448: 445-66.
Guo, Z. et al. 1997. *Nat. Biotechnol.* 15: 331-5.
Hammond, S. M. 2006a. *Curr. Opin. Genet. Dev.* 16: 4-9.
Hammond, S. M. 2006b. *Trends Mol. Med.* 12: 99-101.
Hammond, S. M. 2006c. *Nat. Methods.* 3: 12-3.
Hartig, J. S. et al. 2004. *J. Am. Chem. Soc.* 126: 722-3.
Hartl, D. L. et al. 1996. *Methods Mol. Biol.* 58: 293-301.
Hemat, F., McEntee, K. 1994. *Biochem. Biophys. Res. Commun.* 205: 475-81.
Hernando, E. 2007. *Clin. Transl. Oncol.* 9: 155-60.
Hertel, K. J. et al. 1998. *Biochemistry* 37: 16983-8.
Hjorleifsdottir, S. et al. 2007 U.S. Pat. No. 7,303,901.
Hirschhorn, J. N. et al. 2000. *Proc. Natl. Acad. Sci. USA* 97: 12164-9.
Ho, C. K., Shuman, S. 2002. *Proc. Natl. Acad. Sci. USA* 99: 12709-14.
Hopkins, J. F., Woodson, S. A. 2005. *Nucleic Acids Res.* 33: 5763-70.
Horwich, M. D. et al. 2007. *Curr. Biol.* 17: 1265-72.
Huang, Z., Alsaidi, M. 2003. *Anal. Biochem.* 322: 269-74.
Huang, Z., Szostak, J. W. 1996. *Nucleic Acids Res.* 24: 4360-1.
Huang, Z., Szostak, J. W. 2003. *Anal. Biochem.* 315:129-33.
Huang, S. et al. 2007. *Nucleic Acids Res.* 35: e101.
Hutvagner, G. et al. (2004) *PLoS Biol.* 2: E98.
Jacobsen, N. et al. 2005. International Patent Application (PCT) WO2005098029 A2.
Jiang, J. et al. 2005. *Nucleic Acids Res.* 33: 5394-403.
Jonstrup, S. P. et al. 2006. *RNA* 12: 1747-52.
Kandimalla, E. R. et al. 1995. *Nucleic Acids Res.* 23: 3578-84.
Kaufmann, G. et al. 1974. *FEBS Lett.* 46: 271-5.
Kim, V. N., Nam, J. W. 2006. *Trends Genet.* 22: 165-73.
Kool, E. T. 2000. U.S. Pat. No. 6,077,668.
Kool, E. T. 2002. U.S. Pat. No. 6,368,802.
Kong, D. et al. 2004. *Biotechnol Lett.* 26: 277-80.
Krichevsky, A. M. et al. 2003. *RNA* 9: 1274-81.
Krutzfeldt, J. et al. 2005. *Nature* 438, 685-9.
Kuhn, J., Binder, S. 2002. *Nucleic Acids Res.* 30: 439-46.
Lane, M. J. et al. 1998. U.S. Pat. No. 5,770,365.
Lao, K. Q., Livak, K. J. 2007. United States Patent Application US2007/0015187 A1.
Leary et al. 1991. *Gene* 106: 93-6.
Lee, Y. et al. 2002. *EMBO J.* 21: 4663-70.
Lewis, B. P. et al. 2005. *Cell* 120: 15-20.
Li, Q. et al. 2002. *Nucleic Acids Res.* 30: e5.
Li, J. et al. 2005. *Curr. Biol.* 15: 1501-7.
Li, J. et al. 2007. *BMC Biotechnol.* 7: 36.
Liang, R. Q. et al. 2005. *Nucleic Acids Res.* 33: e17.
Lim, L. P. et al. 2005. *Nature* 433: 769-73.
Lin, H. et al. 2006. *J. Am. Chem. Soc.* 128: 3268-72.
Liu, C. G. et al. 2004. *Proc. Natl. Acad. Sci. USA* 101: 9740-4.
Lizardi, P. M. 1998. U.S. Pat. No. 5,854,033.
Lizardi, P. M. et al. *Nat. Genet.* 19: 225-32.
Lu, J. et al. 2005a. *Nature* 435: 834-8.
Lu, D. P. et al. 2005b. *J. RNAi Gene Silencing* 1: 44-9.
Lu, C. et al. 2007. *Methods* 43: 110-7.
Luk, K. C. et al. 2007. *J. Virol. Methods.* 144: 1-11.
Maher, L. J., 3rd, Dolnick, B. J. 1988. *Nucleic Acids Res.* 16: 3341-58.
Maroney, P. A. et al. 2007. *RNA* 13: 930-6.
Mattie, M. D. et al. 2006. *Mol. Cancer.* 5: 24.
Meister, G. et al. 2004. *RNA* 10: 544-50.
Meyers, B. C. et al. 2006. *Curr. Opin. Biotechnol.* 17: 139-46.
Michael, M. Z. 2006. *Methods Mol. Biol.* 342:189-207.
Mishima, T. et al. 2007. *Brain Res.* 1131: 37-43.
Moore, M. J., Query, C. C. 2000. *Methods Enzymol.* 317: 109-23.
Mora, J. R., Getta, R. C. 2006. *Biotechniques* 41: 420-4.
Nandakumar, J., Shuman, S. 2004. *Mol. Cell.* 16: 211-21.
Neely, L. A. et al. 2006. *Nat. Methods* 3: 41-46.
Nelson, P. T. et al. 2004. *Nat. Methods* 1: 155-61.
Nichols, N. M. et al. 2008. *Curr. Protoc. Mol. Biol.* Chapter 3: Unit 3.15.
Nilsson, M. 2006. *Trends Biotechnol.* 24: 83-8.
Nuovo, G. J. et al. 2009. *Biotechniques* 46: 115-126.
Ohmichi, T., Kool, E. T. 2000. *Nucleic Acids Res.* 28: 776-83.
Orom, U. A. et al. 2006. *Gene* 372: 137-41.
Overhoff, M. et al. 2004. *Nucleic Acids Res.* 32: e170.
Pall, G. S. et al. 2007. *Nucleic Acids Res.* 35: e60.
Pan, X. et al. 2007. *J. Cell Physiol.* 211: 10-8.
Pfeffer, S. et al. 2005. *Curr. Protoc. Mol. Biol.* Chapter 26: Unit 26.4
Pfeffer, S., Voinnet, O. 2006. *Oncogene* 25: 6211-9.
Pierce, K. E. et al. 2005. *Proc. Natl. Acad. Sci. USA* 102: 8609-14.
Pinto, F. L. et al. 2006. *BMC Biotechnol.* 6: 31.
Polidoros, A. N. et al. 2006. *Biotechniques* 41: 35-6, 38, 40 passim.
Porkka, K. P. et al. 2007. *Cancer Res.* 67: 6130-5.
Potter S. S., Liang, H-C. 2006. United States Patent Publication US2006/0166245 A1.
Ramkissoon, S. H. et al. 2006. *Mol. Cell. Probes* 20:1-4.

Rana, T. M. 2004. United States Patent Application US2004/0175732 A1.
Ranjith-Kumar, C. T., Kao, C. C. 2006. *RNA* 12: 303-12.
Raymond, C. K. et al. 2005. *RNA* 11: 1737-44.
Raymond, C. K. 2007. United States Patent Publication US2007/0292878 A1.
Roberts, R. W., Crothers, D. M. 1991. *Proc. Natl. Acad. Sci. USA* 88: 9397-401.
Saba, R., Booth, S. A. 2006. *BMC Biotechnol.* 6: 47.
Sharbati-Tehrani, S. et al. 2008. *BMC Mol. Biol.* 9: 34.
Sharbati-Tehrani, S., Einspanier, R. 2008. European Patent Application EP1978104 A1.
Schellenberger, V. 1998. U.S. Pat. No. 5,756,316.
Schmittgen, T. D. et al. 2004. *Nucleic Acids Res.* 32: 43-53.
Seitz, H. et al. 2004. *Genome Res.* 14: 1741-8.
Shi, R., Chiang, V. L. 2005. *Biotechniques* 39: 519-25.
Shingara, J. et al. 2005. *RNA* 11: 1461-70.
Shoemaker, D. D. et al. 1996. *Nat. Genet.* 14: 367-70.
Shuber, A. P. et al. 1995. *Genome Res.* 5: 488-93.
Sioud, M., Rosok, O. 2004. *Biotechniques* 37: 574-6, 578-80.
Smith, R. D. et al. 2001. *Biotechniques* 31: 776-8, 780, 782.
Sorge, J. A., Mullinax, R. L. 2006. International Patent Application WO2006102309 A2.
Szymkowiak, C. et al. 2003. *J. Virol. Methods.* 107: 15-20.
Tang, X. et al. 2007. *RNA* 13: 1803-22.
Thisted, T. 2003. International Patent Application (PCT) WO030002761 A1.
Toulme, J. J. et al. 2001. *Prog. Nucleic Acid Res. Mol. Biol.* 69: 1-46.
Valoczi, A. et al. 2004. *Nucleic Acids Res.* 32: e175.
Vallejo, A. N. et al. 1994. *PCR Methods Appl.* 4: S123-30.
Van Huffel, C. et al. 2006. European Patent Application EP1627925 A1.
Vary, C. P. 1987. *Nucleic Acids Res.* 15: 6883-97.
Vagin, V. V. et al. *Science* 313: 320-4.
Vatolin, S. et al. 2006. *J. Mol. Biol.* 358: 983-96.
Wang, D. et al. 2003. *Biotechniques* 35: 300-2, 304, 306 passim.
Wang, H. et al. 2007. *RNA* 13: 151-9.
Wangh, L. J. et al. 2004. United States Patent Application US2004/0053254 A1.
Wark, A. W. et al. 2008. *Angew. Chem. Int. Ed. Engl.* 47: 644-52.
Weiler, J. et al. 2006. *Gene Ther.* 13: 496-502.
White, M. J. et al. 1991. *Anal. Biochem.* 199: 184-90.
Winkler, M. M. et al. 2006. United States Patent Application US2006/0078894 A1.
Wu, W. et al. 2007. *Int. J. Cancer* 120: 953-60.
Xi, Y. et al. 2007. *RNA* 13: 1668-74.
Xia, X. 2006. United States patent Application US2006/0246464 A1.
Xie, Z. et al. 2005. *Plant Physiology* 138: 2145-2154.
Yang, Z. et al. 2006. *Nucleic Acids Res.* 34: 667-75.
Yang, Z. et al. 2007. *Methods Enzymol.* 427: 139-54.
Ye, F. et al. 2001. *Hum. Mutat.* 17: 305-16.
Yehudai-Resheff, S., Schuster, G. 2000. *Nucleic Acids Res.* 28: 1139-44.
Yeung, M. L. et al. 2005. *Retrovirology* 2: 81.
Yu, B. et al. 2005. *Science* 307: 932-5.
Yu, J. et al. 2006. *Biochem. Biophys. Res. Commun.* 349: 59-68.
Zamore, P. D. Haley, B. 2005. *Science* 309: 1519-1524.
Zhang, D. Y. et al. 1998. *Gene* 211: 277-85.
Zhang, D. Y. et al. 2001. *Mol. Diagn.* 6: 141-50.
Zhang, D. et al. 2006. *Clin Chim Acta.* 363: 61-70.
Zhang, B., Farwell, M. A. 2008. *J. Cell. Mol. Med.* 12: 3-21.

The invention claimed is:

1. A method of detecting the presence of one or more target RNAs in a sample, said method comprising:
   a) ligating an adapter or linker oligonucleotide to the 3' end of said one or more target RNAs to produce one or more extended target polynucleotides;
   b) circularizing said one or more extended target polynucleotides by ligating the 5'-end of the one or more extended target polynucleotides to its 3'- end;
   c) synthesizing by rolling circle amplification complementary multimeric nucleic acids (MNAs) comprising multiple repeats of sequences that are complementary to said one or more circularized extended polynucleotides; and
   d) detecting said MNAs, thereby detecting the presence of said one or more target RNAs in said sample.

2. The method of claim 1, wherein said target RNA is 10 or more nucleotides in length and comprises:
   a) a 5'-phosphate (5'-p) or other 5'-end group that is optionally converted to 5'-p;
   b) a 3'-hydroxyl (3'-OH) or other 3'-end group that is optionally converted to 3'-OH; and
   c) a 2'-OH or 2'-OMe at its 3'-terminal nucleotide.

3. The method of claim 1, wherein said adapter or linker oligonucleotide is 10 or more nucleotides in length and comprises:
   a) RNA, or DNA, or a mix of DNA and RNA residues or chemical analogs thereof;
   b) a sequence selected from the group consisting of a promoter for an RNA polymerase; a sequence which is neither substantially complementary nor corresponds to any sequence expected to be present in said sample; a Zip-code sequence; a homopolynucleotide linker; and a sequence corresponding to or encoding a linker sequence used for cloning and sequencing;
   c) a 3'-end group selected from a 3'-OH and a 3'-p;
   d) a 5'-group selected from a 5'-p, a 5'-App, and a 5'-OH; and
   e) a 2'-group at the 3'-terminal nucleotide selected from a 2'-OH and a 2'-OMe.

4. The method of claim 1, wherein said synthesizing comprises:
   a) hybridizing said circularized extended target polynucleotide with an oligonucleotide RT primer that is complementary to said adapter; and
   b) enzymatically extending said RT primer bound to said circularized extended target polynucleotide by reverse transcriptase.

5. The method of claim 1, wherein said MNAs are cRNA and said synthesizing comprises:
   a) hybridizing an oligodeoxynucleotide to the adapter of said circularized extended target polynucleotide, wherein said oligodeoxynucleotide comprises one strand of a double-stranded promoter for an RNA polymerase and said adapter comprises the second strand of said promoter; and
   b) synthesizing said cRNA by transcription using said polymerase.

6. The method of claim 1, wherein said detecting comprises sequencing.

7. The method of claim 6, wherein said detecting further comprises PCR amplification of MNAs before said sequencing using reverse and forward PCR primers that are specific to said adapter sequence.

8. The method of claim 7, wherein said forward and/or reverse PCR primers comprise at their 3' ends sequences that are specific to said MNAs and at least one additional sequence at their 5' ends selected from:
   a) a sequence encoding a Zip-code sequence;
   b) a sequence encoding cloning and/or sequencing linker or adapter; and
   c) another adapter or linker sequence.

9. The method of claim 1, wherein said detecting comprises real-time qPCR amplification of said MNAs.

10. The method of claim 9, wherein said real-time qPCR amplification of MNAs is performed using a pair of forward and reverse PCR primers comprising sequences that are specific to said adapter sequence.

11. The method of claim 9, wherein said real-time qPCR amplification of MNAs is performed using a pair of forward and reverse PCR primers comprising sequences that are specific to a part of said adapter at their 5' ends and to a part of said target sequences at their 3' ends.

12. The method of claim 9, wherein said real-time qPCR of MNAs is performed using a pair of forward and reverse PCR primers comprising sequences that are:
   a) substantially complementary to each other at their 5' ends and can form a dimer with 3' overhangs, wherein said 5' overlap is ≥2 nt shorter than said target sequences while said 3'-end overhangs are ≥1 nt long; and
   b) complementary to the forward PCR primer is complementary to repeated target sequences with said multimeric cDNA; and
   c) the reverse PCR primer is corresponding to repeated target sequences within said multimeric cDNA.

13. The method of claim 1, wherein said target RNA is 100 or fewer nucleotides in length.

14. The method of claim 1, wherein said target RNA is a miRNA.

15. The method of claim 1, wherein said one or more target RNAs comprise multiple target RNAs.

16. The method of claim 15, wherein said multiple target RNAs comprise different target RNAs.

17. The method of claim 15, wherein said multiple target RNAs comprise a 2'OH at a 3' end, 2'-O-Me at a 3' end, or a combination thereof.

18. The method of claim 1, further comprising determining whether said one or more target RNAs comprise a 2'OH or 2'-O-Me at a 3' end of said one or more target RNAs.

19. The method of claim 1, wherein circularizing one or more extended target polynucleotides comprises use of one or more ligases.

20. The method of claim 19, wherein said one or more ligases is a RNA ligase, RNA/DNA ligase, or a combination thereof.

21. The method of claim 20, wherein the RNA ligase is a T4 RNA ligase.

22. The method of claim 20, wherein the RNA/DNA ligase is a CircLigase.

23. The method of claim 1, wherein the sample is derived from a cell.

24. The method of claim 1, wherein the sample comprises total cellular RNA or a cell lysate.

* * * * *